US009475849B2

(12) United States Patent
Laga et al.

(10) Patent No.: US 9,475,849 B2
(45) Date of Patent: Oct. 25, 2016

(54) BRASSICA PLANT COMPRISING A MUTANT INDEHISCENT ALLELE

(75) Inventors: Benjamin Laga, Wingene (BE); Bart den Boer, Merelbeke (BE); Bart Lambert, Ieper (BE)

(73) Assignee: Bayer CropScience N.V., Diegem (BE)

( * ) Notice: Subject to any disclaimer, the term of this patent is extended or adjusted under 35 U.S.C. 154(b) by 429 days.

(21) Appl. No.: 12/745,106

(22) PCT Filed: Nov. 25, 2008

(86) PCT No.: PCT/EP2008/010147
§ 371 (c)(1),
(2), (4) Date: May 27, 2010

(87) PCT Pub. No.: WO2009/068313
PCT Pub. Date: Jun. 4, 2009

(65) Prior Publication Data
US 2011/0030106 A1    Feb. 3, 2011

Related U.S. Application Data

(60) Provisional application No. 61/004,660, filed on Nov. 29, 2007.

(30) Foreign Application Priority Data

Nov. 28, 2007 (EP) .................................. 07023052

(51) Int. Cl.
*A01H 5/10* (2006.01)
*C07K 14/415* (2006.01)
*C12N 15/82* (2006.01)

(52) U.S. Cl.
CPC ......... *C07K 14/415* (2013.01); *C12N 15/8266* (2013.01)

(58) Field of Classification Search
USPC ....................................................... 800/278
See application file for complete search history.

(56) References Cited

U.S. PATENT DOCUMENTS

| 5,985,557 A | 11/1999 | Prudent et al. | |
| 6,001,567 A | 12/1999 | Brow et al. | |
| 7,135,621 B2 * | 11/2006 | Yanofsky et al. | 800/290 |
| 2005/0120417 A1 | 6/2005 | Yanofsky et al. | |
| 2007/0006336 A1 | 1/2007 | Yanofsky et al. | |

FOREIGN PATENT DOCUMENTS

| EP | 534858 | 3/1993 |
| WO | WO 97/13865 | 4/1997 |
| WO | WO 99/00503 | 1/1999 |
| WO | WO 01/59122 | 8/2001 |
| WO | WO 01/79517 | 10/2001 |
| WO | WO 2004/113542 | 12/2004 |
| WO | WO 2006/009649 | 1/2006 |

OTHER PUBLICATIONS

Kim et al., EMS Mutagenesis of Arabidopsis in 323 Molecular Biology: Arabidopsis Protocols 2nd Ed., 101-103 (2006).*
Liljegren et al. (Control of Fruit Patterning in Arabidopsis by INDEHISCENT, 116 Cell, 844 (2004).*
Heim et al. (The Basic Helix-Loop-Helix Transcription Factor Family in Plants: A Genomic-Wide Study of Protein Structure and Functional Diversity, 20 Mol. Biol. Evol., 735-747 (2003).*
Dinneny et al. (Drawing lines and borders: how the dehiscent fruit of Arabidopsis is patterned, 27 BioEssays, 42-49 at 48 (2004)).*
Atchley and Fitch, PNAS, vol. 94, pp. 5172-5176 (1997).
Atchley et al., Journal of Molecular Evolution vol. 48, pp. 501-516 (1999).
Ausubel et al. Current Protocols in Molecular Biology, Current Protocols, USA, vols. 1 and 2 (1994).
Brownlie et al., Structure vol. 5, pp. 509-520 (1997).
Bruce et al., Journal of Agricultural Engineering Research, vol. 80, pp. 343-350 (2001).
Brown, Molecular Biology LabFax, Second Edition, Academic Press (UK), vols. I and II (1998).
Child and Hutdy, Proceedings of the 10th International Rapeseed Congress (1999).
Child et al., Journal of Experimental Botany, vol. 49, pp. 829-838 (1998).
Child et al., Journal of Experimental Botany, vol. 54, No. 389, pp. 1919-1930 (2003).
Dieffenbach and Dveksler, PCR Primer: A Laboratory Manual, Cold Spring Harbor Laboratory Press (1995).
Dinneny et al., Development, vol. 131, pp. 1101-1110 (2004).
Dinneny et al., Development vol. 132, pp. 4687-4696 (2005).
Ferrandiz et al., Science, vol. 289, pp. 436-438 (2000).
Gu et al., Development vol. 125, pp. 1509-1517 (1998).
Heim et al., Molecular Biology and Evolution, vol. 20, pp. 735-747 (2003).
Henikoff et al., Plant Physiology, vol. 135, No. 2, pp. 630-636 (2004).
Kadkol et al., Australian Journal of Botany, vol. 345, pp. 595-601 (1986).
Ledent and Vervoort, Genome Research, vol. 11, pp. 754-770 (2001).
Li et al., Plant Journal, vol. 27, pp. 235-242 (2001).
Liljegren et al., Nature, vol. 404, pp. 766-770 (2000).
Liljegren et al., Cell, vol. 116 pp. 843-853 (2004).
Li and Zhang, Functional Integrative Genomics, vol. 2, pp. 254-258 (2002).
Mandel and Yanofsky, Plant Cell, vol. 7, pp. 1763-1771 (1995).
McCallum et al., Nature Biotechnology, vol. 18, pp. 455-457 (2000).
McCallum et al., Plant Physiology, vol. 123, pp. 439-442 (2000).
McPherson at al., PCR—Basics: From Background to Bench, First Edition, Springer Verlag, Germany (2000).

(Continued)

*Primary Examiner* — Elizabeth McElwain
(74) *Attorney, Agent, or Firm* — Arent Fox LLP

(57) ABSTRACT

This invention relates to crop plants of which the fruit dehiscence properties are modulated. More specifically the invention relates to improved methods and means for reducing seed shattering, or delaying seed shattering until after harvest, in plants, while maintaining at the same time an agronomically relevant threshability of the pods.

10 Claims, 2 Drawing Sheets

(56) References Cited

OTHER PUBLICATIONS

Meakin and Roberts, Journal Experimental Botany, vol. 41, pp. 995-1011 (1990).
Morgan et al., Fields Crop Research vol. 58, pp. 153-165 (1998).
Morgenstern and Atchley, Molecular Biology and Evolution, vol. 16, pp. 1654-1663 (1999).
Mott, Computer Applications, vol. 13, pp. 477-478 (1997).
Murreetal., Cell, vol. 56, pp. 777-783 (1989).
Needleman and Wunsch, Journal Molecular Biology, vol. 48, pp. 443-453 (1970).
Ohno et al., Development, vol. 131, pp. 1111-1122 (2004).
Petersen et al., Plant Molecular Biology, vol. 31, 517-527 (1996).
Prakash and Chopra, Plant Breeding, vol. 101, pp. 167-168 (1998).
Prakash and Chopra, Genetical Research, vol. 56, pp. 1-2 (1990).
Rajani et al., Current Biology, vol. 11, pp. 1914-1922 (2001).
R.D.D. Croy, Biology Labfax, jointly published by BIOS Scientific Publications Ltd (UK) and Blackwell Scientific Publications, UK (1993).
Rice et al., Trends in Genetics, vol. 16, No. 6, pp. 276-277 (2000).
Roeder et al., Current Biology, vol. 13, pp. 1630-1635 (2003).
Sambrook et al., Molecular Cloning: A Laboratory Manual, Second Edition, Cold Spring Harbour Laboratory Press, NY (1989).
Sambrook and Russell, Molecular Cloning: A Laboratory Manual, Third Edition, Cold Spring Harbor Laboratory Press, NY (2001).
Sawa et al., Genes and Development, vol. 13, pp. 1079-1088 (1999).
Siegfried et al., Development, vol. 126, pp. 4117-4128, (1999).
Snowdon, Chromosome Research, vol. 15, pp. 85-95 (2007).
Spence et al., Journal of Microscopy, vol. 181, pp. 195-203 (1996).
Toledo-Ortiz et al., Plant Cell, vol. 15, pp. 1749-1770 (2003).
Vancanneyt et al., XIII International Conference on Arabidopsis Research, Sevilla, Spain, Jun. 28-Jul. 2, 2002).
Vos et al., NAR vol. 23, pp. 4407-4414 (1995).
Wu et al., Planta, vol. 224, pp. 971-979 (2006).
Quong et al., Molecular and Cellular Biology, vol. 113, pp. 792-800 (1993).
Lysak, et al. (Apr. 1, 2005) "Chromosome triplication found across the tribe *Brassiceae*." Genome Research 15(4): 516-525.
Barker, et al. (Aug. 1, 2007) "Novel insights into seed fatty acid synthesis and modification pathways from genetic diversity and quantitative trait loci analysis of the *Brassica* C genome." Plant Physiology 144(4): 1827-1842.
Bruce et al., Journal of Agricultural Engineering Research, vol. 80, No. 4, pp. 343-350 (2001).
Bruce et al., Biosystems Engineering, vol. 81, No. 2, pp. 179-184 (2002).
Davies et al., Journal of Materials Science, vol. 32, pp. 5895-5899 (1997).
Li et al., Functional and Integrative Genomics, vol. 2, pp. 254-258 (2002).
Murre et al., Cell, vol. 56, pp. 777-783 (1989).
Ptashne, Nature, vol. 335, No. 20, pp. 683-689 (1988).

* cited by examiner

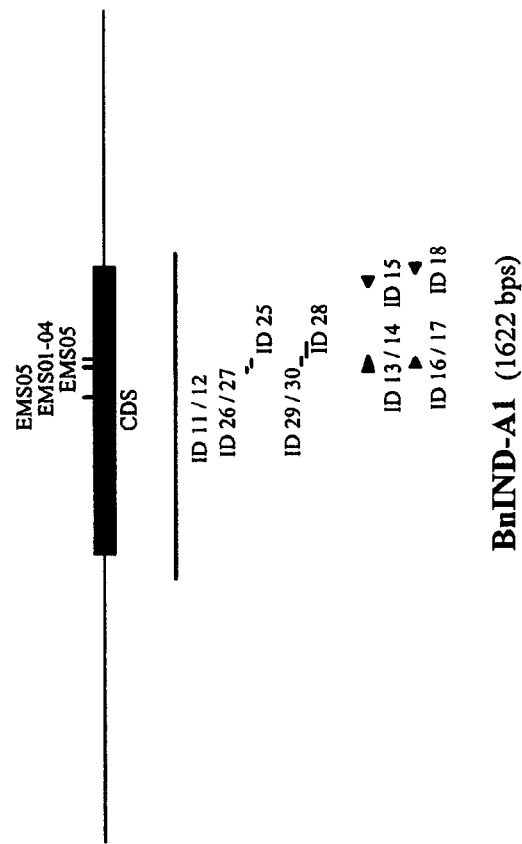

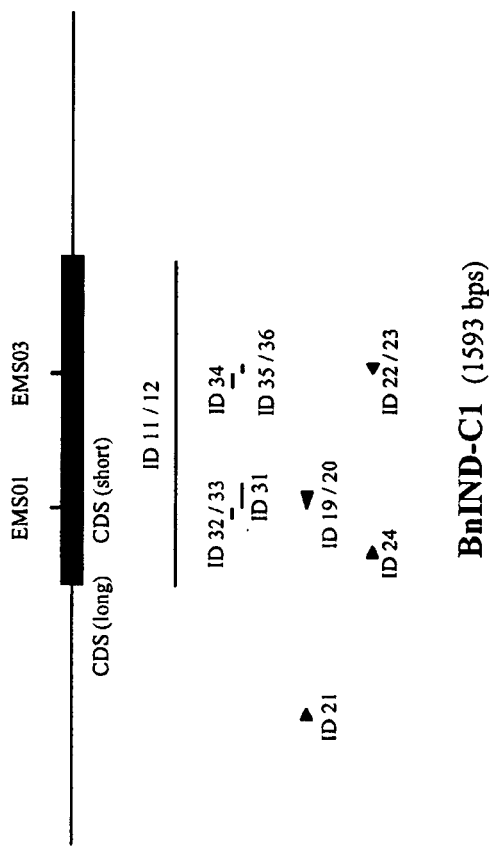

US 9,475,849 B2

BRASSICA PLANT COMPRISING A MUTANT INDEHISCENT ALLELE

CROSS-REFERENCE TO RELATED APPLICATIONS

This application is the U.S. National Stage filing of International Patent Application No. PCT/EP2008/010147, filed Nov. 25, 2008, which claims priority to EP 07023052.9, filed Nov. 28, 2007, and U.S. Provisional Patent Application No. 61/004,660, filed Nov. 29, 2007, the disclosures of each of which are hereby incorporated by reference.

FIELD OF THE INVENTION

This invention relates to the field of agricultural products, especially crop plants, particularly of the Brassicaceae family, in particular *Brassica* species, of which the fruit dehiscence properties are modulated. More specifically the invention relates to improved methods and means for reducing seed shattering, or delaying seed shattering until after harvest, in plants such as Brassicaceae plants, particularly Brassicaceae plants grown for seed production, while maintaining at the same time an agronomically relevant treshability of the pods. Provided are both wild type and mutant nucleic acid molecules encoding *Brassica* INDEHISCENT proteins (IND) and the proteins as such. Also provided are *Brassica* plants comprising at least two IND genes, in particular *Brassica napus* plants, and cells, parts, seeds and progeny thereof, characterized in that they comprise three full knock-out mutant ind alleles in their genome, whereby the fruit dehiscence properties are significantly altered. In addition, methods for generating *Brassica* plants in which seed shattering is reduced, or in which seed shattering is delayed until after harvest, while an agronomically relevant treshability of the pods is preferably maintained, are provided herein, as are seed pods and seeds obtainable from such plants. Further provided are detection tools (kits) and methods for detecting the presence of one or more mutant ind and/or wild type IND alleles in biological samples, as well as methods for transferring one or more mutant ind and/or wild type IND alleles to other plants and methods for combining different ind and/or IND alleles in plants. In particular, methods for combining a suitable number of mutant ind alleles, which encode non-functional or no IND proteins and/or IND proteins having significantly reduced activity in vivo, in such a way as to significantly reduce seed shattering, or to delay seed shattering until after harvest, while maintaining at the same time an agronomically relevant treshability of the pods. In addition uses of the plants, or parts thereof, and/or progeny thereof, seeds and seed oils and the methods and/or kits of the invention are provided. Also provided are methods and means to increase the yield, particularly grain and seed yield. The yield increase phenotype may be separate from the reduced or delayed seed shatter phenotype.

BACKGROUND OF THE INVENTION

Siliques or pods from *Brassica* plants release their seeds through a process called fruit dehiscence. A silique consists of two carpels joined margin to margin. The suture between the margins forms a thick rib, called replum. As pod maturity approaches, the two valves separate progressively from the replum, along designated lines of weakness in the pod, eventually resulting in the shattering of the seeds that were attached to the replum. The dehiscence zone defines the exact location of the valve dissociation.

Shedding of seed (also referred to as "seed shatter" or "pod shatter") by mature pods before or during crop harvest is a universal phenomenon with crops that develop dry dehiscent fruits. Premature seed shatter results in a reduced seed recovery, which represents a problem in crops that are grown primarily for the seeds, such as oil-producing *Brassica* plants, particularly oilseed rape. Another problem related to premature seed shattering is an increase in volunteer growth in the subsequent crop year. In oilseed rape, pod shatter-related yield losses are on average 20% (Child et al., 1998, J Exp Bot 49: 829-838), but can reach up to 50%, depending on the weather conditions (MacLeod, 1981, Harvesting in Oilseed Rape, pp. 107-120 Cambridge Agricultural Publishing, Cambridge).

Current commercial oilseed rape varieties are extremely susceptible to shattering. There is little variation for resistance to shattering within existing breeding programs of *B. napus* but resistant lines have been found within the diploid parents of *B. napus* (*B. oleracea* and *B. rapa*) as well as within other members of the *Brassica* genus, notably *B. juncea*, *B. carinata* and *B. nigra*. Kadkol et al. (1986, Aust. J. Botany 34 (5): 595-601) report increased resistance towards shattering in certain accessions of *B. campestris* that was associated with the absence of a separation layer in the region of attachment of the siliqua valves to the replum. Prakash and Chopra (1988, Plant breeding 101: 167-168) describe the introgression of resistance to shattering in *Brassica napus* from *Brassica juncea* through non-homologous recombination. Spence et al. (1996, J of Microscopy 181: 195-203) describe that some lines of *Brassica juncea* show a reduced tendency to shatter as compared to *Brassica napus* lines. Morgan et al., 1998 (Fields Crop Research 58, 153-165) describe genetic variation for pod shatter resistance among lines of oilseed rape developed from synthetic *B. napus* and conclude that lines which required much energy to open their pods appeared to have increased vascularisation in the dehiscence zone and to have reduced cell wall degradation within the dehiscence zone. They further found a significant negative correlation between the length of the pod beak and the force needed to cause pod shattering. Child and Huttly (1999, Proc 10th Int. Rapeseed Congress) describe variation in pod maturation in an irradiation-induced mutant *B. napus* and a population of its parent cultivar, Jet Neuf, wherein the most resistant wild-type and mutant plants showed much lignification of groups of cells throughout the dehiscence zone and wherein vascular traces situated close to the inner edge of the dehiscence zone in the mutant were described to help to secure the valves. Child et al. (2003, J Exp Botany 54 (389): 1919-1930) further describe the association between increased pod shatter resistance and changes in the vascular structure in pods of a resynthesized *Brassica napus* line. However, the traditional methods for breeding have been unsuccessful in introducing shatter resistance into rape cultivars, without interference with other desirable traits such as early flowering, maturity and blackleg resistance (Prakash and Chopra, 1990, Genetical Research 56: 1-2).

Several genes, which promote or inhibit pod dehiscence, have been identified in *Arabidopsis thaliana* through mutant analysis: Combined mutants in both SHATTERPROOF1 (SHP1; initially referred to as AGL1) and SHATTERPROOF2 (SHP2; initially referred to as AGL5) result in indehiscent siliques (i.e. siliques which remain closed upon maturity in *Arabidopsis thaliana*) (Liljegren et al., 2000, Nature 404, 766-770). Similarly, mutants in the INDEHIS- CENT gene (referred to as IND1) in *Arabidopsis thaliana* (Liljegren et al., 2004, Cell 116: 843-853; PCT publication WO 01/79517), as well as in ALCATRAZ (referred to as ALC; Rajani et al. 2001, Current Biology 11, 1914-1922) interfered with pod dehiscence leading to pod shatter resistance. Constitutive expression of FRUITFUL (FUL), a repressor of SHP and IND, in *Arabidopsis thaliana* also resulted in indehiscent siliques (Ferrandiz et al., 2000, Science, 289, 436-438). These transcription factors are believed to form a non-linear transcriptional network that controls valve margin identity and pod shatter. Liljegren et al. (2004, Cell 116: 843-853) further describe that IND, an atypical basic helix-loop-helix (bHLH) gene, directs the differentiation of the valve margin into the separation and lignified layers in *Arabidopsis thaliana*. The layer of lignified cells adjacent to the separation layer along with the endocarp b layer (a single lignified cell layer in each valve) produce a spring-like tension within the drying fruit that contributes to its opening. Lignification of the valve endodocarp b layer requires the activities of IND, SHP, ALC, and FUL, a MADS-domain transcription factor that is expressed throughout the valves (Liljegren et al., 2004, supra; Mandel and Yanofsky, 1995, Plant Cell 7, 1763-1771). FUL and REPLUMLESS (RPL), a homeodomain transcription factor that is expressed in the replum (Roeder et al., 2003, Curr Biol 13, 1630-1635), have been found to set the boundaries of the genes that confer valve margin identity (Gu et al., 1998, Development 125, 1509-1517; Ferrandiz et al., 2000, Science, 289, 436-438; Roeder et al., 2003, supra). Finally, FILAMENTOUS FLOWER (FIL) and YABBY3 (YAB3), two YABBY-family transcription factors (Sawa et al., 1999, Genes Dev 13, 1079-1088; Siegfried et al., 1999, Development 126, 4117-4128), and JAGGED (JAG), a C2H2 zinc-finger transcription factor (Dinneny et al., 2004, Development 131, 1101-1110; Ohno et al., 2004, Development 131, 1111-1122), were identified to redundantly contribute to proper valve and valve margin development by promoting the expression of FUL and SHP in a region-specific manner (Dinneny et al., 2005, Development 132, 4687-4696). Genes for a number of hydrolytic enzymes, such as endopolygalacturonases, which play a role, during pod dehiscence, in the programmed breakdown of the dehiscence zone in pods from *Brassica* plants have also been identified (see e.g. WO 97/13865; Petersen et al., Plant. Mol. Biol., 1996, 31:517-527).

Liljegren et al. (2004, Cell 116: 843-853) describe five mutant alleles of *Arabidopsis* IND. The lignified cells in the dehiscence zone are either absent or present in plants comprising these mutant alleles depending on the severity of the mutations (severe ind mutants do not contain lignified cells in the region corresponding to the inner part of the valve margin in wild-type plants), but in all cases the silique is indehiscent. Wu et al. (2006), Planta 224, 971-979) describe a sixth mutant allele of *Arabidopsis* IND. Plants comprising this mutant allele show no lignified cells at the junctions of the valve margin and the replum, contain fewer cells in a region of seven layers of cells, which appeared to encompass the commonly known dehiscence zone and replum border in wild-type plants, and exhibit incomplete cytokinesis in this layer.

US 2005/0120417 and US 2007/0006336 describe the identification and isolation of two IND1 orthologs from *Brassica napus*.

WO99/00503, WO01/79517 and WO0159122 describe downregulation of the expression of the *Arabidopsis* ALC, IND, AGL1 and AGL5 genes and orthologs thereof using gene-silencing techniques (such as antisense suppression or cosuppression) and mutagenesis.

Vancanneyt et al., 2002 (XIII International Conference on *Arabidopsis* Research, Sevilla, Spain Jun. 28-Jul. 2, 2002) reported that the expression of FUL from *A. thaliana* under control of a CaMV 35S promoter in oilseed rape resulted in a number of pod shatter resistant transformants. Pods of such pod shatter resistant lines had no dehiscence zone, and opening of the pods could only be achieved by random fracture of the valves by applying considerable pressure.

Vancanneyt et al., 2002 (XIII International Conference on *Arabidopsis* Research, Sevilla, Spain Jun. 28-Jul. 2, 2002) also reported that silencing of the IND gene in *Arabidopsis thaliana* using so-called dsRNA silencing techniques resulted in almost complete pod shatter resistance. Ninety-eight percent of the transgenic *Arabidopsis* lines developed siliques, which did not open along the valve suture, and could only be opened by applying considerable pressure to the valves.

It is important to realize that while seed shattering constitutes an important problem in oilseed rape culture, which may be solved by developing pod shatter resistant lines, ultimately, separation of the seeds from the pods is still required. In normal agricultural practice this is achieved by treshing of the pods by a combine harvester. Treshing of the pods by a combine harvester must be complete and must cause minimum damage to the seeds thus released. However, as pod strength increases, the more severe action required to tresh them causes an unacceptable level of damage to the seed. The pods of pod shatter resistant Brassicaceae plants should thus not be so strong that they cannot be treshed in a combine harvester (Bruce et al. 2001, J. Agric. Engng Res. 80, 343-350).

WO 2004/113542 describes that moderate dsRNA gene silencing of genes involved in the development of the dehiscence zone and valve margins of pods in Brassicaceae plants allows the isolation of transgenic lines with increased pod shatter resistance and reduced seed shattering, the pods of which however may still be opened along the dehiscence zone by applying limited physical forces.

Despite the fact that sequences of specific IND genes and mutant sequences thereof, particularly *Arabidopsis* and *Brassica napus* IND gene sequences and mutant *Arabidopsis* IND gene sequences, are available in the art, a need remains for further IND gene sequences, e.g. to enable a specifically desired modification of seed shattering in plants, such as *Brassica napus* plants. The isolation of mutant alleles corresponding to ind in economically important Brassicaceae plants, such as oilseed rape, is a laborious and time consuming task. Moreover, such isolation may be complicated by the amphidiploidy in oilseed rape and the consequent functional redundancy of the corresponding genes.

These and other objects are achieved by the present invention, as indicated by the various embodiments described in the summary of the invention, figures, detailed description, examples and claims.

SUMMARY OF THE INVENTION

The inventors have found that the fruit dehiscence properties in *Brassica* plants can be controlled by controlling the number of IND genes/alleles that are "functionally expressed" in seed pods, i.e. that result in functional (biologically active) IND protein. By combining a number of full knock-out mutant IND alleles ("ind alleles"), while maintaining a minimal number of wild type IND alleles, resulting in a minimal level of functional IND protein, the dehiscence properties of the seed pods can be modified, more specifically pod shatter resistance can be increased and seed shattering can be reduced, or seed shattering can be delayed until after harvest, while maintaining at the same time an agronomically relevant treshability of the pods, such that the pods may still be opened along the dehiscence zone by applying limited physical forces. It is thought that a minimal number of wild type IND alleles is needed to still enable the separation of the seeds from the pods, in particular by treshing of the pods by a combine harvester, such that the treshing of the pods is complete and causes minimum damage to the seeds thus released.

Thus, in a first aspect, the present invention provides a Brassica plant comprising at least two IND genes, in particular a Brassica napus plant (and parts thereof, such as seed pods and seeds), characterized in that it comprises three full knock-out mutant IND alleles in its genome, in particular of an IND-A1 and/or an IND-C1 gene, and wherein the pod shatter resistance of the plant is significantly increased compared to the pod shatter resistance of a plant not comprising mutant IND alleles, but wherein the plant preferably maintains an agronomically relevant treshability of the pods.

In another aspect, the invention provides (isolated) nucleic acid sequences encoding wild type and/or mutant IND proteins, as well as fragments thereof, and methods of using these nucleic acid sequences to modify the fruit dehiscence properties of plants. Also provided are the proteins themselves and their use.

The invention further relates to a plant, and cells, parts, seeds and progeny thereof, comprising at least one full knock-out mutant IND allele, and thus a reduced amount of functional IND protein compared to a plant, and cells, parts, seeds and progeny thereof, comprising an IND allele encoding the corresponding functional IND protein. Such plants, and cells, parts, seeds and progeny thereof, can be used for obtaining plants with modified fruit dehiscence properties, in particular for obtaining Brassica plants with significantly reduced seed shattering that maintain an agronomically relevant treshability of the pods. As used herein, "plant part" includes anything derived from a plant of the invention, including plant parts such as cells, tissues, organs, seeds, seed pods, seed meal, seed cake, seed fats or oils.

In a further aspect, the invention relates to seed pods with modified shatter resistance, which can be obtained from a plant according to the present invention, and the use of said seed pods, for example for planting and growing progeny from the plants.

In yet another aspect of the invention, methods are provided for generating and selecting plants, and cells, parts, seeds and progeny thereof, containing at least one full knock-out ind allele. In particular, methods are provided for generating and selecting Brassica plants comprising at least two IND genes, in particular Brassica napus plants, and cells, parts, seeds and progeny thereof, containing at least one full knock-out mutant ind allele present at least one of the at least two different IND loci in the genome, for example at least one of the two different loci of the Brassica IND-A1 and IND-C1 gene, and to distinguish between the presence of mutant ind alleles and wild type IND alleles in a plant or plant part. Thus methods are provided (such as mutagenesis and/or marker assisted selection) for generating and/or identifying ind alleles or plants or plant parts comprising such alleles and for combining a suitable number of ind alleles and/or different types of ind alleles in a single plant, whereby the fruit dehiscence properties of this plant are significantly modified.

In another embodiment of the invention, the mutant IND alleles of the invention are used to increase the yield of harvested seed or grain from Brassica plants. The increased yield may be a consequence of reducing or delaying seed shattering, but may also be independent from the reduced or delayed seed shatter. In particular, Brassica plants are provided comprising at least two IND genes, or a cell, part, seed or progeny thereof, characterized in that these plants comprise two mutant homozygous IND alleles as herein described in their genome.

FIGURE LEGENDS

FIG. 1—Schematical representation of the IND-A1 gene, encoding a wild-type IND-A1 protein from Brassica napus (SEQ ID NO: 5).

FIG. 2—Schematical representation of the IND-C1 gene, encoding a wild-type IND-C1 protein from Brassica napus (SEQ ID NO: 7).

In FIGS. 1 and 2 the position of the mutations described in the Examples (named "EMSxx" according to their respective "ind-x1-EMSxx" name as described in the Examples) is indicated with vertical lines; the length and position of the IND specific probes (named "ID xx" according to their respective SEQ ID NO: xx) are indicated by horizontal lines below the schematical representation of the IND genes; the position of the IND specific primers (named "ID xx" according to their respective SEQ ID NO: xx) are indicated by arrowheads.

GENERAL DEFINITIONS

"Increase of pod shatter resistance" and "reduction of seed shattering", as used herein, refers to a decreased seed shatter tendency and/or a delay in the timing of seed shattering, in particular until after harvest, of Brassica plants, the fruits of which normally do not mature synchronously, but sequentially, so that some pods burst open and shatter their seeds before or during harvest. The level of resistance to pod shattering is positively correlated with and can, for example, be measured by determining the force needed to break pods in the 'tensile separation test' (Davies and Bruce, 1997, J Mat Sci 32: 5895-5899; Morgan et al., 1998, Fields Crop Research 58, 153-165), the number of intact pods remaining after e.g. 20 sec ('IP20'; Morgan et al., 1998, supra), 9.7 or 17 sec (Bruce et al., 2002, Biosystems Eng 81(2): 179-184) in a 'random impact test', the pod sample half-life ('LD50') in a random impact test, i.e. the treatment time needed to cause the opening of 50% of the pods in tested pod samples, and the 'field score for shattering' (Morgan et al., 1998, supra). Random impact tests (RITs) and algorithms to define the pod sample half-lives in such RITs have been described in Bruce et al., 2002 (supra), Morgan et al., 1998 (supra) and the Examples below. Both publications are hereby incorporated by reference. Briefly, a sample of intact mature pods is placed in a closed drum together with steel balls and the drum is then vigorously agitated for increasing periods of times (e.g. 10 s, 20 s, 40 s, 80 s). After each period, the drum is opened and the number of broken and damaged pods is counted. The most accurate estimation of the level of shattering resistance for each line is calculated by fitting a linear×linear curve to all the available data and estimating the time taken for half of the pods within a sample to be broken ("pod sample half-life" or "LD50"). It is important however that pods open mainly along the dehiscence zone, and are not simply pulverized, as may occur with indehiscent pods.

An "agronomically relevant increase of pod shatter resistance", as used herein, refers to an increase of pod shatter resistance in a plant which results in pod shatter-related yield losses in the field (pre-harvest) below those normally observed for that plant in the field. For oilseed rape, pod shatter-related yield losses in the field are reported to be about 11% for a season with on average good growth conditions and about 25% for a season with on average bad growth conditions. A positive correlation has been found between these levels of seed loss and the level of seed loss at 9.7 s and 17 s treatment time, respectively, in the random impact test as described by Bruce et al., 2002 (Biosystems Eng 81(2): 179-184). Alternatively, to determine whether the level of resistance to pod shattering in a plant is agronomically relevant, the pod sample half-life ('LD50', see above) of the plant can be compared with the pod sample half-life of a plant known to have an average level of pod shatter resistance, such as, for oilseed rape, all currently commercially available oilseed rape varieties.

As used herein, "pod or seed shattering" or "fruit or pod dehiscence" refers to a process that takes place in a fruit after seed maturation, whereby the valves detach from the central septum freeing the seeds. The region that breaks (i.e. the "dehiscence zone") runs the entire length of the fruit between the valves and the replum (external septum). At maturity, the "dehiscence zone" is essentially a non-lignified layer of cells between a region of lignified cells in the valve and the replum. Shattering occurs due to the combination of cell wall loosening in the dehiscence zone and the tensions established by the differential mechanical properties of the drying cells in the silique.

A Brassica "fruit", as used herein, refers to an organ of a Brassica plant that develops from a gynoecium composed of fused carpels, which, upon fertilization, grows to become a "(seed) pod" or "silique" that contains the developing seeds. A Brassica "(seed) pod" or "silique" consists of a fruit wall (carpel) enclosing two locules separated by the septum. The "dehiscence zones" develop at the carpel margins adjacent to the septum and run the length of the silique. The cells of the dehiscence zone eventually begin to degrade and this weakens the contact between the carpel walls or valves and the septum. The loss of cellular cohesion is confined to the cells of the dehiscence zone and results from middle lamella breakdown (Meakin and Roberts, 1990, J Exp Bot 41, 995-1011).

"Dehiscence zones", as used herein, refers to layers of simple, parenchymatous cells, contained in the sutures situated on both sides of the bi-valved pod of plants, in particular Brassica plants. The dehiscence zones are situated between the pod valve edge and a central replum that contains the main vascular bundle to the stalk or pedicel. Dissociation of the cells in the dehiscence zone takes place during pod senescence and is complete by the time the pods reach full maturity (Meakin and Roberts, 1990, supra). Valve separation can than take place. The dehiscence zone contains vascular traces, which pass from the pod wall to the pedicel (stalk) and the replum. The process of pod shatter takes place only after external force fractures the delicate vascular threads, allowing the valves to separate and the seeds to fall to the ground. This occurs during disturbance of the canopy, for example by contact with the combine during harvesting. The vascular tissue contains thickened, lignified cells, which form the collenchymatous groups of cells found adjacent to the conductive cells (Meakin and Roberts, 1990, supra). This provides rigidity to the tissue and presumably, some resistance to fracturing.

As used herein, "an agronomically relevant treshability" refers to the resistance of a pod, particularly an oilseed rape pod, to opening along the dehiscence zone of the pod with concurrent release of the seeds, upon application of physical forces that allow complete opening of the pods while preventing damage to the seeds, as they are used e.g. in a combine harvester. A positive correlation has been found between a pod sample half-life ('LD50') in a random impact test and their treshability. Oilseed rape pod sample half-lives, as determined in a RIT performed as described in the Examples, which correspond to agronomically relevant treshability should not exceed 80 seconds. Typical sample half-life values for control lines of commercially available oilseed rape varieties are about 10 seconds. Thus, lines with significantly increased pod shatter resistance with agronomically relevant treshability have a pod sample half-life in RIT between about 10 and about 80 seconds, between about 10 and about 60 seconds, between about 10 and about 50 seconds, between about 20 and about 60 seconds, between about 20 and about 50 seconds, between about 40 and about 60 seconds, of about 57 seconds.

"Crop plant" refers to plant species cultivated as a crop, such as Brassica napus (AACC, 2n=38), Brassica juncea (AABB, 2n=36), Brassica carinata (BBCC, 2n=34), Brassica rapa (syn. B. campestris) (AA, 2n=20), Brassica oleracea (CC, 2n=18) or Brassica nigra (BB, 2n=16). The definition does not encompass weeds, such as Arabidopsis thaliana.

The term "nucleic acid sequence" (or nucleic acid molecule) refers to a DNA or RNA molecule in single or double stranded form, particularly a DNA encoding a protein or protein fragment according to the invention. An "endogenous nucleic acid sequence" refers to a nucleic acid sequence within a plant cell, e.g. an endogenous allele of an IND gene present within the nuclear genome of a Brassica cell. An "isolated nucleic acid sequence" is used to refer to a nucleic acid sequence that is no longer in its natural environment, for example in vitro or in a recombinant bacterial or plant host cell.

The term "gene" means a DNA sequence comprising a region (transcribed region), which is transcribed into an RNA molecule (e.g. into a pre-mRNA, comprising intron sequences, which is then spliced into a mature mRNA, or directly into a mRNA without intron sequences) in a cell, operable linked to regulatory regions (e.g. a promoter). A gene may thus comprise several operably linked sequences, such as a promoter, a 5' leader sequence comprising e.g. sequences involved in translation initiation, a (protein) coding region (cDNA or genomic DNA) and a 3' non-translated sequence comprising e.g. transcription termination sites. "Endogenous gene" is used to differentiate from a "foreign gene", "transgene" or "chimeric gene", and refers to a gene from a plant of a certain plant genus, species or variety, which has not been introduced into that plant by transformation (i.e. it is not a "transgene"), but which is normally present in plants of that genus, species or variety, or which is introduced in that plant from plants of another plant genus, species or variety, in which it is normally present, by normal breeding techniques or by somatic hybridization, e.g., by protoplast fusion. Similarly, an "endogenous allele" of a gene is not introduced into a plant or plant tissue by plant transformation, but is, for example, generated by plant mutagenesis and/or selection or obtained by screening natural populations of plants.

"Expression of a gene" or "gene expression" refers to the process wherein a DNA region, which is operably linked to appropriate regulatory regions, particularly a promoter, is transcribed into an RNA molecule. The RNA molecule is then processed further (by post-transcriptional processes) within the cell, e.g. by RNA splicing and translation initiation and translation into an amino acid chain (polypeptide), and translation termination by translation stop codons. The term "functionally expressed" is used herein to indicate that a functional protein is produced; the term "not functionally expressed" to indicate that a protein with significantly reduced or no functionality (biological activity) is produced or that no protein is produced (see further below).

The terms "protein" or "polypeptide" are used interchangeably and refer to molecules consisting of a chain of amino acids, without reference to a specific mode of action, size, 3-dimensional structure or origin. A "fragment" or "portion" of an IND protein may thus still be referred to as a "protein". An "isolated protein" is used to refer to a protein that is no longer in its natural environment, for example in vitro or in a recombinant bacterial or plant host cell. The term "transcription factor" is used to refer to a protein consisting of at least two discrete domains—a DNA binding domain and an activation or repression domain—that operate together to modulate the rate of transcriptional initiation from target gene promoters (Ptashne, 1988, Nature 335, 683-689). The term "basic helix-loop-helix (bHLH) domain transcription factor" is used to refer to a transcription factor comprising, apart from the bHLH DNA binding domain (Heim et al., 2003, Mol Biol Evol 20, 735-747; Toledo-Ortiz et al., 2003, Plant Cell 15, 1749-1770), domains which are known to be important for the regulation of gene expression which may be conserved at the amino acid level in related proteins from different species (Quong et al., 1993, Mol Cell Biol 13, 792-800). Transcriptional regulators comprising a bHLH domain bind DNA through residues in the basic region while the helix-loop-helix domain promotes dimerization, allowing family members to form hetero- or homodimers (Murre et al., 1989, Cell 56, 777-783).

The term "IND gene" refers herein to a nucleic acid sequence encoding an INDEHISCENT (IND) protein, which is a bHLH domain transcription factor required for seed dispersal (Liljegren et al., 2004, Cell 116: 843-853).

As used herein, the term "allele(s)" means any of one or more alternative forms of a gene at a particular locus. In a diploid (or amphidiploid) cell of an organism, alleles of a given gene are located at a specific location or locus (loci plural) on a chromosome. One allele is present on each chromosome of the pair of homologous chromosomes.

As used herein, the term "homologous chromosomes" means chromosomes that contain information for the same biological features and contain the same genes at the same loci but possibly different alleles of those genes. Homologous chromosomes are chromosomes that pair during meiosis. "Non-homologous chromosomes", representing all the biological features of an organism, form a set, and the number of sets in a cell is called ploidy. Diploid organisms contain two sets of non-homologous chromosomes, wherein each homologous chromosome is inherited from a different parent. In amphidiploid species, essentially two sets of diploid genomes exist, whereby the chromosomes of the two genomes are referred to as "homeologous chromosomes" (and similarly, the loci or genes of the two genomes are referred to as homeologous loci or genes). A diploid, or amphidiploid, plant species may comprise a large number of different alleles at a particular locus.

As used herein, the term "heterozygous" means a genetic condition existing when two different alleles reside at a specific locus, but are positioned individually on corresponding pairs of homologous chromosomes in the cell.

Conversely, as used herein, the term "homozygous" means a genetic condition existing when two identical alleles reside at a specific locus, but are positioned individually on corresponding pairs of homologous chromosomes in the cell.

As used herein, the term "locus" (loci plural) means a specific place or places or a site on a chromosome where for example a gene or genetic marker is found. For example, the "IND-A1 locus" refers to the position on a chromosome of the A genome where the IND-A1 gene (and two IND-A1 alleles) may be found, while the "IND-C1 locus" refers to the position on a chromosome of the C genome where the IND-C1 gene (and two IND-C1 alleles) may be found.

Whenever reference to a "plant" or "plants" according to the invention is made, it is understood that also plant parts (cells, tissues or organs, seed pods, seeds, severed parts such as roots, leaves, flowers, pollen, etc.), progeny of the plants which retain the distinguishing characteristics of the parents (especially the fruit dehiscence properties), such as seed obtained by selfing or crossing, e.g. hybrid seed (obtained by crossing two inbred parental lines), hybrid plants and plant parts derived there from are encompassed herein, unless otherwise indicated.

A "molecular assay" (or test) refers herein to an assay that indicates (directly or indirectly) the presence or absence of one or more particular IND alleles at one or both IND loci (e.g. at one or both of the IND-A1 or IND-C1 loci). In one embodiment it allows one to determine whether a particular (wild type or mutant) allele is homozygous or heterozygous at the locus in any individual plant.

"Wild type" (also written "wildtype" or "wild-type"), as used herein, refers to a typical form of a plant or a gene as it most commonly occurs in nature. A "wild type plant" refers to a plant with the most common phenotype of such plant in the natural population. A "wild type allele" refers to an allele of a gene required to produce the wild-type phenotype. By contrast, a "mutant plant" refers to a plant with a different rare phenotype of such plant in the natural population or produced by human intervention, e.g. by mutagenesis, and a "mutant allele" refers to an allele of a gene required to produce the mutant phenotype.

As used herein, the term "wild type IND" (e.g. wild type IND-A1 or IND-C1), means a naturally occurring IND allele found within plants, in particular Brassicacea plants, especially *Brassica* plants, which encodes a functional IND protein (e.g. a functional IND-A1 or IND-C1, respectively). In contrast, the term "mutant IND" (e.g. mutant IND-A1 or IND-C1), as used herein, refers to an IND allele, which does not encode a functional IND protein, i.e. an IND allele encoding a non-functional IND protein (e.g. a non-functional IND-A1 or IND-C1, respectively), which, as used herein, refers to an IND protein having no biological activity or a significantly reduced biological activity as compared to the corresponding wild-type functional IND protein, or encoding no IND protein at all. Such a "mutant IND allele" (also called "full knock-out" or "null" allele) is a wild-type IND allele, which comprises one or more mutations in its nucleic acid sequence, whereby the mutation(s) preferably result in a significantly reduced (absolute or relative) amount of functional IND protein in the cell in vivo. As used herein, a "full knock-out IND allele" is a mutant IND allele the presence of which in homozygous state at each IND locus in the plant (e.g. a *Brassica napus* plant with two full knock-out IND-A1 alleles and two full knock-out IND-C1 alleles) results in an increase of pod shatter resistance in that plant which is too high to be still agronomically relevant. Mutant alleles of the IND protein-encoding nucleic acid sequences are designated as "ind" (e.g. ind-a1 or ind-c1, respectively)

herein. Mutant alleles can be either "natural mutant" alleles, which are mutant alleles found in nature (e.g. produced spontaneously without human application of mutagens) or "induced mutant" alleles, which are induced by human intervention, e.g. by mutagenesis.

A "significantly reduced amount of functional IND protein" (e.g. functional IND-A1 or IND-C1 protein) refers to a reduction in the amount of a functional IND protein produced by the cell comprising a mutant IND allele by at least 30%, 40%, 50%, 60%, 70%, 80%, 90%, 95% or 100% (i.e. no functional IND protein is produced by the cell) as compared to the amount of the functional IND protein produced by the cell not comprising the mutant IND allele. This definition encompasses the production of a "non-functional" IND protein (e.g. truncated IND protein) having no biological activity in vivo, the reduction in the absolute amount of the functional IND protein (e.g. no functional IND protein being made due to the mutation in the IND gene), and/or the production of an IND protein with significantly reduced biological activity compared to the activity of a functional wild type IND protein (such as an IND protein in which one or more amino acid residues that are crucial for the biological activity of the encoded IND protein, as exemplified below, are substituted for another amino acid residue). The term "mutant IND protein", as used herein, refers to an IND protein encoded by a mutant IND nucleic acid sequence ("ind allele") whereby the mutation results in a significantly reduced and/or no IND activity in vivo, compared to the activity of the IND protein encoded by a non-mutant, wild type IND sequence ("IND allele").

"Mutagenesis", as used herein, refers to the process in which plant cells (e.g., a plurality of *Brassica* seeds or other parts, such as pollen, etc.) are subjected to a technique which induces mutations in the DNA of the cells, such as contact with a mutagenic agent, such as a chemical substance (such as ethylmethylsulfonate (EMS), ethylnitrosourea (ENU), etc.) or ionizing radiation (neutrons (such as in fast neutron mutagenesis, etc.), alpha rays, gamma rays (such as that supplied by a Cobalt 60 source), X-rays, UV-radiation, etc.), or a combination of two or more of these. Thus, the desired mutagenesis of one or more IND alleles may be accomplished by use of chemical means such as by contact of one or more plant tissues with ethylmethylsulfonate (EMS), ethylnitrosourea, etc., by the use of physical means such as x-ray, etc, or by gamma radiation, such as that supplied by a Cobalt 60 source. While mutations created by irradiation are often large deletions or other gross lesions such as translocations or complex rearrangements, mutations created by chemical mutagens are often more discrete lesions such as point mutations. For example, EMS alkylates guanine bases, which results in base mispairing: an alkylated guanine will pair with a thymine base, resulting primarily in G/C to A/T transitions. Following mutagenesis, *Brassica* plants are regenerated from the treated cells using known techniques. For instance, the resulting *Brassica* seeds may be planted in accordance with conventional growing procedures and following self-pollination seed is formed on the plants. Alternatively, doubled haploid plantlets may be extracted to immediately form homozygous plants, for example as described by Coventry et al. (1988, Manual for Microspore Culture Technique for *Brassica napus*. Dep. Crop Sci. Techn. Bull. OAC Publication 0489. Univ. of Guelph, Guelph, Ontario, Canada). Additional seed that is formed as a result of such self-pollination in the present or a subsequent generation may be harvested and screened for the presence of mutant IND alleles. Several techniques are known to screen for specific mutant alleles, e.g., Delete-agene™ (Delete-a-gene; Li et al., 2001, Plant J 27: 235-242) uses polymerase chain reaction (PCR) assays to screen for deletion mutants generated by fast neutron mutagenesis, TILLING (targeted induced local lesions in genomes; McCallum et al., 2000, Nat Biotechnol 18:455-457) identifies EMS-induced point mutations, etc. Additional techniques to screen for the presence of specific mutant IND alleles are described in the Examples below.

As used herein, the term "non-naturally occurring" when used in reference to a plant, means a plant with a genome that has been modified by man. A transgenic plant, for example, is a non-naturally occurring plant that contains an exogenous nucleic acid molecule, e.g., a chimeric gene comprising a transcribed region which when transcribed yields a biologically active RNA molecule capable of reducing the expression of an endogenous gene, such as an IND gene according to the invention, and, therefore, has been genetically modified by man. In addition, a plant that contains a mutation in an endogenous gene, for example, a mutation in an endogenous IND gene, (e.g. in a regulatory element or in the coding sequence) as a result of an exposure to a mutagenic agent is also considered a non-naturally plant, since it has been genetically modified by man. Furthermore, a plant of a particular species, such as *Brassica napus*, that contains a mutation in an endogenous gene, for example, in an endogenous IND gene, that in nature does not occur in that particular plant species, as a result of, for example, directed breeding processes, such as marker-assisted breeding and selection or introgression, with a plant of the same or another species, such as *Brassica juncea* or rapa, of that plant is also considered a non-naturally occurring plant. In contrast, a plant containing only spontaneous or naturally occurring mutations, i.e. a plant that has not been genetically modified by man, is not a "non-naturally occurring plant" as defined herein and, therefore, is not encompassed within the invention. One skilled in the art understands that, while a non-naturally occurring plant typically has a nucleotide sequence that is altered as compared to a naturally occurring plant, a non-naturally occurring plant also can be genetically modified by man without altering its nucleotide sequence, for example, by modifying its methylation pattern.

The term "ortholog" of a gene or protein refers herein to the homologous gene or protein found in another species, which has the same function as the gene or protein, but is (usually) diverged in sequence from the time point on when the species harboring the genes diverged (i.e. the genes evolved from a common ancestor by speciation). Orthologs of the *Brassica napus* IND genes may thus be identified in other plant species (e.g. *Brassica juncea*, etc.) based on both sequence comparisons (e.g. based on percentages sequence identity over the entire sequence or over specific domains) and/or functional analysis.

A "variety" is used herein in conformity with the UPOV convention and refers to a plant grouping within a single botanical taxon of the lowest known rank, which grouping can be defined by the expression of the characteristics resulting from a given genotype or combination of genotypes, can be distinguished from any other plant grouping by the expression of at least one of the said characteristics and is considered as a unit with regard to its suitability for being propagated unchanged (stable).

The term "comprising" is to be interpreted as specifying the presence of the stated parts, steps or components, but does not exclude the presence of one or more additional parts, steps or components. A plant comprising a certain trait may thus comprise additional traits.

It is understood that when referring to a word in the singular (e.g. plant or root), the plural is also included herein (e.g. a plurality of plants, a plurality of roots). Thus, reference to an element by the indefinite article "a" or "an" does not exclude the possibility that more than one of the element is present, unless the context clearly requires that there be one and only one of the elements. The indefinite article "a" or "an" thus usually means "at least one".

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e., a position in an alignment where a residue is present in one sequence but not in the other, is regarded as a position with non-identical residues. The "optimal alignment" of two sequences is found by aligning the two sequences over the entire length according to the Needleman and Wunsch global alignment algorithm (Needleman and Wunsch, 1970, J Mol. Biol 48(3):443-53) in The European Molecular Biology Open Software Suite (EMBOSS, Rice et al., 2000, Trends in Genetics 16(6): 276-277; see e.g. world wide web at ebi.ac.uk/emboss/align/index.html) using default settings (gap opening penalty=10 (for nucleotides)/10 (for proteins and gap extension penalty=0.5 (for nucleotides)/0.5 (for proteins)). For nucleotides the default scoring matrix used is EDNAFUL and for proteins the default scoring matrix is EBLOSUM62.

"Substantially identical" or "essentially similar", as used herein, refers to sequences, which, when optimally aligned as defined above, share at least a certain minimal percentage of sequence identity (as defined further below).

"Stringent hybridization conditions" can be used to identify nucleotide sequences, which are substantially identical to a given nucleotide sequence. Stringent conditions are sequence dependent and will be different in different circumstances. Generally, stringent conditions are selected to be about 5° C. lower than the thermal melting point ($T_m$) for the specific sequences at a defined ionic strength and pH. The $T_m$ is the temperature (under defined ionic strength and pH) at which 50% of the target sequence hybridizes to a perfectly matched probe. Typically stringent conditions will be chosen in which the salt concentration is about 0.02 molar at pH 7 and the temperature is at least 60° C. Lowering the salt concentration and/or increasing the temperature increases stringency. Stringent conditions for RNA-DNA hybridizations (Northern blots using a probe of e.g. 100 nt) are for example those which include at least one wash in 0.2×SSC at 63° C. for 20 min, or equivalent conditions.

"High stringency conditions" can be provided, for example, by hybridization at 65° C. in an aqueous solution containing 6×SSC (20×SSC contains 3.0 M NaCl, 0.3 M Na-citrate, pH 7.0), 5×Denhardt's (100×Denhardt's contains 2% Ficoll, 2% Polyvinyl pyrollidone, 2% Bovine Serum Albumin), 0.5% sodium dodecyl sulphate (SDS), and 20 µg/ml denatured carrier DNA (single-stranded fish sperm DNA, with an average length of 120-3000 nucleotides) as non-specific competitor. Following hybridization, high stringency washing may be done in several steps, with a final wash (about 30 min) at the hybridization temperature in 0.2-0.1×SSC, 0.1% SDS.

"Moderate stringency conditions" refers to conditions equivalent to hybridization in the above described solution but at about 60-62° C. Moderate stringency washing may be done at the hybridization temperature in 1×SSC, 0.1% SDS.

"Low stringency" refers to conditions equivalent to hybridization in the above described solution at about 50-52° C. Low stringency washing may be done at the hybridization temperature in 2×SSC, 0.1% SDS. See also Sambrook et al. (1989) and Sambrook and Russell (2001).

"Increased harvested yield" or "increased seed or grain yield" refers to the larger amount of seed or grain harvested from a plurality of plants, each comprising mutant IND alleles according to the invention, when compared to the amount of seed or grain harvested from a similar number of isogenic plants without the mutant IND alleles. Yield is typically expressed in volume units of harvested seed per surface units, such as bushels/acre or Kg/ha. The yield increase is typically expressed in percentage, whereby the yield of the reference or control plant is referred to as 100% and the yield of the plants according to the inventions is expressed in % relative to the yield of the control plant. Observed yield increases in *Brassica* plants according to the invention ranged from at least 101% to at least 124% and it is expected that higher yield increases are feasible. Yield increase may also range from 104% to 108% or 105% to 110%.

DETAILED DESCRIPTION

*Brassica napus* (genome AACC, 2n=4x=38), which is an allotetraploid (amphidiploid) species containing essentially two diploid genomes (the A and the C genome) due to its origin from diploid ancestors, comprises two IND genes in its genome. It was found by the inventors that one IND gene is located on the A genome (herein referred to as "IND-A1") and one on the C genome (herein referred to as "IND-C1"). The IND-A1 gene is said to be "homeologous" to the IND-C1 gene, i.e. the "A gene" is found on the A genome and originates from the diploid ancestor *B. rapa* (AA), while the "C gene" is found on the C genome of *B. napus* and originates from the diploid ancestor *B. oleracea* (CC).

As in any diploid genome, two "alleles" can be present in vivo for each IND gene at each IND locus in the genome (one allele being the gene sequence found on one chromosome and the other on the homologous chromosome). The nucleotide sequence of these two alleles may be identical (homozygous plant) or different (heterozygous plant) in any given plant, although the number of different possible alleles existing for each IND gene may be much larger than two in the species population as a whole.

It was moreover found that *Brassica napus* plants, which are homozygous for a full knockout ind allele in only one of the two IND genes, i.e. in IND-A1 or IND-C1, do not show a significant increase in pod shatter resistance compared to *Brassica napus* plants not comprising mutant IND alleles, while in *Brassica napus* plants, which are homozygous for a full knockout ind allele in both IND genes, pod shatter resistance is significantly increased, but the level of pod shatter resistance is too high to maintain an agronomically relevant treshability. By contrast, pod shatter resistance is significantly increased in *Brassica napus* plants comprising three full knockout ind alleles of the two *Brassica napus* IND genes, to a level whereby the plants maintain an agronomically relevant treshability of the pods. It is thought that the presence of three full knockout ind alleles in a *Brassica* plant comprising at least two IND genes, in particular in a *Brassica napus* plant comprising an IND-A1 and an IND-C1 gene, may be required in order to obtain a plant, which shows an increased pod shatter resistance, while maintaining an agronomically relevant treshability of the pods.

Thus in one embodiment of the invention, a *Brassica* plant comprising at least two IND genes, in particular a

*Brassica napus* plant comprising an IND-A1 and an IND-C1 gene, comprising 3 ind alleles is provided herein, whereby the ind alleles result in a significantly reduced amount of functional IND protein of the type encoded by the wild-type equivalent of these mutant alleles and thus an overall significantly reduced amount of the functional IND proteins produced in the plant cells, specifically in the developing seed pods, in vivo.

It is further thought that by combining sufficient copies of specific (mutant) ind alleles with sufficient copies of specific (wild type) IND alleles in one plant, in particular a *Brassica* plant, it is possible to fine tune the amount and/or type of functional IND proteins made, which in turn influences the fruit dehiscence properties of the plant. The absolute and relative amount of the IND proteins can thus be tuned in such a way as to provide plants that produce sufficient IND protein(s) to enable an agronomically relevant treshability of the seed pods, while reducing seed shattering before or during harvest.

Thus in one embodiment of the invention, a plant, in particular a *Brassica* plant, is provided comprising at least one functionally expressed IND allele, which encodes a fully functional IND protein, while the remaining alleles may be (mutant) ind alleles.

In one aspect of the invention a *Brassica* plant comprising at least two IND genes, in particular a *Brassica napus* plant, comprising n-tuple ind alleles of at least 2 different IND genes in that *Brassica* plant, in particular of the IND-A1 and IND-C1 genes, is provided, whereby n≤3 (e.g. n=1, 2, or 3), so that at least one allele produces a functional IND protein.

In a further aspect of the invention an homozygous IND single mutant—(n=2, i.e. homozygous for a mutant allele of one IND gene), and/or an homozygous IND double mutant—(n=4, i.e. homozygous for a mutant allele of two IND genes) plant of a *Brassica* species comprising at least two IND genes, in particular of *Brassica napus*, is provided, whereby the mutant alleles are mutant alleles of 2 different IND genes in that *Brassica* plant, in particular of the IND-A1 and/or IND-C1 genes. Such mutant plants may, according to this invention, be used for breeding purposes. Thus in one embodiment of the invention, an homozygous IND single mutant *Brassica napus* plant is provided herein, wherein the genotype of the plant can be described as ind-a1/ind-a1, IND-C1/IND-C1, or IND-A1/IND-A1, ind-c1/ind-c1. In another embodiment of the invention, an homozygous IND double mutant *Brassica napus* plant is provided herein, wherein the genotype of the plant can be described as ind-a1/ind-a1, ind-c1/ind-c1.

In a further aspect of the invention the homozygous IND single (n=2) mutant plant of the *Brassica* species comprising at least two IND genes, in particular of *Brassica napus*, comprises a further mutant IND allele, wherein the mutant plant is heterozygous for the additional mutant IND allele (i.e., n=3), and wherein the mutant allele is a mutant allele of the remaining wild-type IND gene in that *Brassica* plant, in particular of the IND-A1 or IND-C1 gene. Thus in a further embodiment of the invention, an homozygous IND single mutant *Brassica napus* plant comprising one further mutant IND allele is provided herein, wherein the genotype of the plant can be described as ind-a1/ind-a1, IND-C1/ind-c1, or IND-A1/ind-a1, ind-c1/ind-c1.

Further provided herein are nucleic acid sequences of wild type and mutant IND genes/alleles from *Brassica* species, as well as the wild type and mutant IND proteins. Also provided are methods of generating and combining mutant and wild type IND alleles in *Brassica* plants, as well as *Brassica* plants and plant parts comprising specific combinations of wild type and mutant IND alleles in their genome, whereby seed shattering is reduced in these plants. The use of these plants for transferring mutant IND alleles to other plants is also an embodiment of the invention, as are the plant products of any of the plants described. In addition kits and methods for marker assisted selection (MAS) for combining or detecting IND genes and/or alleles are provided. Each of the embodiments of the invention is described in detail herein below.

The *Brassica* plants described herein which exhibit reduced or delayed seed shattering have an increase in the yield of harvested seed. However, it was observed, unexpectedly, that the harvested seed yield from *Brassica* plants comprising only two mutant IND alleles in homozygous state, i.e. wherein the genotype of the plant can be described as ind-a1/ind-a1, IND-C1/IND-C1, or IND-A1/IND-A1, ind-c1/ind-c1 was also significantly increased, when compared to isogenic *Brassica* plants not comprising the mutant IND alleles, despite the absence of an observable reduced or delayed seed shatter phenotype in the *Brassica* plants comprising the mutant IND alleles. The invention thus also provides *Brassica* plants comprising at least two IND genes, wherein at least two alleles produce a functional IND protein, which plants have a higher seed yield. It will be clear that the two mutant alleles at the IND-A locus or at the IND-C locus may be the same mutant allele or a different mutant allele.

Nucleic Acid Sequences According to the Invention

Provided are both wild type IND nucleic acid sequences encoding functional IND proteins and mutant ind nucleic acid sequences (comprising one or more mutations, preferably mutations which result in no or a significantly reduced biological activity of the encoded IND protein or in no IND protein being produced) of IND genes from Brassicaceae, particularly from *Brassica* species, especially from *Brassica napus*, but also from other *Brassica* crop species. For example, *Brassica* species comprising an A and/or a C genome may comprise different alleles of IND-A or IND-C genes, which can be identified and combined in a single plant according to the invention. In addition, mutagenesis methods can be used to generate mutations in wild type IND alleles, thereby generating mutant ind alleles for use according to the invention. Because specific IND alleles are preferably combined in a plant by crossing and selection, in one embodiment the IND and/or ind nucleic acid sequences are provided within a plant (i.e. endogenously), e.g. a *Brassica* plant, preferably a *Brassica* plant which can be crossed with *Brassica napus* or which can be used to make a "synthetic" *Brassica napus* plant. Hybridization between different *Brassica* species is described in the art, e.g., as referred to in Snowdon (2007, Chromosome research 15: 85-95). Interspecific hybridization can, for example, be used to transfer genes from, e.g., the C genome in *B. napus* (AACC) to the C genome in *B. carinata* (BBCC), or even from, e.g., the C genome in *B. napus* (AACC) to the B genome in *B. juncea* (AABB) (by the sporadic event of illegitimate recombination between their C and B genomes). "Resynthesized" or "synthetic" *Brassica napus* lines can be produced by crossing the original ancestors, *B. oleracea* (CC) and *B. rapa* (AA). Interspecific, and also intergeneric, incompatibility barriers can be successfully overcome in crosses between *Brassica* crop species and their relatives, e.g., by embryo rescue techniques or protoplast fusion (see e.g. Snowdon, above).

However, isolated IND and ind nucleic acid sequences (e.g. isolated from the plant by cloning or made synthetically by DNA synthesis), as well as variants thereof and fragments of any of these are also provided herein, as these can be used to determine which sequence is present endogenously in a plant or plant part, whether the sequence encodes a functional, a non-functional or no protein (e.g. by expression in a recombinant host cell as described below) and for selection and transfer of specific alleles from one plant into another, in order to generate a plant having the desired combination of functional and mutant alleles.

Nucleic acid sequences of IND-A1 and IND-C1 have been isolated from *Brassica napus* as depicted in the sequence listing. The wild type IND sequences are depicted, while the mutant ind sequences of these sequences, and of sequences essentially similar to these, are described herein below and in the Examples, with reference to the wild type IND sequences. The genomic IND protein-encoding DNA from *Brassica napus* does not comprise any introns.

"IND-A1 nucleic acid sequences" or "IND-A1 variant nucleic acid sequences" according to the invention are nucleic acid sequences encoding an amino acid sequence having at least 75%, at least 80%, at least 85%, at least 90%, at least 95%, 98%, 99% or 100% sequence identity with SEQ ID NO: 2 or nucleic acid sequences having at least 80%, at least 85%, at least 90%, at least 95%, 96%, 97%, 98%, 99% or 100% sequence identity with SEQ ID NO: 1 or SEQ ID NO: 5. These nucleic acid sequences may also be referred to as being "essentially similar" or "essentially identical" to the IND sequences provided in the sequence listing.

"IND-C1 nucleic acid sequences" or "IND-C1 variant nucleic acid sequences" according to the invention are nucleic acid sequences encoding an amino acid sequence having at least 75%, at least 80%, at least 85%, at least 90%, at least 95%, 98%, 99% or 100% sequence identity with SEQ ID NO: 4 (IND-C1-long) or with SEQ ID NO: 4 from the amino acid at position 16 to the amino acid at position 210 (IND-C1-short) or nucleic acid sequences having at least 80%, at least 85%, at least 90%, at least 95%, 96%, 97%, 98%, 99% or 100% sequence identity with SEQ ID NO: 3 (IND-C1-long), with SEQ ID NO:3 from the nucleotide at position 46 to the nucleotide at position 633 (IND-C1-short) or with SEQ ID NO: 7. These nucleic acid sequences may also be referred to as being "essentially similar" or "essentially identical" to the IND sequences provided in the sequence listing.

Thus the invention provides both nucleic acid sequences encoding wild type, functional IND-A1 and IND-C1 proteins, including variants and fragments thereof (as defined further below), as well as mutant nucleic acid sequences of any of these, whereby the mutation in the nucleic acid sequence preferably results in one or more amino acids being inserted, deleted or substituted in comparison to the wild type IND protein. Preferably the mutation(s) in the nucleic acid sequence result in one or more amino acid changes (i.e. in relation to the wild type amino acid sequence one or more amino acids are inserted, deleted and/or substituted) whereby the biological activity of the ND protein is significantly reduced or completely abolished. A significant reduction in or complete abolishment of the biological activity of the IND protein refers herein to a reduction in or abolishment of the DNA binding activity, the dimerization capacity and/or transcriptional regulating activity of the IND protein, such that the pod shatter resistance of a plant expressing the mutant IND protein is increased as compared to a plant expressing the corresponding wild type IND protein.

To determine the functionality of a specific IND allele/protein in plants, particularly in *Brassica* plants, the level of resistance to pod shattering in the plants can be determined by performing macroscopical, microscopical and histological assays on fruits and flowers of the plants comprising the specific IND allele/protein and of corresponding wild type plants analogous to the assays performed on *Arabidopsis* fruits and flowers as described by Liljegren et al. (2004, supra) or as described in the Examples below. Briefly, changes in pod shatter resistance can be evaluated and/or measured, e.g., by macroscopical tests, such as inspection of the seed pods with naked eye to evaluate, e.g., the presence or absence of the valve margins, the length of the beak of the pods, etc.; a Manual Impact Test (MIT) to compare the level of pod shatter resistance between different mutant IND lines and corresponding wild type lines by evaluating the ease of pod opening upon gently twisting the pods; a Random Impact Test (RIT) to compare the treshability of seed pods from plants from different mutant IND lines and corresponding wild type lines, respectively, by measuring the half-life of pod samples of these lines; and/or by microscopic tests to examine, e.g., whether and how cells at the valve margin and the dehiscence zone of seed pods are affected by mutations in IND. Once the dimerization partner of the IND protein (e.g., the IND protein itself in case its functioning depends on the formation of an homodimer or another protein in case its functioning depends on the formation of an heterodimer) and/or the gene(s) the transcription of which is regulated by the IND protein are identified and characterized, the functionality of a specific IND allele/protein can alternatively be evaluated by recombinant DNA techniques as known in the art, e.g., by co-expressing both partners of the dimer in a host cell (e.g. a bacterium, such as *E. coli*) and evaluating if dimers can still be formed, if the dimers can still bind to the bHLH binding site of the regulated gene(s), and/or if the transcription of these gene(s) is still regulated by this binding.

Both endogenous and isolated nucleic acid sequences are provided herein. Also provided are fragments of the IND sequences and IND variant nucleic acid sequences defined above, for use as primers or probes and as components of kits according to another aspect of the invention (see further below). A "fragment" of a IND or ind nucleic acid sequence or variant thereof (as defined) may be of various lengths, such as at least 10, 12, 15, 18, 20, 50, 100, 200, 500, 600 contiguous nucleotides of the IND or ind sequence (or of the variant sequence).

Nucleic Acid Sequences Encoding Functional IND Proteins

The nucleic acid sequences depicted in the sequence listing encode wild type, functional IND proteins from *Brassica napus*. Thus, these sequences are endogenous to the *Brassica napus* plants from which they were isolated. Other *Brassica* crop species, varieties, breeding lines or wild accessions may be screened for other IND alleles, encoding the same IND proteins or variants thereof. For example, nucleic acid hybridization techniques (e.g. Southern blot analysis, using for example stringent hybridization conditions) or PCR-based techniques may be used to identify IND alleles endogenous to other *Brassica* plants, such as various *Brassica napus* varieties, lines or accessions, but also *Brassica juncea* (especially IND alleles on the A-genome), *Brassica carinata* (especially IND alleles on the C-genome) and *Brassica rapa* (A-genome) and *Brassica oleracea* (C-genome) plants, organs and tissues can be screened for other wild type IND alleles. To screen such plants, plant organs or tissues for the presence of IND alleles, the IND nucleic acid sequences provided in the sequence listing, or variants or fragments of any of these, may be used. For example whole sequences or fragments may be used as probes or primers. For example specific or degenerate primers may be used to amplify nucleic acid sequences encoding IND proteins from the genomic DNA of the plant, plant organ or tissue. These IND nucleic acid sequences may be isolated and sequenced using standard molecular biology techniques. Bioinformatics analysis may then be used to characterize the allele(s), for example in order to determine which IND allele the sequence corresponds to and which IND protein or protein variant is encoded by the sequence.

Whether a nucleic acid sequence encodes a functional IND protein can be analyzed by recombinant DNA techniques as known in the art, e.g., by a genetic complementation test using, e.g., an *Arabidopsis* plant, which is homozygous for a full knock-out ind mutant allele or a *Brassica napus* plant, which is homozygous for a full knock-out ind mutant allele of both the IND-A1 and IND-C1 gene.

In addition, it is understood that IND nucleic acid sequences and variants thereof (or fragments of any of these) may be identified in silico, by screening nucleic acid databases for essentially similar sequences. Likewise, a nucleic acid sequence may be synthesized chemically. Fragments of nucleic acid molecules according to the invention are also provided, which are described further below. Fragments include nucleic acid sequences encoding only the bHLH domain, or smaller fragments comprising part of the bHLH domain, such as the basic domain or the HLH domain, etc.

Nucleic Acid Sequences Encoding Mutant IND Proteins

Nucleic acid sequences comprising one or more nucleotide deletions, insertions or substitutions relative to the wild type nucleic acid sequences are another embodiment of the invention, as are fragments of such mutant nucleic acid molecules. Such mutant nucleic acid sequences (referred to as ind sequences) can be generated and/or identified using various known methods, as described further below. Again, such nucleic acid molecules are provided both in endogenous form and in isolated form. In one embodiment, the mutation(s) result in one or more changes (deletions, insertions and/or substitutions) in the amino acid sequence of the encoded IND protein (i.e. it is not a "silent mutation"). In another embodiment, the mutation(s) in the nucleic acid sequence result in a significantly reduced or completely abolished biological activity of the encoded IND protein relative to the wild type protein.

The nucleic acid molecules may, thus, comprise one or more mutations, such as:

(a) a "missense mutation", which is a change in the nucleic acid sequence that results in the substitution of an amino acid for another amino acid;

(b) a "nonsense mutation" or "STOP codon mutation", which is a change in the nucleic acid sequence that results in the introduction of a premature STOP codon and thus the termination of translation (resulting in a truncated protein); plant genes contain the translation stop codons "TGA" (UGA in RNA), "TAA" (UAA in RNA) and "TAG" (UAG in RNA); thus any nucleotide substitution, insertion, deletion which results in one of these codons to be in the mature mRNA being translated (in the reading frame) will terminate translation.

(c) an "insertion mutation" of one or more amino acids, due to one or more codons having been added in the coding sequence of the nucleic acid;

(d) a "deletion mutation" of one or more amino acids, due to one or more codons having been deleted in the coding sequence of the nucleic acid;

(e) a "frameshift mutation", resulting in the nucleic acid sequence being translated in a different frame downstream of the mutation. A frameshift mutation can have various causes, such as the insertion, deletion or duplication of one or more nucleotides.

As already mentioned, it is desired that the mutation(s) in the nucleic acid sequence preferably result in a mutant protein comprising significantly reduced or no biological activity in vivo or in the production of no protein Basically, any mutation which results in a protein comprising at least one amino acid insertion, deletion and/or substitution relative to the wild type protein can lead to significantly reduced or no biological activity. It is, however, understood that mutations in certain parts of the protein are more likely to result in a reduced function of the mutant IND protein, such as mutations leading to truncated proteins, whereby significant portions of the functional domains, such as the DNA binding domain ('b'), the dimerization domain ('HLH') and/or transcription regulating domains, are lacking.

According to the *Arabidopsis* Information Resource (TAIR) database, (which can be found on the world wide web at arabidopsis.org/) the *Arabidopsis* INDEHISCENT protein (locus At4g00120.1; SEQ ID NO: 10) is 198 amino acids in length and comprises a "basic helix-loop-helix (bHLH) dimerisation" domain located between the amino acids at position 121 and 168 (pfam domain PF00010), between the amino acids at position 124 and 173 (smart domain SM00353), or between the amino acids at position 112 and 168 (prosite domain PS50888) and an "helix-loop-helix (HLH) DNA binding" domain between the amino acids at position 114 and 196 or 198 (superfram domain G3D.4.10.280.10 or SSF47459, respectively) of SEQ ID NO: 10.

The IND-A1 protein of *Brassica* described herein is about 185 amino acids in length (SEQ ID NO:2) and the IND-C1 protein about 195 (SEQ ID NO:4 from the amino acid at position 16 to 210) or 210 (SEQ ID NO:4) amino acids and they comprise the "basic bHLH dimerisation" domain located between the amino acids at position 120 and 167 in SEQ ID NO: 2 and position 133 and 180 in SEQ ID NO: 4 (pfam domain PF00010), between the amino acids at position 123 and 172 in SEQ ID NO: 2 and position 136 and 185 in SEQ ID NO: 4 (smart domain SM00353), or between the amino acids at position 111 and 167 in SEQ ID NO: 2 and position 124 and 180 in SEQ ID NO: 4 (prosite domain PS50888) and the "HLH DNA binding" domain between the amino acids at position 127 and 208 or 210 in SEQ ID NO: 4 (superfam domain G3D.4.10.280.10 or SSF47459, respectively), as determined by optimally aligning the *Brassica* and *Arabidopsis* IND proteins and based on the annotation information in the TAIR database.

As described by Heim et al. (2003, Mol Biol Evol 20, 735-747), the consensus bHLH domain sequence of 133 *Arabidopsis* bHLH transcription factor genes consists of approximately 56 amino acids (Heim et al., FIG. 1; corresponding to position 119-174 in SEQ ID NO: 10). This bipartite domain comprises (1) the basic region, located at the N-terminal end of the domain, which is involved in DNA binding and consists of about 13 amino acids with a high number of basic residues ("b"; corresponding to position 119-131 in SEQ ID NO: 10), and (2) the helix-loop-helix region, located at the C-terminal end, which functions as a dimerization domain and is constituted of about 43 mainly hydrophobic amino acid residues (corresponding to position 132-174 in SEQ ID NO: 10) that form two amphipathic alpha-helices of about 15 amino acids ("H1"; corresponding to position 132-146 in SEQ ID NO: 10) and 22 amino acids ("H2"; corresponding to position 153-174 in SEQ ID NO: 10), respectively, separated by a loop region of about 6 and up to about 14 amino acids ("L"; corresponding to position 147-152 in SEQ ID NO: 10), which is the most divergent region of the bHLH domain in terms of size and amino acid composition. The two alpha-helices promote dimerization, allowing the formation of homo- and/or heterodimers between different family members (Toledo-Ortiz et al., 2003, Plant Cell 15: 1749-1770). While the bHLH domain is evolutionarily conserved (Atchley and Fitch, 1997, PNAS 94: 5172-5176), there is little sequence similarity between different bHLH family members beyond this domain (Morgenstern and Atchley, 1999, Mol Biol Evol 16: 1654-1663).

Within those bHLH proteins with proven ability to bind DNA, the amino acids at position 5, 9, and 13 of the consensus bHLH domain sequence defined by Heim et al. (supra) are the most critical. For non-plant bHLH proteins, it was shown that a His (H) residue at position 5, a Glu (E) residue at position 9 and an Arg (R) residue at position 13 (all within the basic region) were critical for DNA binding (Brownlie et al., 1997, Structure 5, 509-520; Atchley et al., 1999, J Mol Evol 48, 501-516; Ledent and Vervoort, 2001, Genome Res 11, 754-770). However, some plant proteins have a variation of the H-E-R configuration. For example, according to Heim et al. (supra), the 5-9-13 motif of the bHLH domain encoded by *Arabidopsis* gene At4g00120 (corresponding to the *Arabidopsis* IND gene represented in SEQ ID NO: 9) consists of amino acid residues Gln (O), Ala (A) and Arg (R), respectively (corresponding to positions 123, 127 and 131, respectively, in SEQ ID NO: 10) (FIG. 4 of Heim et al. (supra). Such plant proteins, which have a variation of the H-E-R configuration, may further contain helix-breaking prolines in the basic region, e.g. members of Group VIII and X, characteristics that may interfere with affinity for DNA. These variations may enable these proteins to act as negative regulators, retaining the ability to dimerize with other bHLH proteins but lacking the ability to bind DNA. While the 5-9-13 motif is important for DNA binding, the DNA backbone is contacted by the basic residues at positions 10 and 12 (both Arg (R) in the consensus bHLH domain sequence), which are also conserved in the majority of plant proteins (corresponding to positions 128 and 130 in SEQ ID NO: 10).

Furthermore, Heim et al. (supra) describe that the highly conserved hydrophobic residues at position 16, 20, 23, 27 in helix1 (corresponding to position 134, 138, 141, 145 in SEQ ID NO: 10) and at position 36, 39, 43, 49, 53, and 56 in helix2 (corresponding to position 154, 157, 161, 167, 171, 174 in SEQ ID NO: 10), for example, the leucine residue at position 23 within the helix1 domain (corresponding to position 141 in SEQ ID NO: 10) and the conserved hydrophobic residues in helix 2 that are located to one side of the helix, are necessary for dimerization or stabilization of dimer formation.

Finally, Heim et al. (supra; FIG. 4) indicate conserved amino acid sequences outside the DNA binding domain, some of which are thought to act as activation domain or be important for interaction with other modules of the transcription complex or to be targets of signal transduction chains.

TABLE 1

IND proteins - amino acids (AA) regions and positions

|  |  | AtIND1 (SEQ ID NO: 10) | AtIND1 (SEQ ID NO: 9) | BnIND-A1 (SEQ ID NO: 2/6) | BnIND-C1a/b (SEQ ID 4/8 from 16-210/ SEQ ID 4/8) |
|---|---|---|---|---|---|
| Coding region | TAIR: | 1-198 (198 AA) | 1-594 | 1-185 (185 AA) | 16-210/1-210 (195/210 AA) |
|  | PF00010 | 121-168 | 361-504 | 120-167 | 133-180 |
|  | SM00353 | 124-173 | 370-519 | 123-172 | 136-185 |
|  | PS50888 | 112-168 | 334-504 | 111-167 | 124-180 |
|  | G3D.4.10.280.10 | 114-196 | 340-588 | — | 127-208 |
|  | SSF47459 | 114-198 | 340-594 | — | 127-210 |
|  | Liljegren et al. | 30-198 (169 AA) | 88-594 |  |  |
| bHLH: | Heim et al. | 119-174 | 355-523 | 118-173 | 131-186 |
|  | Toledo-Ortiz et al. | 115-167 | 343-501 | 114-166 | 127-179 |
|  | Liljegren et al. | 119-167 | 355-501 | 118-166 | 131-179 |
| b | Heim et al. | 119-131 | 355-393 | 118-132 | 131-145 |
|  | Toledo-Ortiz et al. | 115-131 | 343-393 | 114-132 | 127-145 |
|  | Liljegren et al. | 119-131 | 355-393 | 118-132 | 131-145 |
| H1 | Heim et al. | 132-146 | 394-438 | 133-145 | 146-158 |
|  | Toledo-Ortiz et al. | 132-146 | 394-438 | 133-145 | 146-158 |
|  | Liljegren et al. | 132-145 | 394-435 | 133-144 | 146-157 |
| L | Heim et al. | 147-152 | 439-456 | 146-151 | 159-164 |
|  | Toledo-Ortiz et al. | 147-152 | 439-456 | 146-151 | 159-164 |
|  | Liljegren et al. | 146-152 | 436-456 | 145-151 | 158-164 |
| H2 | Heim et al. | 153-174 | 457-523 | 152-173 | 165-186 |
|  | Toledo-Ortiz et al. | 153-167 | 457-501 | 152-166 | 165-179 |
|  | Liljegren et al. | 153-167 | 457-501 | 152-166 | 165-179 |
| Conserved AA | N ($1^T$) | 115 | 343-345 | 114 | 127 |
|  | V ($2^T$) | 116 | 346-348 | 115 | 128 |
|  | Q ($5^H$) | 123 | 367-379 | 122 | 135 |
|  | A ($9^H$-$13^T$) | 127 | 379-381 | 126 | 139 |
|  | R ($10^H$-$14^T$) | 128 | 382-384 | 127 | 140 |
|  | R ($12^H$-$16^T$) | 130 | 388-390 | 129 | 142 |
|  | R ($13^H$) | 131 | 391-393 | 130 | 143 |
|  | I ($16^H$-$20^T$) | 134 | 400-403 | 133 | 146 |
|  | S ($21^T$) | 135 | 404-406 | 134 | 147 |
|  | I ($20^H$-$24^T$) | 138 | 412-414 | 137 | 150 |
|  | L ($23^H$-$27^T$) | 141 | 421-423 | 140 | 153 |
|  | K ($28^T$) | 142 | 424-426 | 141 | 154 |

TABLE 1-continued

IND proteins - amino acids (AA) regions and positions

|  | | AtIND1 (SEQ ID NO: 10) | AtIND1 (SEQ ID NO: 9) | BnIND-A1 (SEQ ID NO: 2/6) | BnIND-C1a/b (SEQ ID 4/8 from 16-210/ SEQ ID 4/8) |
|---|---|---|---|---|---|
| | V (27[H]) | 145 | 433-435 | 144 | 157 |
| | K (39[T]) | 150 | 448-450 | 149 | 162 |
| | T (42[T]) | 153 | 460-463 | 152 | 165 |
| | A (36[H]) | 154 | 460-462 | 153 | 166 |
| | M (45[T]) | 156 | 466-468 | 155 | 168 |
| | L (39[H]-46[T]) | 157 | 469-471 | 156 | 169 |
| | A (49[T]) | 160 | 478-480 | 159 | 172 |
| | I (43[H]-50[T]) | 161 | 481-483 | 160 | 173 |
| | Y (52[T]) | 163 | 487-489 | 162 | 175 |
| | T (53[T]) | 164 | 490-492 | 163 | 176 |
| | L (49[H]-56[T]) | 167 | 499-501 | 166 | 179 |
| | V (53[H]) | 171 | 511-513 | 170 | 183 |
| | L (56[H]) | 174 | 580-582 | 173 (A) | 186 |
| At ind | ind-5 (W13 > STOP)[L] | 42 | 124-126 | 25 | 41 |
| | ind-2 (A26 > FS)[L] | 55 | 163-165 | — | — |
| | ind-6[W] | Insertion after 61 | Insertion after 185 | — | — |
| | ind-4 (Q63 > STOP)[L] | 92 | 274-276 | 91 | 104 |
| | ind-3 (R99 > H)[L] | 128 | 382-384 | 127 | 140 |
| | ind-1 (L112 > F)[L] | 141 | 421-423 | 140 | 153 |

Heim et al.,
[H]Heim et al., 2003, Mol Biol Evol 20, 735-747; Toledo-Ortiz et al.,
[T]Toledo-Ortiz et al., 2003, Plant Cell 15: 1749-1770; Liljegren et al.,
[L]Liljegren et al., 2004, Cell, 116, 843-853;
[W]Wu et al., 2006, Planta 224, 971-979.

Similarly, as described by Toledo-Ortiz et al. (2003, Plant Cell 15: 1749-1770; FIG. 1), the bHLH domain of the *Arabidopsis* bHLH transcription factor family consists of approximately 56 amino acids (Toledo-Ortiz et al.; corresponding to position 115-167 in SEQ ID NO: 10). This bipartite domain comprises (1) the basic region, located at the N-terminal end of the domain, which is involved in DNA binding and consists of about 17 amino acids with a high number of basic residues ("b"; corresponding to position 115-131 in SEQ ID NO: 10), and (2) the HLH region, located at the C-terminal end, which functions as a dimerization domain and is constituted of about 39 mainly hydrophobic amino acid residues (corresponding to position 132-167 in SEQ ID NO: 10) that form two amphipathic alpha-helices of about 15 amino acids ("H1" corresponding to position 132-146 in SEQ ID NO: 10, and "H2" corresponding to position 152-167 in SEQ ID NO: 10) separated by a loop region of about 9 amino acids ("L"; corresponding to position 147-151 in SEQ ID NO: 10), which is the most divergent region of the bHLH domain in terms of size and amino acid composition.

Based on patterns of sequence conservation, a hypothetical consensus motif, representing the most conserved amino acids in the bHLH region, including 19 amino acids dispersed across the bHLH domain (18 from b, H1 and H2; 1 from L) was generated by Atchley et al. (1999). The identified conserved amino acids correspond to the amino acids at position 1, 2, 13, 14, 16 (in b); 20, 21, 24, 27, 28 (in H1); 39 (in L); 42, 45, 46, 49, 50, 52, 53, and 56 (in H2) of the *Arabidopsis* bHLH domain defined by Toledo-Ortiz et al. (2003, supra), which correspond to the amino acids at position 115, 116, 127, 128, 130 (in b); 134, 135, 138, 141, 142 (in H1); 150 (in L); 153, 156, 157, 160, 161, 163, 164, and 167 (in H2) of SEQ ID NO: 10.

According to Liljegren et al. (2004, Cell, 116, 843-853), the bHLH domain of the *Arabidopsis* IND gene comprises a basic region of 13 amino acids (SEQ ID NO: 10 from the amino acid at position 119 to 131) and two alpha-helices of 14 and 15 amino acids, respectively, (SEQ ID NO: 10 from the amino acid at position 132-145 and from the amino acid at position 153 to 167, respectively) separated by a variable loop region of 7 amino acids (SEQ ID NO: 10 from the amino acid at position 146 to 152).

Optimal alignment of the *Arabidopsis* IND nucleic acid (SEQ ID NO: 9) and amino acid (SEQ ID NO: 10) sequences with IND nucleic acid sequences, in particular the *Brassica* IND nucleic acid (SEQ ID NO: 1 and 3) and amino acid (SEQ ID NO: 2 and 4) sequences of the present invention, allows to determine the positions of the corresponding conserved domains and amino acids in these *Brassica* sequences (see Table 1 for the *Brassica* IND sequences of SEQ ID NO: 1 to 4).

Thus in one embodiment, nucleic acid sequences comprising one or more of any of the types of mutations described above are provided. In another embodiment, ind sequences comprising one or more stop codon (nonsense) mutations, one or more missense mutations and/or one or more frameshift mutations are provided. Any of the above mutant nucleic acid sequences are provided per se (in isolated form), as are plants and plant parts comprising such sequences endogenously. In the tables herein below the most preferred ind alleles are described and seed deposits of *Brassica napus* seeds comprising one or more ind alleles have been deposited as indicated.

A nonsense mutation in an IND allele, as used herein, is a mutation in an IND allele whereby one or more translation stop codons are introduced into the coding DNA and the corresponding mRNA sequence of the corresponding wild type IND allele. Translation stop codons are TGA (UGA in the mRNA), TAA (UAA) and TAG (UAG). Thus, any mutation (deletion, insertion or substitution) that leads to the generation of an in-frame stop codon in the coding sequence will result in termination of translation and truncation of the amino acid chain. In one embodiment, a mutant IND allele comprising a nonsense mutation is an IND allele wherein an in-frame stop codon is introduced in the IND codon sequence by a single nucleotide substitution, such as the mutation of CAG to TAG, TGG to TAG, TGG to TGA, or CAA to TAA. In another embodiment, a mutant IND allele comprising a nonsense mutation is an IND allele wherein an in-frame stop codon is introduced in the IND codon sequence by double nucleotide substitutions, such as the mutation of CAG to TAA, TGG to TAA, or CGG to TAG or TGA. In yet another embodiment, a mutant IND allele comprising a nonsense mutation is an IND allele wherein an in-frame stop codon is introduced in the IND codon sequence by triple nucleotide substitutions, such as the mutation of CGG to TAA. The truncated protein lacks the amino acids encoded by the coding DNA downstream of the mutation (i.e. the C-terminal part of the IND protein) and maintains the amino acids encoded by the coding DNA upstream of the mutation (i.e. the N-terminal part of the IND protein). In one embodiment, a mutant IND allele comprising a nonsense mutation is an IND allele wherein the nonsense mutation is present anywhere in front of the conserved Leu residue of the H2 domain (at position 56 in the consensus bHLH domain sequence as described by Heim et al., 2003, see above), so that at least the conserved Leu residue is lacking. The more truncated the mutant IND protein is in comparison to the wild type IND protein, the more the truncation may result in a significantly reduced or no activity of the IND protein. Thus in another embodiment, a mutant IND allele comprising a nonsense mutation which results in a truncated protein of less than about 170 amino acids (lacking the conserved Leu), less than about 150 amino acids (lacking the H2 domain), less than about 145 amino acids (lacking the L and H2 domains), less than about 130 amino acids (lacking the HLH domain), less than about 115 amino acids (lacking the bHLH domain), or even less amino acids in length, such as mutant IND alleles corresponding to the *Arabidopsis* ind-4 or ind-5 (Liljegren et al., 2004, supra) alleles are provided (see Table 1).

The Tables herein below describe a range of possible nonsense mutations in the *Brassica napus* IND sequences provided herein:

TABLE 2a

Potential STOP codon mutations in IND-A1 (SEQ ID NO: 1)

| Amino acid position | Nucleotide position | Wild type → mutant codon | Wild type → mutant amino acid |
|---|---|---|---|
| 25 | 74 | tgg → tag | TRP → STOP |
|  | 75 | tgg → tga | TRP → STOP |
|  | 74 + 75 | tgg → taa | TRP → STOP |
| 57 | 169 | cag → tag | GLN → STOP |
|  | 169 + 171 | cag → taa | GLN → STOP |
| 91 | 271 | caa → taa | GLN → STOP |
| 98 | 292 | cag → tag | GLN → STOP |
|  | 292 + 294 | cag → taa | GLN → STOP |
| 122 | 364 | cag → tag | GLN → STOP(1) |
|  | 364 + 366 | cag → taa | GLN → STOP |
| 128 | 382 + 383 | cgg → tag | ARG → STOP |
|  | 382 + 384 | cgg → tga | ARG → STOP |
|  | 382 + 383 + 384 | cgg → taa | ARG → STOP |
| 138 | 412 + 413 | cgg → tag | ARG → STOP |
|  | 412 + 414 | cgg → tga | ARG → STOP |
|  | 412 + 413 + 414 | cgg → taa | ARG → STOP |

TABLE 2a-continued

Potential STOP codon mutations in IND-A1 (SEQ ID NO: 1)

| Amino acid position | Nucleotide position | Wild type → mutant codon | Wild type → mutant amino acid |
|---|---|---|---|
| 168 | 502 + 503 | cgg → tag | ARG → STOP |
|  | 502 + 504 | cgg → tga | ARG → STOP |
|  | 502 + 503 + 504 | cgg → taa | ARG → STOP |
| 169 | 505 | cag → tag | GLN → STOP |
|  | 505 + 507 | cag → taa | GLN → STOP |
| 181 | 542 | tgg → tag | TRP → STOP |
|  | 543 | tgg → tga | TRP → STOP |
|  | 542 + 543 | tgg → taa | TRP → STOP |

(1) seeds comprising a mutant IND-A1 allele comprising this non-sense mutation (called hereinafter ind-a1-EMS01) have been deposited at the American Type Culture Collection (ATCC, 10801 University Boulevard, Manassas, VA 20110-2209, US) on Nov. 20, 2007, under accession number PTA-8796

TABLE 2b

Potential STOP codon mutations in IND-C1 (SEQ ID NO: 3)

| Amino acid position | Nucleotide position | Wild type → mutant codon | Wild type → mutant amino acid |
|---|---|---|---|
| 41 | 122 | tgg → tag | TRP → STOP |
|  | 123 | tgg → tga | TRP → STOP |
|  | 122 + 123 | tgg → taa | TRP → STOP |
| 50 | 148 | caa → taa | GLN → STOP(2) |
| 73 | 271 | cag → tag | GLN → STOP |
|  | 271 + 272 | cag → taa | GLN → STOP |
| 104 | 310 | caa → taa | GLN → STOP |
| 111 | 331 | cag → tag | GLN → STOP |
|  | 331 + 333 | cag → taa | GLN → STOP |
| 135 | 403 | cag → tag | GLN → STOP(3) |
|  | 403 + 405 | cag → taa | GLN → STOP |
| 141 | 421 + 422 | cgg → tag | ARG → STOP |
|  | 421 + 423 | cgg → tga | ARG → STOP |
|  | 421 + 422 + 423 | cgg → taa | ARG → STOP |
| 151 | 451 + 452 | cgg → tag | ARG → STOP |
|  | 451 + 453 | cgg → tga | ARG → STOP |
|  | 451 + 452 + 453 | cgg → taa | ARG → STOP |
| 181 | 541 + 542 | cgg → tag | ARG → STOP |
|  | 541 + 543 | cgg → tga | ARG → STOP |
|  | 541 + 542 + 543 | cgg → taa | ARG → STOP |
| 182 | 544 | cag → tag | GLN → STOP |
|  | 544 + 546 | cag → taa | GLN → STOP |
| 187 | 559 | cag → tag | GLN → STOP |
|  | 559 + 561 | cag → taa | GLN → STOP |
| 191 | 571 | cag → tag | GLN → STOP |
|  | 571 + 573 | cag → taa | GLN → STOP |

(2) seeds comprising a mutant IND-C1 allele comprising this non-sense mutation (called hereinafter ind-c1-EMS01) have been deposited at the ATCC on Nov. 20, 2007, under accession number PTA-8796
(3) seeds comprising a mutant IND-C1 allele comprising this non-sense mutation (called hereinafter ind-c1-EMS03) have been deposited at the ATCC on Nov. 20, 2007, under accession number PTA-8795

Obviously, mutations are not limited to the ones shown in the above tables and it is understood that analogous STOP mutations may be present in ind alleles other than those depicted in the sequence listing and referred to in the tables above.

A missense mutation in an IND allele, as used herein, is any mutation (deletion, insertion or substitution) in an IND allele whereby one or more codons are changed into the coding DNA and the corresponding mRNA sequence of the corresponding wild type IND allele, resulting in the substitution of one or more amino acids in the wild type IND protein for one or more other amino acids in the mutant IND protein. In one embodiment, a mutant IND allele comprising a missense mutation is an IND allele wherein one or more of the conserved amino acids indicated above or in Table 1 is/are substituted. As indicated above, some of the conserved amino acids are more critical for the biological activity of the IND protein than others. Thus, missense mutations which result in the substitution of, e.g., the amino acids at position 5, 9, and 13 or at positions 10 and 12 of the consensus bHLH domain sequence defined by Heim et al. (supra) are more likely to result in a significantly reduced or no activity, due to a reduced ability to bind to the target DNA, of the IND protein. Similarly missense mutations which result in the substitution of, e.g., the amino acids at position 16, 20, 23, 27 in helix1 or at positions 36, 39, 43, 49, 53, and 56 in helix2 of the consensus bHLH domain sequence defined by Heim et al. (supra) are more likely to result in a significantly reduced or no activity, due to a reduced dimerization ability, of the IND protein. Seeds comprising a mutant IND-A1 allele comprising a missense mutation which causes the substitution of the Arg residue at position 10 of the consensus bHLH domain sequence defined by Heim et al. (supra) for an His residue (called hereinafter ind-a1-EMS05) have been deposited at the ATCC on Nov. 20, 2007, under accession number PTA-8795. In another embodiment, a mutant IND allele comprising a missense mutation is an IND allele comprising a missense mutation corresponding to the missense mutation in the *Arabidopsis* ind-1 or ind-3 (Liljegren et al., 2004, supra) alleles (see Table 1).

A frameshift mutation in an IND allele, as used herein, is a mutation (deletion, insertion, duplication, and the like) in an IND allele that results in the nucleic acid sequence being translated in a different frame downstream of the mutation. In one embodiment, a mutant IND allele comprising a frameshift mutation is an IND allele comprising a frameshift mutation corresponding to the frameshift mutation in the *Arabidopsis* ind-2 (Liljegren et al., 2004, supra) allele, wherein a single nucleotide is deleted within codon 26, which results in a frameshift and production of a truncated protein of 35 amino acids (according to Liljegren et al., 2004, supra). In another embodiment, a mutant IND allele comprising a frameshift mutation is an IND allele comprising a frameshift mutation corresponding to the frameshift mutation in the *Arabidopsis* ind-6 (Wu et al., 2006, supra) allele, wherein a Ds transposon is inserted after nucleotide 183 causing an 8 nucleotide duplication at the insertion site, or to the corresponding revertant *Arabidopsis* ind alleles (see Wu et al., 2006, supra, FIG. 1a).

Amino Acid Sequences According to the Invention

Provided are both wild type (functional) IND amino acid sequences and mutant IND amino acid sequences (comprising one or more mutations, preferably mutations which result in a significantly reduced or no biological activity of the IND protein) from Brassicaceae, particularly from *Brassica* species, especially from *Brassica napus*, but also from other *Brassica* crop species. For example, *Brassica* species comprising an A and/or a C genome may encode different IND-A or IND-C amino acids. In addition, mutagenesis methods can be used to generate mutations in wild type IND alleles, thereby generating mutant alleles which can encode further mutant IND proteins. In one embodiment the wild type and/or mutant IND amino acid sequences are provided within a *Brassica* plant (i.e. endogenously). However, isolated IND amino acid sequences (e.g. isolated from the plant or made synthetically), as well as variants thereof and fragments of any of these are also provided herein.

Amino acid sequences of IND-A1 and IND-C1 proteins have been isolated from *Brassica napus* as depicted in the sequence listing. The wild type IND sequences are depicted, while the mutant IND sequences of these sequences, and of sequences essentially similar to these, are described herein below, with reference to the wild type IND sequences.

As described above, the IND proteins of *Brassica* described herein are about 185-210 amino acids in length and comprise a number of structural and functional domains.

"IND-A1 amino acid sequences" or "IND-A1 variant amino acid sequences" according to the invention are amino acid sequences having at least 75%, at least 80%, at least 85%, at least 90%, at least 95%, 98%, 99% or 100% sequence identity with SEQ ID NO: 2. These amino acid sequences may also be referred to as being "essentially similar" or "essentially identical" to the IND sequences provided in the sequence listing.

"IND-C1 amino acid sequences" or "IND-C1 variant amino acid sequences" according to the invention are amino acid sequences having at least 75%, at least 80%, at least 85%, at least 90%, at least 95%, 96%, 97%, 98%, 99% or 100% sequence identity with SEQ ID NO: 4 (IND-C1-long) or with SEQ ID NO:4 from the amino acid at position 16 to the amino acid at position 210 (IND-C1-short). These amino acid sequences may also be referred to as being "essentially similar" or "essentially identical" the IND sequences provided in the sequence listing.

Thus, the invention provides both amino acid sequences of wild type, functional IND-A1 and IND-C1 proteins, including variants and fragments thereof (as defined further below), as well as mutant amino acid sequences of any of these, whereby the mutation in the amino acid sequence preferably results in a significant reduction in or a complete abolishment of the biological activity of the IND protein as compared to the biological activity of the corresponding wild type IND protein. A significant reduction in or complete abolishment of the biological activity of the IND protein refers herein to a reduction in or abolishment of the DNA binding activity, the dimerization capacity and/or transcriptional regulating activity of the IND protein, such that the pod shatter resistance of a plant expressing the mutant IND protein is increased as compared to a plant expressing the corresponding wild type IND protein compared to the pod shatter resistance of a corresponding wild type plant.

Both endogenous and isolated amino acid sequences are provided herein. Also provided are fragments of the IND amino acid sequences and IND variant amino acid sequences defined above. A "fragment" of a IND amino acid sequence or variant thereof (as defined) may be of various lengths, such as at least 10, 12, 15, 18, 20, 50, 100, 150, 175, 180 contiguous amino acids of the IND sequence (or of the variant sequence).

Amino Acid Sequences of Functional IND Proteins

The amino acid sequences depicted in the sequence listing are wild type, functional IND proteins from *Brassica napus*. Thus, these sequences are endogenous to the *Brassica napus* plants from which they were isolated. Other *Brassica* crop species, varieties, breeding lines or wild accessions may be screened for other functional IND proteins with the same amino acid sequences or variants thereof, as described above.

In addition, it is understood that IND amino acid sequences and variants thereof (or fragments of any of these) may be identified in silico, by screening amino acid databases for essentially similar sequences. Fragments of amino acid molecules according to the invention are also provided. Fragments include amino acid sequences of the bHLH domain, or smaller fragments comprising part of the bHLH domain, such as the basic domain or the HLH domain, etc.

Amino Acid Sequences of Mutant IND Proteins

Amino acid sequences comprising one or more amino acid deletions, insertions or substitutions relative to the wild type amino acid sequences are another embodiment of the invention, as are fragments of such mutant amino acid molecules. Such mutant amino acid sequences can be generated and/or identified using various known methods, as described above. Again, such amino acid molecules are provided both in endogenous form and in isolated form.

In one embodiment, the mutation(s) in the amino acid sequence result in a significantly reduced or completely abolished biological activity of the IND protein relative to the wild type protein. As described above, basically, any mutation which results in a protein comprising at least one amino acid insertion, deletion and/or substitution relative to the wild type protein can lead to significantly reduced or no biological activity. It is, however, understood that mutations in certain parts of the protein are more likely to result in a reduced function of the mutant IND protein, such as mutations leading to truncated proteins, whereby significant portions of the functional domains, such as the DNA binding domain (V), the dimerization domain ('HLH') and/or amino acids which are important in the regulation of transcription (See Table 1), are lacking or are being substituted.

Thus in one embodiment, mutant IND proteins are provided comprising one or more deletion or insertion mutations, whereby the deletion(s) or insertion(s) result(s) in a mutant protein which has significantly reduced or no activity in vivo. Such mutant IND proteins are IND proteins wherein at least 1, at least 2, 3, 4, 5, 10, 20, 30, 50, 100, 100, 150, 175, 180 or more amino acids are deleted or inserted as compared to the wild type IND protein, whereby the deletion(s) or insertion(s) result(s) in a mutant protein which has significantly reduced or no activity in vivo.

In another embodiment, mutant IND proteins are provided which are truncated whereby the truncation results in a mutant protein that has significantly reduced or no activity in vivo. Such truncated IND proteins are IND proteins which lack functional domains in the C-terminal part of the corresponding wild type IND protein and which maintain the N-terminal part of the corresponding wild type IND protein. Thus in one embodiment, a truncated IND protein comprising the N-terminal part of the corresponding wild type IND protein up to but not including the conserved Leu residue of the H2 domain (at position 56 in the consensus bHLH domain sequence as described by Heim et al., 2003, see above) is provided. The more truncated the mutant protein is in comparison to the wild type protein, the more the truncation may result in a significantly reduced or no activity of the IND protein. Thus in another embodiment, a truncated IND protein comprising the N-terminal part of the corresponding wild type IND protein lacking part or all of the second H domain, and/or lacking part or all of the L domain, and/or lacking part or all of the first H domain, and/or lacking part or all of the basic domain (as described above), or even more amino acids are provided (see Table above).

In yet another embodiment, mutant IND proteins are provided comprising one or more substitution mutations, whereby the substitution(s) result(s) in a mutant protein that has significantly reduced or no activity in vivo. Such mutant IND proteins are IND proteins whereby conserved amino acid residues which have a specific function, such as a function in DNA binding, dimerization or transcription regulation, are substituted. Thus in one embodiment, a mutant IND protein comprising a substitution of a conserved amino acid residue which has a biological function, such as the conserved amino acids of the basic domain, or the H1, L or H2 domain as indicated in Table 1 above, is provided.

METHODS ACCORDING TO THE INVENTION

Mutant ind alleles may be generated (for example induced by mutagenesis) and/or identified using a range of methods, which are conventional in the art, for example using PCR based methods to amplify part or all of the ind genomic or cDNA.

Following mutagenesis, plants are grown from the treated seeds, or regenerated from the treated cells using known techniques. For instance, mutagenized seeds may be planted in accordance with conventional growing procedures and following self-pollination seed is formed on the plants. Alternatively, doubled haploid plantlets may be extracted from treated microspore or pollen cells to immediately form homozygous plants, for example as described by Coventry et al. (1988, Manual for Microspore Culture Technique for *Brassica napus*. Dep. Crop Sci. Techn. Bull. OAC Publication 0489. Univ. of Guelph, Guelph, Ontario, Canada). Additional seed which is formed as a result of such self-pollination in the present or a subsequent generation may be harvested and screened for the presence of mutant IND alleles, using techniques which are conventional in the art, for example polymerase chain reaction (PCR) based techniques (amplification of the ind alleles) or hybridization based techniques, e.g. Southern blot analysis, BAC library screening, and the like, and/or direct sequencing of ind alleles. To screen for the presence of point mutations (so called Single Nucleotide Polymorphisms or SNPs) in mutant IND alleles, SNP detection methods conventional in the art can be used, for example oligoligation-based techniques, single base extension-based techniques or techniques based on differences in restriction sites, such as TILLING.

As described above, mutagenization (spontaneous as well as induced) of a specific wild-type IND allele results in the presence of one or more deleted, inserted, or substituted nucleotides (hereinafter called "mutation region") in the resulting mutant IND allele. The mutant IND allele can thus be characterized by the location and the configuration of the one or more deleted, inserted, or substituted nucleotides in the wild type IND allele. The site in the wild type IND allele where the one or more nucleotides have been inserted, deleted, or substituted, respectively, is herein also referred to as the "mutation region or sequence". A "5' or 3' flanking region or sequence" as used herein refers to a DNA region or sequence in the mutant (or the corresponding wild type) IND allele of at least 20 bp, preferably at least 50 bp, at least 750 bp, at least 1500 bp, and up to 5000 bp of DNA different from the DNA containing the one or more deleted, inserted, or substituted nucleotides, preferably DNA from the mutant (or the corresponding wild type) IND allele which is located either immediately upstream of and contiguous with (5' flanking region or sequence") or immediately downstream of and contiguous with (3' flanking region or sequence") the mutation region in the mutant IND allele (or in the corresponding wild type IND allele). A "joining region" as used herein refers to a DNA region in the mutant (or the corresponding wild type) IND allele where the mutation region and the 5' or 3' flanking region are linked to each other. A "sequence spanning the joining region between the mutation region and the 5' or 3' flanking region thus comprises a mutation sequence as well as the flanking sequence contiguous therewith.

The tools developed to identify a specific mutant IND allele or the plant or plant material comprising a specific mutant IND allele, or products which comprise plant material comprising a specific mutant IND allele are based on the specific genomic characteristics of the specific mutant IND allele as compared to the genomic characteristics of the corresponding wild type IND allele, such as, a specific restriction map of the genomic region comprising the mutation region, molecular markers or the sequence of the flanking and/or mutation regions.

Once a specific mutant IND allele has been sequenced, primers and probes can be developed which specifically recognize a sequence within the 5' flanking, 3' flanking and/or mutation regions of the mutant IND allele in the nucleic acid (DNA or RNA) of a sample by way of a molecular biological technique. For instance a PCR method can be developed to identify the mutant IND allele in biological samples (such as samples of plants, plant material or products comprising plant material). Such a PCR is based on at least two specific "primers": one recognizing a sequence within the 5' or 3' flanking region of the mutant IND allele and the other recognizing a sequence within the 3' or 5' flanking region of the mutant IND allele, respectively; or one recognizing a sequence within the 5' or 3' flanking region of the mutant IND allele and the other recognizing a sequence within the mutation region of the mutant IND allele; or one recognizing a sequence within the 5' or 3' flanking region of the mutant IND allele and the other recognizing a sequence spanning the joining region between the 3' or 5' flanking region and the mutation region of the specific mutant IND allele (as described further below), respectively.

The primers preferably have a sequence of between 15 and 35 nucleotides which under optimized PCR conditions "specifically recognize" a sequence within the 5' or 3' flanking region, a sequence within the mutation region, or a sequence spanning the joining region between the 3' or 5' flanking and mutation regions of the specific mutant IND allele, so that a specific fragment ("mutant IND specific fragment" or discriminating amplicon) is amplified from a nucleic acid sample comprising the specific mutant IND allele. This means that only the targeted mutant IND allele, and no other sequence in the plant genome, is amplified under optimized PCR conditions.

PCR primers suitable for the invention may be the following:
  oligonucleotides ranging in length from 17 nt to about 200 nt, comprising a nucleotide sequence of at least 17 consecutive nucleotides, preferably 20 consecutive nucleotides selected from the 5' or 3' flanking sequence of a specific mutant IND allele or the complement thereof (i.e., for example, the sequence 5' or 3' flanking the one or more nucleotides deleted, inserted or substituted in the mutant IND alleles of the invention, such as the sequence 5' or 3' flanking the non-sense, missense or frameshift mutations described above or the sequence 5' or 3' flanking the STOP codon mutations indicated in the above Tables or the substitution mutations indicated above or the complement thereof) (primers recognizing 5' flanking sequences); or
  oligonucleotides ranging in length from 17 nt to about 200 nt, comprising a nucleotide sequence of at least 17 consecutive nucleotides, preferably 20 nucleotides selected from the sequence of the mutation region of a specific mutant IND allele or the complement thereof (i.e., for example, the sequence of nucleotides inserted or substituted in the IND genes of the invention or the complement thereof) (primers recognizing mutation sequences).

The primers may of course be longer than the mentioned 17 consecutive nucleotides, and may e.g. be 18, 19, 20, 21, 30, 35, 50, 75, 100, 150, 200 nt long or even longer. The primers may entirely consist of nucleotide sequence selected from the mentioned nucleotide sequences of flanking and mutation sequences. However, the nucleotide sequence of the primers at their 5' end (i.e. outside of the 3'-located 17 consecutive nucleotides) is less critical. Thus, the 5' sequence of the primers may consist of a nucleotide sequence selected from the flanking or mutation sequences, as appropriate, but may contain several (e.g. 1, 2, 5, 10) mismatches. The 5' sequence of the primers may even entirely consist of a nucleotide sequence unrelated to the flanking or mutation sequences, such as e.g. a nucleotide sequence representing restriction enzyme recognition sites. Such unrelated sequences or flanking DNA sequences with mismatches should preferably be not longer than 100, more preferably not longer than 50 or even 25 nucleotides.

Moreover, suitable primers may comprise or consist of a nucleotide sequence spanning the joining region between flanking and mutation sequences (i.e., for example, the joining region between a sequence 5' or 3' flanking one or more nucleotides deleted, inserted or substituted in the mutant IND alleles of the invention and the sequence of the one or more nucleotides inserted or substituted or the sequence 3' or 5', respectively, flanking the one or more nucleotides deleted, such as the joining region between a sequence 5' or 3' flanking non-sense, missense or frameshift mutations in the IND genes of the invention described above and the sequence of the non-sense, missense or frameshift mutations, or the joining region between a sequence 5' or 3' flanking a potential STOP codon mutation as indicated in the above Tables or the substitution mutations indicated above and the sequence of the potential STOP codon mutation or the substitution mutations, respectively), provided the nucleotide sequence is not derived exclusively from either the mutation region or flanking regions.

It will also be immediately clear to the skilled artisan that properly selected PCR primer pairs should also not comprise sequences complementary to each other.

For the purpose of the invention, the "complement of a nucleotide sequence represented in SEQ ID No: X" is the nucleotide sequence which can be derived from the represented nucleotide sequence by replacing the nucleotides through their complementary nucleotide according to Chargaff's rules (A↔T; G↔C) and reading the sequence in the 5' to 3' direction, i.e. in opposite direction of the represented nucleotide sequence.

Examples of primers suitable to identify specific mutant IND alleles are described in the Examples.

As used herein, "the nucleotide sequence of SEQ ID No. Z from position X to position Y" indicates the nucleotide sequence including both nucleotide endpoints.

Preferably, the amplified fragment has a length of between 50 and 1000 nucleotides, such as a length between 50 and 500 nucleotides, or a length between 100 and 350 nucleotides. The specific primers may have a sequence which is between 80 and 100% identical to a sequence within the 5' or 3' flanking region, to a sequence within the mutation region, or to a sequence spanning the joining region between the 3' or 5' flanking and mutation regions of the specific mutant IND allele, provided the mismatches still allow specific identification of the specific mutant IND allele with these primers under optimized PCR conditions. The range of allowable mismatches however, can easily be determined experimentally and are known to a person skilled in the art.

Detection and/or identification of a "mutant IND specific fragment" can occur in various ways, e.g., via size estimation after gel or capillary electrophoresis or via fluorescence-based detection methods. The mutant IND specific fragments may also be directly sequenced. Other sequence specific methods for detection of amplified DNA fragments are also known in the art.

Standard PCR protocols are described in the art, such as in 'PCR Applications Manual" (Roche Molecular Biochemicals, 2nd Edition, 1999) and other references. The optimal conditions for the PCR, including the sequence of the specific primers, is specified in a "PCR identification protocol" for each specific mutant IND allele. It is however understood that a number of parameters in the PCR identification protocol may need to be adjusted to specific laboratory conditions, and may be modified slightly to obtain similar results. For instance, use of a different method for preparation of DNA may require adjustment of, for instance, the amount of primers, polymerase, $MgCl_2$ concentration or annealing conditions used. Similarly, the selection of other primers may dictate other optimal conditions for the PCR identification protocol. These adjustments will however be apparent to a person skilled in the art, and are furthermore detailed in current PCR application manuals such as the one cited above.

Examples of PCR identification protocols to identify specific mutant IND alleles are described in the Examples.

Alternatively, specific primers can be used to amplify a mutant IND specific fragment that can be used as a "specific probe" for identifying a specific mutant IND allele in biological samples. Contacting nucleic acid of a biological sample, with the probe, under conditions that allow hybridization of the probe with its corresponding fragment in the nucleic acid, results in the formation of a nucleic acid/probe hybrid. The formation of this hybrid can be detected (e.g. labeling of the nucleic acid or probe), whereby the formation of this hybrid indicates the presence of the specific mutant IND allele. Such identification methods based on hybridization with a specific probe (either on a solid phase carrier or in solution) have been described in the art. The specific probe is preferably a sequence that, under optimized conditions, hybridizes specifically to a region within the 5' or 3' flanking region and/or within the mutation region of the specific mutant IND allele (hereinafter referred to as "mutant IND specific region"). Preferably, the specific probe comprises a sequence of between 10 and 1000 bp, 50 and 600 bp, between 100 to 500 bp, between 150 to 350 bp, which is at least 80%, preferably between 80 and 85%, more preferably between 85 and 90%, especially preferably between 90 and 95%, most preferably between 95% and 100% identical (or complementary) to the nucleotide sequence of a specific region. Preferably, the specific probe will comprise a sequence of about 13 to about 100 contiguous nucleotides identical (or complementary) to a specific region of the specific mutant IND allele.

Specific probes suitable for the invention may be the following:

oligonucleotides ranging in length from 13 nt to about 1000 nt, comprising a nucleotide sequence of at least 13 consecutive nucleotides selected from the 5' or 3' flanking sequence of a specific mutant IND allele or the complement thereof (i.e., for example, the sequence 5' or 3' flanking the one or more nucleotides deleted, inserted or substituted in the mutant IND alleles of the invention, such as the sequence 5' or 3' flanking the non-sense, mis-sense or frameshift mutations described above or the sequence 5' or 3' flanking the potential STOP codon mutations indicated in the above Tables or the substitution mutations indicated above), or a sequence having at least 80% sequence identity therewith (probes recognizing 5' flanking sequences); or oligonucleotides ranging in length from 13 nt to about 1000 nt, comprising a nucleotide sequence of at least 13 consecutive nucleotides selected from the mutation sequence of a specific mutant IND allele or the complement thereof (i.e., for example, the sequence of nucleotides inserted or substituted in the IND genes of the invention, or the complement thereof), or a sequence having at least 80% sequence identity therewith (probes recognizing mutation sequences).

The probes may entirely consist of nucleotide sequence selected from the mentioned nucleotide sequences of flanking and mutation sequences. However, the nucleotide sequence of the probes at their 5' or 3' ends is less critical. Thus, the 5' or 3' sequences of the probes may consist of a nucleotide sequence selected from the flanking or mutation sequences, as appropriate, but may consist of a nucleotide sequence unrelated to the flanking or mutation sequences. Such unrelated sequences should preferably be not longer than 50, more preferably not longer than 25 or even not longer than 20 or 15 nucleotides.

Moreover, suitable probes may comprise or consist of a nucleotide sequence spanning the joining region between flanking and mutation sequences (i.e., for example, the joining region between a sequence 5' or 3' flanking one or more nucleotides deleted, inserted or substituted in the mutant IND alleles of the invention and the sequence of the one or more nucleotides inserted or substituted or the sequence 3' or 5', respectively, flanking the one or more nucleotides deleted, such as the joining region between a sequence 5' or 3' flanking non-sense, mis-sense or frameshift mutations in the IND genes of the invention described above and the sequence of the non-sense, mis-sense or frameshift mutations, or the joining region between a sequence 5' or 3' flanking a potential STOP codon mutation as indicated in the above Tables or the substitution mutations indicated above and the sequence of the potential STOP codon or substitution mutation, respectively), provided the mentioned nucleotide sequence is not derived exclusively from either the mutation region or flanking regions.

Examples of specific probes suitable to identify specific mutant IND alleles are described in the Examples.

Detection and/or identification of a "mutant IND specific region" hybridizing to a specific probe can occur in various ways, e.g., via size estimation after gel electrophoresis or via fluorescence-based detection methods. Other sequence specific methods for detection of a "mutant IND specific region" hybridizing to a specific probe are also known in the art.

Alternatively, plants or plant parts comprising one or more mutant ind alleles can be generated and identified using other methods, such as the "Delete-a-Gene™" method which uses PCR to screen for deletion mutants generated by fast neutron mutagenesis (reviewed by Li and Zhang, 2002, Funct Integr Genomics 2:254-258), by the TILLING (Targeting Induced Local Lesions IN Genomes) method which identifies EMS-induced point mutations using denaturing high-performance liquid chromatography (DHPLC) to detect base pair changes by heteroduplex analysis (McCallum et al., 2000, Nat Biotech 18:455, and McCallum et al. 2000, Plant Physiol. 123, 439-442), etc. As mentioned, TILLING uses high-throughput screening for mutations (e.g. using Cel 1 cleavage of mutant-wildtype DNA heteroduplexes and detection using a sequencing gel system). Thus, the use of TILLING to identify plants or plant parts comprising one or more mutant ind alleles and methods for generating and identifying such plants, plant organs, tissues and seeds is encompassed herein. Thus in one embodiment, the method according to the invention comprises the steps of mutagenizing plant seeds (e.g. EMS mutagenesis), pooling of plant individuals or DNA, PCR amplification of a region of interest, heteroduplex formation and high-throughput detection, identification of the mutant plant, sequencing of the mutant PCR product. It is understood that other mutagenesis and selection methods may equally be used to generate such mutant plants.

Instead of inducing mutations in IND alleles, natural (spontaneous) mutant alleles may be identified by methods known in the art. For example, ECOTILLING may be used (Henikoff et al. 2004, Plant Physiology 135(2):630-6) to screen a plurality of plants or plant parts for the presence of natural mutant ind alleles. As for the mutagenesis techniques above, preferably *Brassica* species are screened which comprise an A and/or a C genome, so that the identified ind allele can subsequently be introduced into other *Brassica* species, such as *Brassica napus*, by crossing (inter- or intraspecific crosses) and selection. In ECOTILLING natural polymorphisms in breeding lines or related species are screened for by the TILLING methodology described above, in which individual or pools of plants are used for PCR amplification of the ind target, heteroduplex formation and high-throughput analysis. This can be followed by selecting individual plants having a required mutation that can be used subsequently in a breeding program to incorporate the desired mutant allele.

The identified mutant alleles can then be sequenced and the sequence can be compared to the wild type allele to identify the mutation(s). Optionally functionality can be tested as indicated above. Using this approach a plurality of mutant ind alleles (and *Brassica* plants comprising one or more of these) can be identified. The desired mutant alleles can then be combined with the desired wild type alleles by crossing and selection methods as described further below. Finally a single plant comprising the desired number of mutant ind and the desired number of wild type IND alleles is generated.

Oligonucleotides suitable as PCR primers or specific probes for detection of a specific mutant IND allele can also be used to develop methods to determine the zygosity status of the specific mutant IND allele.

To determine the zygosity status of a specific mutant IND allele, a PCR-based assay can be developed to determine the presence of a mutant and/or corresponding wild type IND specific allele:

To determine the zygosity status of a specific mutant IND allele, two primers specifically recognizing the wild-type IND allele can be designed in such a way that they are directed towards each other and have the mutation region located in between the primers. These primers may be primers specifically recognizing the 5' and 3' flanking sequences, respectively. This set of primers allows simultaneous diagnostic PCR amplification of the mutant, as well as of the corresponding wild type IND allele.

Alternatively, to determine the zygosity status of a specific mutant IND allele, two primers specifically recognizing the wild-type IND allele can be designed in such a way that they are directed towards each other and that one of them specifically recognizes the mutation region. These primers may be primers specifically recognizing the sequence of the 5' or 3' flanking region and the mutation region of the wild type IND allele, respectively. This set of primers, together with a third primer which specifically recognizes the sequence of the mutation region in the mutant IND allele, allow simultaneous diagnostic PCR amplification of the mutant IND gene, as well as of the wild type IND gene.

Alternatively, to determine the zygosity status of a specific mutant IND allele, two primers specifically recognizing the wild-type IND allele can be designed in such a way that they are directed towards each other and that one of them specifically recognizes the joining region between the 5' or 3' flanking region and the mutation region. These primers may be primers specifically recognizing the 5' or 3' flanking sequence and the joining region between the mutation region and the 3' or 5' flanking region of the wild type IND allele, respectively. This set of primers, together with a third primer which specifically recognizes the joining region between the mutation region and the 3' or 5' flanking region of the mutant IND allele, respectively, allow simultaneous diagnostic PCR amplification of the mutant IND gene, as well as of the wild type IND gene.

Alternatively, the zygosity status of a specific mutant IND allele can be determined by using alternative primer sets that specifically recognize mutant and wild type IND alleles.

If the plant is homozygous for the mutant IND gene or the corresponding wild type IND gene, the diagnostic PCR assays described above will give rise to a single PCR product typical, preferably typical in length, for either the mutant or wild type IND allele. If the plant is heterozygous for the mutant IND allele, two specific PCR products will appear, reflecting both the amplification of the mutant and the wild type IND allele.

Identification of the wild type and mutant IND specific PCR products can occur e.g. by size estimation after gel or capillary electrophoresis (e.g. for mutant IND alleles comprising a number of inserted or deleted nucleotides which results in a size difference between the fragments amplified from the wild type and the mutant IND allele, such that said fragments can be visibly separated on a gel); by evaluating the presence or absence of the two different fragments after gel or capillary electrophoresis, whereby the diagnostic PCR amplification of the mutant IND allele can, optionally, be performed separately from the diagnostic PCR amplification of the wild type IND allele; by direct sequencing of the amplified fragments; or by fluorescence-based detection methods.

Examples of primers suitable to determine the zygosity of specific mutant IND alleles are described in the Examples.

Alternatively, to determine the zygosity status of a specific mutant IND allele, a hybridization-based assay can be developed to determine the presence of a mutant and/or corresponding wild type IND specific allele:

To determine the zygosity status of a specific mutant IND allele, two specific probes recognizing the wild-type IND allele can be designed in such a way that each probe specifically recognizes a sequence within the IND wild type allele and that the mutation region is located in between the sequences recognized by the probes. These probes may be probes specifically recognizing the 5' and 3' flanking sequences, respectively. The use of one or, preferably, both of these probes allows simultaneous diagnostic hybridization of the mutant, as well as of the corresponding wild type IND allele.

Alternatively, to determine the zygosity status of a specific mutant IND allele, two specific probes recognizing the wild-type IND allele can be designed in such a way that one of them specifically recognizes a sequence within the IND wild type allele upstream or downstream of the mutation region, preferably upstream of the mutation region, and that one of them specifically recognizes the mutation region. These probes may be probes specifically recognizing the sequence of the 5' or 3' flanking region, preferably the 5' flanking region, and the mutation region of the wild type IND allele, respectively. The use of one or, preferably, both of these probes, optionally, together with a third probe which specifically recognizes the sequence of the mutation region in the mutant IND allele, allow diagnostic hybridization of the mutant and of the wild type IND gene.

Alternatively, to determine the zygosity status of a specific mutant IND allele, a specific probe recognizing the wild-type IND allele can be designed in such a way that the probe specifically recognizes the joining region between the 5' or 3' flanking region, preferably the 5' flanking region, and the mutation region of the wild type IND allele. This probe, optionally, together with a second probe that specifically recognizes the joining region between the 5' or 3' flanking region, preferably the 5' flanking region, and the mutation region of the mutant IND allele, allows diagnostic hybridization of the mutant and of the wild type IND gene.

Alternatively, the zygosity status of a specific mutant IND allele can be determined by using alternative sets of probes that specifically recognize mutant and wild type IND alleles.

If the plant is homozygous for the mutant IND gene or the corresponding wild type IND gene, the diagnostic hybridization assays described above will give rise to a single specific hybridization product, such as one or more hybridizing DNA (restriction) fragments, typical, preferably typical in length, for either the mutant or wild type IND allele. If the plant is heterozygous for the mutant IND allele, two specific hybridization products will appear, reflecting both the hybridization of the mutant and the wild type IND allele.

Identification of the wild type and mutant IND specific hybridization products can occur e.g. by size estimation after gel or capillary electrophoresis (e.g. for mutant IND alleles comprising a number of inserted or deleted nucleotides which results in a size difference between the hybridizing DNA (restriction) fragments from the wild type and the mutant IND allele, such that said fragments can be visibly separated on a gel); by evaluating the presence or absence of the two different specific hybridization products after gel or capillary electrophoresis, whereby the diagnostic hybridization of the mutant IND allele can, optionally, be performed separately from the diagnostic hybridization of the wild type IND allele; by direct sequencing of the hybridizing DNA (restriction) fragments; or by fluorescence-based detection methods.

Examples of probes suitable to determine the zygosity of specific mutant IND alleles are described in the Examples.

Furthermore, detection methods specific for a specific mutant IND allele that differ from PCR- or hybridization-based amplification methods can also be developed using the specific mutant IND allele specific sequence information provided herein. Such alternative detection methods include linear signal amplification detection methods based on invasive cleavage of particular nucleic acid structures, also known as Invader™ technology, (as described e.g. in U.S. Pat. No. 5,985,557 "Invasive Cleavage of Nucleic Acids", U.S. Pat. No. 6,001,567 "Detection of Nucleic Acid sequences by Invader Directed Cleavage, incorporated herein by reference), RT-PCR-based detection methods, such as Taqman, or other detection methods, such as SNPlex. Briefly, in the Invader™ technology, the target mutation sequence may e.g. be hybridized with a labeled first nucleic acid oligonucleotide comprising the nucleotide sequence of the mutation sequence or a sequence spanning the joining region between the 5' flanking region and the mutation region and with a second nucleic acid oligonucleotide comprising the 3' flanking sequence immediately downstream and adjacent to the mutation sequence, wherein the first and second oligonucleotide overlap by at least one nucleotide. The duplex or triplex structure that is produced by this hybridization allows selective probe cleavage with an enzyme (Cleavase®) leaving the target sequence intact. The cleaved labeled probe is subsequently detected, potentially via an intermediate step resulting in further signal amplification.

A "kit", as used herein, refers to a set of reagents for the purpose of performing the method of the invention, more particularly, the identification of a specific mutant IND allele in biological samples or the determination of the zygosity status of plant material comprising a specific mutant IND allele. More particularly, a preferred embodiment of the kit of the invention comprises at least two specific primers, as described above, for identification of a specific mutant IND allele, or at least two or three specific primers for the determination of the zygosity status. Optionally, the kit can further comprise any other reagent described herein in the PCR identification protocol. Alternatively, according to another embodiment of this invention, the kit can comprise at least one specific probe, which specifically hybridizes with nucleic acid of biological samples to identify the presence of a specific mutant IND allele therein, as described above, for identification of a specific mutant IND allele, or at least two or three specific probes for the determination of the zygosity status. Optionally, the kit can further comprise any other reagent (such as but not limited to hybridizing buffer, label) for identification of a specific mutant IND allele in biological samples, using the specific probe.

The kit of the invention can be used, and its components can be specifically adjusted, for purposes of quality control (e.g., purity of seed lots), detection of the presence or absence of a specific mutant IND allele in plant material or material comprising or derived from plant material, such as but not limited to food or feed products.

The term "primer" as used herein encompasses any nucleic acid that is capable of priming the synthesis of a nascent nucleic acid in a template-dependent process, such as PCR. Typically, primers are oligonucleotides from 10 to 30 nucleotides, but longer sequences can be employed. Primers may be provided in double-stranded form, though the single-stranded form is preferred. Probes can be used as primers, but are designed to bind to the target DNA or RNA and need not be used in an amplification process.

The term "recognizing" as used herein when referring to specific primers, refers to the fact that the specific primers specifically hybridize to a nucleic acid sequence in a specific mutant IND allele under the conditions set forth in the method (such as the conditions of the PCR identification protocol), whereby the specificity is determined by the presence of positive and negative controls.

The term "hybridizing", as used herein when referring to specific probes, refers to the fact that the probe binds to a specific region in the nucleic acid sequence of a specific mutant IND allele under standard stringency conditions. Standard stringency conditions as used herein refers to the conditions for hybridization described herein or to the conventional hybridizing conditions as described by Sambrook et al., 1989 (Molecular Cloning: A Laboratory Manual, Second Edition, Cold Spring Harbour Laboratory Press, NY) which for instance can comprise the following steps: 1) immobilizing plant genomic DNA fragments or BAC library DNA on a filter, 2) prehybridizing the filter for 1 to 2 hours at 65° C. in 6×SSC, 5×Denhardt's reagent, 0.5% SDS and 20 µg/ml denatured carrier DNA, 3) adding the hybridization probe which has been labeled, 4) incubating for 16 to 24 hours, 5) washing the filter once for 30 min. at 68° C. in 6×SSC, 0.1% SDS, 6) washing the filter three times (two times for 30 min. in 30 ml and once for 10 min in 500 ml) at 68° C. in 2×SSC, 0.1% SDS, and 7) exposing the filter for 4 to 48 hours to X-ray film at −70° C.

As used in herein, a "biological sample" is a sample of a plant, plant material or product comprising plant material. The term "plant" is intended to encompass plant tissues, at any stage of maturity, as well as any cells, tissues, or organs taken from or derived from any such plant, including without limitation, any seeds, leaves, stems, flowers, roots, single cells, gametes, cell cultures, tissue cultures or protoplasts. "Plant material", as used herein refers to material that is obtained or derived from a plant. Products comprising plant material relate to food, feed or other products that are produced using plant material or can be contaminated by plant material. It is understood that, in the context of the present invention, such biological samples are tested for the presence of nucleic acids specific for a specific mutant IND allele, implying the presence of nucleic acids in the samples. Thus the methods referred to herein for identifying a specific mutant IND allele in biological samples, relate to the identification in biological samples of nucleic acids that comprise the specific mutant IND allele.

The present invention also relates to the combination of specific IND alleles in one plant, to the transfer of one or more specific mutant IND allele(s) from one plant to another plant, to the plants comprising one or more specific mutant IND allele(s), the progeny obtained from these plants and to plant cells, plant parts, and plant seeds derived from these plants.

Thus, in one embodiment of the invention a method for combining two or more selected mutant IND alleles in one plant is provided comprising the steps of
(a) generating and/or identifying two or more plants each comprising one or more selected mutant IND alleles, as described above,
(b) crossing a first plant comprising one or more selected mutant IND alleles with a second plant comprising one or more other selected mutant IND alleles, collecting F1 seeds from the cross, and, optionally, identifying an F1 plant comprising one or more selected mutant IND alleles from the first plant with one or more selected mutant IND alleles from the second plant, as described above,
(c) optionally, repeating step (b) until an F1 plant comprising all selected mutant IND alleles is obtained,
(d) optionally,
identifying an F1 plant, which is homozygous or heterozygous for a selected mutant IND allele by determining the zygosity status of the mutant IND alleles, as described above, or
generating plants which are homozygous for one or more of the selected mutant IND alleles by performing one of the following steps:
extracting doubled haploid plants from treated microspore or pollen cells of F1 plants comprising the one or more selected mutant IND alleles, as described above,
selfing the F1 plants comprising the one or more selected mutant IND allele(s) for one or more generations (y), collecting F1 Sy seeds from the selfings, and identifying F1 Sy plants, which are homozygous for the one or more mutant IND allele, as described above.

In another embodiment of the invention a method for transferring one or more mutant IND alleles from one plant to another plant is provided comprising the steps of:
(a) generating and/or identifying a first plant comprising one or more selected mutant IND alleles, as described above, or generating the first plant by combining the one or more selected mutant IND alleles in one plant, as described above (wherein the first plant is homozygous or heterozygous for the one or more mutant IND alleles)
(b) crossing the first plant comprising the one or more mutant IND alleles with a second plant not comprising the one or more mutant IND alleles, collecting F1 seeds from the cross (wherein the seeds are heterozygous for a mutant IND allele if the first plant was homozygous for that mutant IND allele, and wherein half of the seeds are heterozygous and half of the seeds are azygous for, i.e. do not comprise, a mutant IND allele if the first plant was heterozygous for that mutant IND allele), and, optionally, identifying F1 plants comprising one or more selected mutant IND alleles, as described above,
(c) backcrossing F1 plants comprising one or more selected mutant IND alleles with the second plant not comprising the one or more selected mutant IND alleles for one or more generations (x), collecting BCx seeds from the crosses, and identifying in every generation BCx plants comprising the one or more selected mutant IND alleles, as described above,
(d) optionally, generating BCx plants which are homozygous for the one or more selected mutant IND alleles by performing one of the following steps:
extracting doubled haploid plants from treated microspore or pollen cells of BCx plants comprising the one or more desired mutant IND allele(s), as described above,
selfing the BCx plants comprising the one or more desired mutant IND allele(s) for one or more generations (y), collecting BCx Sy seeds from the selfings, and identifying BCx Sy plants, which are homozygous for the one or more desired mutant IND allele, as described above.

In one aspect of the invention, the first and the second plant are Brassicaceae plants, particularly *Brassica* plants, especially *Brassica napus* plants or plants from another *Brassica* crop species. In another aspect of the invention, the first plant is a Brassicaceae plant, particularly a *Brassica* plant, especially a *Brassica napus* plant or a plant from another *Brassica* crop species, and the second plant is a plant from a Brassicaceae breeding line, particularly from a *Brassica* breeding line, especially from a *Brassica napus* breeding line or from a breeding line from another *Brassica* crop species. "Breeding line", as used herein, is a preferably homozygous plant line distinguishable from other plant lines by a preferred genotype and/or phenotype that is used to produce hybrid offspring.

In yet another embodiment of the invention, a method for making a plant, in particular a *Brassica* crop plant, such as a *Brassica napus* plant, of which the pod shatter resistance is increased but which preferably maintains an agronomically relevant treshability of the pods is provided comprising combining and/or transferring mutant IND alleles according to the invention in or to one *Brassica* plant, as described above.

In one aspect of the invention, the plant is a *Brassica* plant comprising at least two IND genes wherein pod shatter resistance is increased while maintaining an agronomically relevant treshability of the pods by combining and/or transferring three mutant IND alleles according to the invention in or to the *Brassica* plant, as described above.

In still another embodiment of the invention, a method for making a hybrid *Brassica* crop seed or plant comprising at least two IND genes, in particular a hybrid *Brassica napus* seed or plant, of which the pod shatter resistance is increased but which maintains an agronomically relevant treshability of the pods is provided, comprising the steps of:

(a) generating and/or identifying a first plant comprising a first and a second selected mutant IND allele in homozygous state and a second plant comprising a third selected mutant IND allele in homozygous state, as described above,
(b) crossing the first and the second plant and collecting F1 hybrid seeds from the cross.

In one aspect of the invention, the first or the second selected mutant IND allele is the same mutant IND allele as the third selected mutant IND allele, such that the F1 hybrid seeds are homozygous for one mutant IND allele and heterozygous for the other. In another aspect of the invention, the first plant is used as a male parent plant and the second plant is used as a female parent plant. In one embodiment of the invention, the first plant is completely pod shatter resistant. Such plants may be obtained by sowing complete indehiscent seed pods obtained by selfing the plants and harvesting complete seed pods in stead of thrashing the seed pods to harvest the seeds.

Sequences
IND Genes
SEQ ID NO: 1: Coding DNA of the IND-A1 gene encoding a wild-type IND-A1 protein from *Brassica napus*.
SEQ ID NO: 2: wild type IND-A1 protein encoded by SEQ ID NO: 1.
SEQ ID NO: 3: Coding DNA of the IND-C1 gene encoding a wild-type IND-C1 protein from *Brassica napus*.
SEQ ID NO: 4: wild type IND-C1 protein encoded by SEQ ID NO: 3.
SEQ ID NO: 5: Genomic DNA of the IND-A1 gene encoding a wild-type IND-A1 protein from *Brassica napus*.
SEQ ID NO: 6: wild type IND-A1 protein encoded by SEQ ID NO: 5.
SEQ ID NO: 7: Genomic DNA of the IND-C1 gene encoding a wild-type IND-C1 protein from *Brassica napus*.
SEQ ID NO: 8: wild type IND-C1 protein encoded by SEQ ID NO: 7.
SEQ ID NO: 9: Coding DNA of the *Arabidopsis* IND1 gene.
SEQ ID NO: 10: *Arabidopsis* IND1 protein encoded by SEQ ID NO: 9.
SEQ ID NO: 11: nucleotide sequence of an IND homologue from *Brassica napus* (BN1-IND—SEQ ID NO: 2 of WO04/113542)
SEQ ID NO: 12: nucleotide sequence of a second IND homologue from *Brassica napus* (BN2-IND—SEQ ID NO: 3 of WO04/113542)
Primers and Probes
SEQ ID NO 13: Forward oligonucleotide for detection of IND-A1-EMS01
SEQ ID NO 14: Forward oligonucleotide for detection of IND-A1-WT
SEQ ID NO 15: Reverse oligonucleotide for detection of IND-A1-EMS01 and -WT
SEQ ID NO 16: Forward oligonucleotide for detection of IND-A1-EMS05
SEQ ID NO 17: Forward oligonucleotide for detection of IND-A1-WT
SEQ ID NO 18: Reverse oligonucleotide for detection of IND-A1-EMS05 and -WT
SEQ ID NO 19: Reverse oligonucleotide for detection of IND-C1-EMS01
SEQ ID NO 20: Reverse oligonucleotide for detection of IND-C1-WT
SEQ ID NO 21: Forward oligonucleotide for detection of IND-C1-EMS01 and -WT
SEQ ID NO 22: Reverse oligonucleotide for detection of IND-C1-EMS03
SEQ ID NO 23: Reverse oligonucleotide for detection of IND-C1-WT
SEQ ID NO 24: Forward oligonucleotide for detection of IND-C1-EMS03 and -WT
SEQ ID NO 25: Oligonucleotide for detection of IND-A1-EMS01 and -WT
SEQ ID NO 26: Oligonucleotide for detection of IND-A1-EMS01
SEQ ID NO 27: Oligonucleotide for detection of IND-A1-WT
SEQ ID NO 28: Oligonucleotide for detection of IND-A1-EMS05 and -WT
SEQ ID NO 29: Oligonucleotide for detection of IND-A1-EMS05
SEQ ID NO 30: Oligonucleotide for detection of IND-A1-WT
SEQ ID NO 31: Oligonucleotide for detection of IND-C1-EMS01 and -WT
SEQ ID NO 32: Oligonucleotide for detection of IND-C1-EMS01
SEQ ID NO 33: Oligonucleotide for detection of IND-C1-WT
SEQ ID NO 34: Oligonucleotide for detection of IND-C1-EMS03 and -WT
SEQ ID NO 35: Oligonucleotide for detection of IND-C1-EMS03
SEQ ID NO 36: Oligonucleotide for detection of IND-C1-WT
SEQ ID NO 37: Forward oligonucleotide for detection of IND-A1
SEQ ID NO 38: Reverse oligonucleotide for detection of IND-A1
SEQ ID NO 39: Forward oligonucleotide for detection of IND-C1
SEQ ID NO 40: Reverse oligonucleotide for detection of IND-C1

Unless stated otherwise in the Examples, all recombinant DNA techniques are carried out according to standard molecular biological techniques as described in Sambrook and Russell (2001) *Molecular Cloning: A Laboratory Manual*, Third Edition, Cold Spring Harbor Laboratory Press, NY, in Volumes 1 and 2 of Ausubel et al. (1994) *Current Protocols in Molecular Biology, Current Protocols*, USA and in Volumes I and II of Brown (1998) *Molecular Biology LabFax*, Second Edition, Academic Press (UK). Standard materials and methods for plant molecular work are described in *Plant Molecular Biology Labfax* (1993) by R. D. D. Croy, jointly published by BIOS Scientific Publications Ltd (UK) and Blackwell Scientific Publications, UK. Standard materials and methods for polymerase chain reactions can be found in Dieffenbach and Dveksler (1995) *PCR Primer: A Laboratory Manual*, Cold Spring Harbor Laboratory Press, and in McPherson at al. (2000) *PCR—Basics: From Background to Bench*, First Edition, Springer Verlag, Germany. Standard procedures for AFLP analysis are

EXAMPLES

Example 1

Isolation of the DNA Sequences of the IND Genes

To determine the sequences of the IND genes of an elite spring oilseed rape breeding line, a Bacterial Artificial Chromosome (BAC) library of the line was screened as follows:

1.1. Isolation of BAC Clones Comprising an IND Sequence

To identify *Escherichia coli* colonies containing a BAC clone comprising an IND sequence of the elite spring oilseed rape breeding line, a BAC library of the line (average clone size of more than 120 kb) arrayed as individual duplicated clones on high density nylon filters were screened by standard Southern hybridization procedures:

- A mixture of two probes with the sequence of SEQ ID NO: 2 of WO04/113542 ("Bn1-IND") and SEQ ID NO: 3 of WO04/113542 ("BN2-IND") (SEQ ID NO: 11 and 12, respectively) and labeled according to standard procedures were used for hybridizing to the DNA on the nylon membrane.
- Pre-hybridization was performed for 2 hour at 65° C. in 30 ml of the following hybridization buffer: 6×SSC (20×SSC contains 3.0 M NaCl, 0.3 M Na citrate, pH 7.0), 5×Denhardt's (100×Denhardt's contains 2% Ficoll, 2% Polyvinyl pyrollidone, 2% Bovine Serum Albumin), 0.5% SDS and 20 µg/ml denatured carrier DNA (single-stranded fish sperm DNA, with an average length of 120-3000 nucleotides)
- Hybridization was performed under the following conditions:
  - The labeled probe (20 ng of each sequence) was denaturated by heating for 5 minutes at 95° C. and chilling on ice for 5 minutes and added to 15 ml of hybridization buffer (same buffer as for the pre-hybridization)
  - The hybridization was performed overnight at 65° C.
- The blots were washed three times for 30 minutes at 65° C. in the hybridization tubes (once with 30 ml 6×SSC with 0.1% SDS and twice with 30 ml 2×SSC with 0.1% SDS) and one time for 10 minutes at 65° C. with 500 ml 2×SSC with 0.1% SDS in a box.
- Kodak X-OMAT AR films were exposed to the radioactive blots for 4 hours at −70° C.
- Based on the positive signals, 14 *E. coli* colonies containing a BAC clone comprising an IND sequence were picked up by screening the BAC library from the elite spring oilseed rape breeding line (total no of positives: 65) (hereinafter called "positive colonies").

1.2. Isolation of BAC Clones Comprising a Full-Length IND Sequence

To identify positive colonies comprising a BAC clone with a full-length genomic DNA sequence of one of the IND genes, a Southern blot analysis was performed on BAC clone DNA isolated from the positive colonies and on genomic DNA isolated from *Brassica napus*:

- BAC clone DNA was isolated through alkaline lysis as described in the art from the positive colonies grown up in 25 ml Luria Broth medium containing 25 µg/ml chloramphenicol.
- Genomic DNA was isolated from leaf tissue of *B. napus* according to the cetyltrimethylammoniumbromide (CTAB) method (Doyle and Doyle, 1987, Phytochemistry Bulletin 19:11-15).
- The DNA concentration of each preparation was estimated by comparing the band intensity of 1 µl of each sample to the band intensity of 1, 2, 4, 8 and 20 µl of a solution containing 25 ng/µl Lambda DNA (Life Technologies®) on a 1% TBE (Invitrogen®) agarose gel (Roche®) containing ethidiumbromide (ICN Biochemicals®).
- 100-200 ng of BAC clone DNA and 1.7 µg genomic DNA were digested with restriction enzyme EcoRI in a final reaction volume of 20 µl, applying conditions proposed by the manufacturer (New England Biolabs). The time of digestion and/or amount of restriction enzyme were adjusted to ensure complete digestion of the genomic DNA samples without non-specific degradation.
- After digestion, 2 µl of loading dye containing RNase (12.5 ml 1% xylene cyanol FF; 12.5 ml 1% bromophenol blue water soluble indicator; 25 ml glycerol; 100 µl 0.5M EDTA pH8; 1 µl RNase (10 mg/ml)) was added to the digested DNA samples and the samples were incubated for 30 min at 37° C.
- The samples were loaded on a 1% TAE agarose gel.
- Phage Lambda DNA (Fermentas®) digested with PstI or 1 kbp DNA Ladder (Life Technologies) was included as size standard.
- After electrophoresis, the DNA samples (digested BAC clone and genomic DNA) were transferred to a nylon membrane (Hybond-N+ Amersham Pharmacia Biotech®) by dry alkali capillary blotting.
- The nylon membranes with digested BAC clone and genomic DNA were screened by standard Southern hybridization procedures as described above for the BAC library screenings, except that for the genomic DNA the Kodak XOMAT AR films were exposed to the radioactive blots for 2 days at −70° C.
- Based on a comparison between the hybridization patterns obtained after digestion of BAC clone DNA of the identified positive colonies and of genomic DNA isolated from *Brassica napus* with restriction enzyme EcoRI and hybridization with the probes, the BAC clones were grouped in 2 groups and for each of the 2 groups a BAC clone was selected containing a full-length IND sequence (named IND-A1 and IND-C1).
- The IND sequences comprised in the BAC clones of the selected positive colonies were determined by standard sequencing techniques (Agowa).

TABLE 3

Hybridization pattern of digested BAC clone and genomic DNA hybridized to the Bn1- and Bn2-IND probes

| | DNA sample: | | |
|---|---|---|---|
| restricted with: | Genomic DNA from *B. napus* Estimated length | BAC clone DNA from *B. napus* of the hybridizing | Corresponds to DNA fragments: |
| EcoRI | 8 kb | 8 kb | IND-A1 |
| | 2.2 kb | 2.2 kb | IND-C1 | described in Vos et al. (1995, NAR 23:4407-4414) and in published EP patent application EP 534858.

Example 2

Characterization of IND Gene Sequences from *Brassica napus*

After sequencing the genomic DNA fragments (SEQ ID NO: 5 and 7, respectively), the coding regions of the IND sequences were determined with FgeneSH (Softberry, Inc. Mount Kisco, N.Y., USA) and est2genome (Rice et al., 2000, Trends in Genetics 16 (6): 276-277; Mott, 1997, Comput. Applic. 13:477-478) as depicted in the sequence listing.

Comparison of hybridizing bands generated in a Southern blot analysis on genomic DNA isolated from *B. rapa* (AA), *B. oleracea* (CC) and *B. napus* (AACC) and on BAC clone DNA isolated from the positive colonies identified in Example 1 (restricted with EcoRI and hybridized to probe as described in Example 1) indicated that the IND-A1 sequence originated from the A genome and the IND-C1 sequence from the C genome.

The protein encoding regions of the IND genes of the elite spring oilseed rape breeding line are represented in SEQ ID NO:1 (IND-A1), SEQ ID NO:3 from the nucleotide at position 46 to the nucleotide at position 633 (IND-C1-short) and SEQ ID NO:3 (IND-C1-long), respectively. The, by these nucleic acid sequence encoded, IND-A1 and IND-C1 protein sequences are depicted in SEQ ID NO:2 (IND-A1), SEQ ID NO:4 from the amino acid at position 16 to the amino acid at position 210 (IND-C1-short) and SEQ ID NO:4 (IND-C1-long), respectively.

The percentage (nucleotide) sequence identity between the complete coding regions of IND-A1 and IND-C1-long is 81% and between the complete coding regions of IND-A1 and IND-C1-short is 87%, while the percentage (nucleotide) sequence identity between the regions encoding the bHLH domains of IND-A1 and IND-C1-long and -short (as determined according to Toledo-Ortiz et al., 2003, Plant Cell 15, 1749-1770) is 98%. These percentages indicate that the IND genes are more conserved in the region encoding the bHLH domain than in the remaining part of the coding region.

Similarly, the percentage (amino acid) sequence identity between the complete IND-A1 and IND-C1-long proteins is 75% and between the complete IND-A1 and IND-C1-short proteins is 80%, while the percentage (amino acid) sequence identity between the bHLH domains of IND-A1 and IND-C1-long and -short (as determined according to Toledo-Ortiz et al., 2003, Plant Cell 15, 1749-1770) is 98%. These percentages indicate that the IND proteins are more conserved in the bHLH domain than in the remaining part of the IND proteins.

Example 3

Expression of *Brassica* IND Genes

To analyze the expression of the different IND genes in different tissues, RT-PCR assays specific for each IND gene were performed on total RNA isolated from *Brassica napus* leaves, pod walls, dehiscence zone tissue and seeds using the following primers:

```
INDA1F1
5' AGGAGAGGAAGAGATGGATCC 3'        (SEQ ID No. 37)

INDA1R1
5' TGAGTGTGAGGCTGAAGAAGC 3'        (SEQ ID No. 38)
for the IND-A1 gene, and INDC1F1
5' CCTCATCATCTCCTTATGAAC 3'        (SEQ ID No. 39)

INDC1R
5' CGTATTGCATCTCCTTCATCT 3'.       (SEQ ID No. 40)
for the IND-C1 gene.
```

The results indicated that both IND genes, i.e. IND-A1 and IND-C1, were not expressed in leaf tissue and seeds, but were expressed in dehiscence zone tissue and that the IND-A1 gene was expressed in pod walls, while the IND-C1 gene was not expressed in pod walls.

Example 4

Generation and Isolation of Mutant IND Alleles (ind)

Mutations in the IND genes identified in Example 1 were generated and identified as follows:

- 30,000 seeds from an elite spring oilseed rape breeding line (M0 seeds) were preimbibed for two hours on wet filter paper in deionized or distilled water. Half of the seeds were exposed to 0.8% EMS and half to 1% EMS (Sigma: M0880) and incubated for 4 hours.
- The mutagenized seeds (M1 seeds) were rinsed 3 times and dried in a fume hood overnight. 30,000 M1 plants were grown in soil and selfed to generate M2 seeds. M2 seeds were harvested for each individual M1 plant.
- Two times 4800 M2 plants, derived from different M1 plants, were grown and DNA samples were prepared from leaf samples of each individual M2 plant according to the CTAB method (Doyle and Doyle, 1987, Phytochemistry Bulletin 19:11-15).
- The DNA samples were screened for the presence of point mutations in the IND genes causing the introduction of STOP codons in the protein-encoding regions of the IND genes or the substitution of amino acids in the IND proteins, particularly in the bHLH domain of the IND proteins, by direct sequencing by standard sequencing techniques (Agowa) and analyzing the sequences for the presence of the point mutations using the NovoSNP software (VIB Antwerp).
- The following mutant IND alleles (ind) were thus identified:

TABLE 4a

| STOP codon and substitution mutations in IND-A1 | | | | | | |
|---|---|---|---|---|---|---|
| Amino acid position | Nucleotide position | Wild type → mutant | Wild type → mutant | M2 Plant | | |
| SEQ ID: 2/6 | SEQ ID: 1 | SEQ ID: 5 codon | amino acid | No. | Allele No. | |
| 122 | 364 | 924 | cag → tag | GLN → STOP (in b) | POSH101, POSH102, POSH103, POSH104 | ind-a1-EMS01, ind-a1-EMS02, ind-a1-EMS03, ind-a1-EMS04 |

TABLE 4a-continued

STOP codon and substitution mutations in IND-A1

| Amino acid position | Nucleotide position | Wild type → mutant | Wild type → mutant | M2 Plant | |
|---|---|---|---|---|---|
| SEQ ID: 2/6 | SEQ ID: 1 | SEQ ID: 5 codon | amino acid | No. | Allele No. |
| 103 | 307 | 867 | gat → aat | ASP → ASN | POSH105 | ind-a1-EMS05 |
| 127 | 380 | 940 | cgt → cat | ARG → HIS (in b) | POSH105 | ind-a1-EMS05 |

TABLE 4b

STOP codon mutations in IND-C1

| Amino acid position | Nucleotide position | Wild type → mutant | Wild type → mutant | M2 Plant | |
|---|---|---|---|---|---|
| SEQ ID: 4/8 | SEQ ID: 3 | SEQ ID: 7 codon | amino acid | No. | Allele No. |
| 50 | 148 | 644 | caa → taa | GLN → STOP | POSH106 | ind-c1-EMS01 |
| 135 | 403 | 899 | cag → tag | GLN → STOP (in b) | POSH108 | ind-c1-EMS03 |

Reference seeds of plants comprising alleles ind-a1-EMS01 and ind-c1-EMS01 in homozygous state have been deposited at the American Type Culture Collection (ATCC, 10801 University Boulevard, Manassas, Va. 20110-2209, US) on Nov. 20, 2007, under accession number PTA-8796 (strain designation 07 MBBN001171) and reference seeds of plants comprising alleles ind-a1-EMS05 and ind-c1-EMS03 in homozygous state have been deposited at the ATCC on Nov. 20, 2007, under accession number PTA-8795 (strain designation 07 MBBN000530). The deposits were pursuant to the Budapest Treaty.

In conclusion, the above examples show how mutant IND alleles can be generated and isolated. Also, plant material comprising such mutant alleles can be used to combine selected mutant and/or wild type alleles in a plant, as described in the following examples.

Example 5

Identification of a *Brassica* Plant Comprising a Mutant *Brassica* IND Allele

*Brassica* plants comprising the mutations in the IND genes identified in Example 4 were identified as follows:
For each mutant IND gene identified in the DNA sample of an M2 plant, at least 50 M2 plants derived from the same M1 plant as the M2 plant comprising the IND mutation were grown and DNA samples were prepared from leaf samples of each individual M2 plant.
The DNA samples were screened for the presence of the identified point IND mutation as described above in Example 4.
Heterozygous and homozygous (as determined based on the electropherograms) M2 plants comprising the same mutation were selfed and M3 seeds were harvested.

Example 6

Analysis of the Fruit Dehiscence Properties of *Brassica* Plants Comprising a Mutant *Brassica* IND Gene To determine the correlation between the presence of mutant IND genes in *Brassica* plants and the fruit dehiscence properties of the *Brassica* plants, the fruit dehiscence properties of *Brassica* plants comprising a mutant IND gene were analyzed in the glass house and in the field as follows:
To examine whether and how the fruit valve margins and the dehiscence properties of seed pods were affected by mutations in IND, ind fruit was compared to wild-type fruit using the following macroscopic tests:
(a) Inspection of the seed pods and plants in general with naked eye to determine differences in the phenotype of the pods and plants caused by the presence of certain mutant IND alleles. Determination of the phenotype of the pods: When the pods were fully grown and filled, just prior to yellowing, the degree of sharpness of the zone that delineates the valve and beak at the zone where both valves are not touching anymore (at distal end of pod) of 5 random pods (from different plants if multiple plants per line are available) wes assessed and attributed a score from 1 to 5:1 for a clear indentation and fine sharp zone that separates valve and beak; 2 for some indentation and clear, though more fuzzy, zone that separates valve from beak; 3 for valves and beak that are still well observable as two different tissues but with a very smooth transition between them; 4 for valves and beak that are barely observable as different tissues; 5 for a completely smoothened transition between valves and beak without any clear differentiation between both tissue types, i.e. the less indentation between the valve and the beak at the distal end of the pods the higher the score. A score of 1 (sharp indentation between the valve and the beak) corresponds to a wildtype phenotype of the pods, more specifically a pod shatter sensitive phenotype of the pods; a score of 2 to 4 (more gradual transition between the valve and the beak) corresponds to a pod shatter resistant phenotype of the pods, wherein seed shattering is significantly reduced or delayed while an agronomically relevant treshability of the pods is maintained, such that the pods may still be opened along the dehiscence zone by applying limited physical forces; and a score of 5 (no indentation between the valve and the beak) corresponds to a pod shatter resistant phenotype of the pods, wherein seed shattering is reduced or delayed to a degree which does not allow an agronomically relevant treshability of the pods anymore, such that the pods cannot be opened along the dehiscence zone by applying limited physical forces.

(b) Manual Impact Test (MIT) to determine the increase in pod shatter resistance caused by the presence of certain mutant IND alleles: The level of pod shatter resistance of *Brassica* lines comprising the mutant IND alleles and *Brassica* lines comprising the corresponding wild type IND alleles was compared in a semi-quantitative way by determining the physical forces needed to open closed mature pods by manually applying torsion on the pods. A distinction was made between pods which completely open along the dehiscence zone at the slightest torsion, pods which open only at the base of the dehiscence zone and need stronger torsion to open completely and pods which can only be crushed and do not open along the dehiscence zone. The pod shatter resistance of the pods was attributed a score from 1 to 5 based on this physical force: 1 for pods which completely open along the dehiscence zone at the slightest torsion, 2-4 for pods which open only at the base of the dehiscence zone and need stronger torsion to open completely and 5 for pods which can only be crushed and do not open along the dehiscence zone.

(c) Random Impact Test (RIT) to determine the increase in pod shatter resistance caused by the presence of certain mutant IND alleles: The level of pod shatter resistance of *Brassica* lines comprising the mutant IND alleles and *Brassica* lines comprising the corresponding wild type IND alleles was compared in a quantitative way by determining the half life of samples of pods from both lines according to Bruce et al. (2002, supra). More specifically, two replicate samples of 20 intact mature pods from each line were subjected to a RIT. 20 pods were placed together with six steel balls of 12.5 mm diameter in a cylindrical container of diameter 20 cm with its axis vertical. The container was then subjected to simple harmonic motion of frequency 4.98 Hz and of stroke 51 mm in the horizontal plane. The pods, checked for soundness before the test, were shaken for cumulative times of 10, 20, 40, and, if more than 50% of pods remained intact, 80 s. The drum was opened after each period and the number of closed pods counted. The pods were examined and classed as "closed" if the dehiscence zone of both valves was still closed. Thus the pods were classed as "opened" if one or both of the valves was detached, so that the seed had been released. If the majority of the pods was broken or damaged without opening of the dehiscence zone, the sample was marked "uncountable". To give each point equal weighing, the data were made evenly spaced in the independent variable, time, by adding 1 and taking $\log_{10}$. The percentage of pods opened p was transformed by the logit transformation, i.e. logit $p=\log_e(p/100-p)$. A linear model was then fitted to the transformed time and percentage data and used to estimate the half-life.

(d) Field tests to determine the relationship between pod shatter resistance, treshability and yield and the presence of certain mutant IND alleles in plants: The level of pod shatter resistance, treshability and yield of *Brassica* lines comprising the mutant IND alleles and *Brassica* lines comprising the corresponding wild type IND alleles was compared in a semi-quantitative way by determining and comparing the level of seed shattering (SHAT), combiner harvest ability (CHA1) and treshing ability (CHA2) and in a quantitative way by determining and comparing seed yield per plot after combining (YLDP) and seed yield after treshing of straw (YLDS) in the field between plots with ind plants and plots with wild-type plants. The plots were attributed a score of 1-9 to indicate the level of seed shattering on the plot before harvest: a score of 1 to indicate that practically all plants on the plot were shattering before harvest to a score of 9 to indicate that practically no plants on the plot were shattering before harvest. The plots were attributed a score of 1-5 to indicate the level of combiner harvest ability on the plot: a score of 1, to 3 or to 5 to indicate that it was difficult, to feasible, or to easy, respectively, to harvest the plot with a combiner. The plots were attributed a score of 1-5 to indicate the level of treshing ability of the plot: a score of 1, to 3 or to 5 to indicate that it was difficult, to feasible, or to easy, respectively, to manually harvest the seed remaining in the straw after combiner harvest. The seed yield per plot after combining (YLDP; expressed in grams per plot) was determined by harvesting the seeds per plot with a combine harvester and weighing the seeds and the seed yield after treshing of straw (YLDS; expressed in weight % of the straw) was determined by manually harvesting the seeds remaining in the straw after seed harvest with the combine harvester.

To examine more closely whether and how cells at the valve margin of seed pods are affected by mutations in IND, sections of ind fruit were compared to sections of wild-type fruit by microscopic evaluation of the seed pods:

Explants: Explants of about 3 mm taken from the proximal and distal ends of pods of similar developmental stage (about 35 days after anthesis (DAA), a stage of development which closely corresponds to the onset of visible pericarp yellowing) and size were harvested from plants grown in a plant growth room (two pods for each genotype) and/or in the field. Both dehiscence zones were dissected from the pods.

Fixation: Fixation was done in 100 mM K-phosphate buffer pH7 with 10% formalin and 0.25% glutaraldehyde for a total of 4 hours. Vacuum infiltration was done after 1 and 2 hours for 15 minutes. The fixative was renewed after each vacuum infiltration.

Dehydration: The specimen was rinsed 2 times 30 minutes with 100 mM K-phosphate buffer pH7. Dehydration was done with technical ethanol diluted with 0.85% NaCl in water: 60 minutes (') in 50% ethanol, 90' in 70% ethanol, 90' in 80% ethanol, 90' in 90% ethanol, 90' in 95% ethanol, 90' in 100% ethanol at room temperature Embedding: Embedding was done with The Leica 7022-31731 Historesin or the Kulzer Histo-Technik 7100 (Heraeus) embedding kits, which are three component resin (a basic resin, an activator and a hardener) kits. The three components were used in the proportions as advised by the manufacturer as follows: the specimen were incubated for 4 hours in 50% ethanol/50% basic resin, overnight in 30% ethanol/70% basic resin (optional: at 4° C.), for 2 to 4 hours in 100% basic resin, for one day in 100% basic resin after renewing the basic resin and vacuum infiltration for 20' (optionally at 4° C.), for one day in basic resin+activator (1%) ("infiltration medium")

after vacuum infiltration in this medium for 20 minutes. The specimen was washed with basic resin+activator (1%)+hardener (1 ml in 15 ml) ("embedding medium"). The embedding was done in flat embedding moulds (AGAR flat embedding moulds G3531 with cavities of about 300 µl: 14 mm long×6 mm wide×4 mm deep): 100-125 µl of embedding medium/cavity was added, the embedding medium was polymerized at 55° C. for about one hour, the tissue was put on the polymerized embedding medium (1 explant/cavity), the cavities ware filed with embedding medium, the embedding medium was polymerized for 3 to 5 hours at 55° C., the moulds were could down, the plastic blocks were POSH105 and POSH106 and heterozygous M2 plants No. POSH105; see Table 4a and b for the corresponding ind alleles) were grown in the glass house and analyzed as described above. No significant difference in phenotype and fruit dehiscence properties was observed between wild type plants and these heterozygous and homozygous single mutant plants.

Field tests with homozygous single ind mutant (genotype: ind-a1/ind-a1, IND-C1/IND-C1 or ind-c1/ind-c1) and wild type plants (genotype: IND-A1/IND-A1, IND-C1/IND-C1) from segregating backcross 3 (BC3) populations showed however an increase in seed yield for the homozygous single ind mutant plants (see Table below).

| Genotype | SHAT (1-9) | CHA1 (1-5) | CHA2 (1-5) | YLDP (in g/plot) | YieldWTSeg % | YLDS (in wt % of straw) |
|---|---|---|---|---|---|---|
| ind-a1-01/ind-a1-01, IND-C1/IND-C1 | 8.0 | 4.9 | 5.0 | 2636.0 | 106 | 0.8 |
| IND-A1/IND-A1, IND-C1/IND-C1 | 7.8 | 4.9 | 5.0 | 2490.0 | 100 | 0.7 |
| ind-a1-05/ind-a1-05, IND-C1/IND-C1 | 8.1 | 4.8 | 5.0 | 2450.9 | 103 | 0.3 |
| IND-A1/IND-A1, IND-C1/IND-C1 | 7.6 | 5.0 | 4.8 | 2387.6 | 100 | 0.4 |
| IND-A1/IND-A1, ind-c1-01/ind-c1-01 | 8.3 | 4.9 | 5.0 | 2856.0 | 113 | 0.6 |
| IND-A1/IND-A1, IND-C1/IND-C1 | 8.3 | 4.8 | 5.0 | 2517.3 | 100 | 0.3 |
| IND-A1/IND-A1, ind-c1-03/ind-c1-03 | 8.6 | 4.7 | 4.9 | 2833.6 | 113 | 0.5 |
| IND-A1/IND-A1, IND-C1/IND-C1 | 8.1 | 4.6 | 5.0 | 2510.7 | 100 | 0.4 | removed from the moulds and stored at room temperature in a sealed container (e.g. eppendorf tube).

Sectioning: The plastic blocks were glued with the flat side on a 1 cm³ perpex block and trimmed squarely around the specimen. 4 µm sections (3 to 4 explants per genotype, about 25 sections per explant) were cut with a ralph glass knife (made on −1 position of the histoknifemaker of Reichert-Jung using 6 mm thick glass rods under a cutting angle of about)$_6$° on the microtome. The sections were attached on glass slides treated with Vectabond (Vector laboratories).

Demonstration of lignin: unstained sections mounted in Eukitt were examined using a microscope equipped for fluorescence (with Zeiss filter set 02). Lignin fluoresces clear bluish Evaluation of histology: unstained sections were visualized by using DIC-Normaski or autofluorescence (with Zeiss filter set 18-Excitation BP390-420; Emission LP450).

6.1. Correlation Between the Presence of One or Two Mutant *Brassica* IND Alleles in *Brassica* Plants and the Fruit Dehiscence Properties of Those *Brassica* Plants To determine the correlation between the presence of one ind in heterozygous state (genotype: IND-A1/ind-a1, IND-C1/IND-C1; or IND-A1/IND-A1, IND-C1/ind-c1) or in homozygous state (genotype: ind-a1/ind-a1, IND-C1/IND-C1 or IND-A1/IND-A1, ind-c1/ind-c1) in a *Brassica* plant and the fruit dehiscence properties of the *Brassica* plant, the fruit dehiscence properties of *Brassica* plants identified in Example 5 (in particular homozygous M2 plants No. POSH101, POSH103, POSH104, 6.2. Correlation Between the Presence of at Least Three Mutant *Brassica* IND Alleles in *Brassica* Plants and the Fruit Dehiscence Properties of Those *Brassica* Plants To determine the correlation between the presence of at least three mutant IND alleles in a *Brassica* plant and the fruit dehiscence properties of the *Brassica* plant, the *Brassica* plants identified in Example 5, and/or progeny thereof, comprising the mutant IND alleles, were crossed with each other and the fruit dehiscence properties of the progeny *Brassica* plants was analyzed as described above.

Plant Material:

Progeny (i.e., homozygous double mutant plants with genotype ind-a1/ind-a1, ind-c1/ind-c1; homozygous single and heterozygous single—i.e., triple-mutant plants with genotype ind-a1/ind-a1, IND-C1/ind-c1 and IND-A1/ind-a1, ind-c1/ind-c1; and wild type plants with genotype IND-A1/IND-A1, IND-C1/IND-C1) of line 51, line 45, line 176 and line 48, which themselves are heterozygous (genotype: IND-A1/ind-a1, IND-C1/ind-c1) for alleles IND-A1-EMS01 and IND-C1-EMS01 (line 51), alleles IND-A1-EMS01 and IND-C1-EMS03 (line 45), alleles IND-A1-EMS05 and IND-C1-EMS01 (line 176), and alleles IND-A1-EMS05 and IND-C1-EMS03 (line 48), respectively.

Macroscopical Evaluation:

a) Inspection of the Seed Pods and Plants with Naked Eye.

The pods from double homozygous mutant IND sibling plants (genotype: ind-a1/ind-a1, ind-c1/ind-c1) derived from lines 51, 45, 176 and 48 showed an altered pod morphology, already at immature stage, as compared to pods from wild-type IND sibling plants. More specifically, the pods of the double homozygous mutant IND sibling plants showed a lack of proper valve margin definition, particularly apparent at both the proximal and distal end of the fruit, as compared to the pods from wild-type IND sibling plants, which showed clearly defined margins. Furthermore, the sharp indentation between the valve and the beak at the distal end of the pods in the wild-type sibling plants was largely absent in the double homozygous ind sibling plants, which showed a more gradual transition between valve and beak tissue. The flowers of the double homozygous mutant IND sibling plants of line 51 sometimes displayed deformed petals under greenhouse conditions. Furthermore, the pods from plants derived from line 45 were in general smaller than the pods from plants derived from the other lines. Since this size difference occurred in both wild-type and mutant ind sibling plants derived from line 45, it is probably caused by a background mutation in this line.

The pods from plants comprising one ind allele in homozygous state and one ind allele in heterozygous state (genotype: ind-a1/ind-a1, IND-C1/ind-c1 or IND-A1/ind-a1, ind-c1/ind-c1) showed an intermediate phenotype. More specifically, the valve margins of the pods of these mutant IND sibling plants were in general better defined than in the double homozygous mutant IND sibling plants, but the sharp indentation between the valve and the beak at the distal end of the pods in the wild-type sibling plants was still largely absent in these mutant plants.

Table 5a shows the visual pod scores attributed to the phenotype of the pods from plants grown in the field as described above:

TABLE 5a

| Genotype | Line n° | visual pod score (1-5) |
|---|---|---|
| IND-A1/IND-A1, IND-C1/IND-C1 | 51 | 1 |
| | 45 | 1 |
| | 176 | 1 |
| | 48 | 1 |
| ind-a1/ind-a1, IND-C1/ind-c1 | 51 | 3 |
| | 45 | 3 |
| | 176 | 2 |
| | 48 | 3 |
| IND-A1/ind-a1, ind-c1/ind-c1 | 51 | 3 |
| | 45 | 3 |
| | 176 | 2 |
| | 48 | 3 |
| ind-a1/ind-a1, ind-c1/ind-c1 | 51 | 5 |
| | 45 | 5 |
| | 176 | 4 |
| | 48 | 5 | b) Manual Impact Test (MIT):

The pods from plants comprising two mutant IND alleles in homozygous state (genotype: ind-a1/ind-a1, ind-c1/ind-c1) derived from lines 51, 45, 176 and 48 were completely pod shatter resistant (pods did not open along the dehiscence zone even after applying a strong torsion).

The pod shatter resistance of pods from plants comprising one ind allele in homozygous state and one ind allele in heterozygous state (genotype: ind-a1/ind-a1, IND-C1/ind-c1 or IND-A1/ind-a1, ind-c1/ind-c1) was increased as compared to the pod shatter resistance of pods from their wild-type sibling plants, but the pods could still be opened along the dehiscence zone after applying limited physical forces.

Table 5b shows the scores attributed to the pods from plants grown in the field based on the physical force needed to open closed mature pods by manually applying torsion on the pods as described above:

TABLE 5b

| Genotype | Line n° | Score based on physical force needed to open closed mature pods (1-5) |
|---|---|---|
| IND-A1/IND-A1, IND-C1/IND-C1 | 51 | 1 |
| | 45 | 1 |
| | 176 | 1 |
| | 48 | 1 |
| ind-a1/ind-a1, IND-C1/ind-c1 | 51 | 3 |
| | 45 | 3 |
| | 176 | 1 |
| | 48 | 2 |
| IND-A1/ind-a1, ind-c1/ind-c1 | 51 | 3 |
| | 45 | 2 |
| | 176 | 1 |
| | 48 | 3 |
| ind-a1/ind-a1, ind-c1/ind-c1 | 51 | ND |
| | 45 | ND |
| | 176 | ND |
| | 48 | ND |

ND: not determined c) Random Impact Test:

As shown in Table 5c, the half life of pod samples ('LD50') was significantly higher for pods from homozygous double mutants (genotype ind-a1/ind-a1, ind-c1/ind-c1) derived from line 51 than for pods of homozygous double mutants derived from line 45, indicating that homozygous double mutant plants comprising the IND-C1-EMS01 allele (line 51) were more pod shatter resistant than homozygous double mutant plants comprising the IND-C1-EMS03 allele (line 45).

Table 5c further shows that the LD50 value was in general higher for pods from plants comprising one ind-c1 allele in homozygous state and one ind-a1 allele in heterozygous state (genotype: IND-A1/ind-a1, ind-c1/ind-c1) than for pods from plants comprising one ind-a1 allele in homozygous state and one ind-c1 allele in heterozygous state (genotype: ind-a1/ind-a1, IND-C1/ind-c1) indicating that the mutations in the IND-C1 allele could have a stronger effect on pod shatter resistance than the mutations in the IND-A1 allele.

TABLE 5c

| Genotype | Line n° | LD50-glasshouse | | LD50-field1 | LD50-field2 |
|---|---|---|---|---|---|
| | | Lower 95% | Upper 95% | | |
| IND-A1/IND-A1, IND-C1/IND-C1 | 51 | 8.61 | 6.56 | 11.08 | 8.9 | 6.8 |
| | 45 | 8.07 | 6.08 | 10.45 | 7.8 | 5.7 |
| | 176 | ND | | | 5.3 | 5.3 |
| | 48 | 11.42 | 7.42 | 14.9 | 9 | 5.3 |

TABLE 5c-continued

| Genotype | Line n° | LD50-glasshouse | | LD50-field1 | LD50-field2 |
|---|---|---|---|---|---|
| | | Lower 95% | Upper 95% | | |
| | 48 | 8.86 | * | * | |
| ind-a1/ind-a1, IND-C1/IND-C1 | 48 | 9.86 | 5.89 | 13.3 | ND | ND |
| IND-A1/IND-A1, ind-c1/ind-c1 | 48 | 5.98 | 2.87 | 8.6 | ND | ND |
| ind-a1/ind-a1, IND-C1/ind-c1 | 51 | 14.22 | 11.33 | 17.79 | 21.1 | 21.4 |
| | 51 | 22.78 | 18.68 | 27.8 | | |
| | 45 | 14.97 | 11.95 | 18.74 | 22.9 | 24.6 |
| | 45 | 10.32 | 8.05 | 13.05 | | |
| | 176 | ND | | | 7.3 | 8.6 |
| | 48 | 7.21 | 3.04 | 9.7 | 10.1 | 9.4 |
| IND-A1/ind-a1, ind-c1/ind-c1 | 51 | 48.31 | 39.94 | 58.73 | 16.9 | 22.6 |
| | 51 | 46.46 | 38.44 | 56.41 | | |
| | 45 | 26.89 | 22.03 | 32.95 | 20.6 | 14.6 |
| | 45 | 17.5 | 13.96 | 22.01 | | |
| | 176 | ND | | | 10.9 | 8.0 |
| | 48 | 30.14 | 25.49 | 36.8 | 18.3 | 16.5 |
| ind-a1/ind-a1, ind-c1/ind-c1 | 51 | 163.28 | 116.12 | 237.62 | ND | ND |
| | 45 | 73.57 | 53.85 | 103.54 | ND | ND |
| | 176 | ND | | | ND | ND |
| | 48 | 115.99 | 66.35 | 523.4 | ND | ND |

* Insufficient data available to estimate the upper and lower bounds to LD50 d) Field Tests

Table 5d shows the level of seed shattering (SHAT), combiner harvest ability (CHA1), treshing ability (CHA2), seed yield per plot after combining (YLDP) and seed yield after treshing of straw (YLDS) determined as described above for field plots with ind plants and wild-type plants as indicated. The YieldWTSeg % value represents the YLDP as a percentage of the wildtype segregant within one line, i.e. within line 51, 45, 176 or 48, respectively.

TABLE 5d

| Genotype | Line n° | SHAT (1-9) | CHA1 (1-5) | CHA2 (1-5) | YLDP (in g/plot) | YieldWTSeg % | YLDS (in wt % of straw) |
|---|---|---|---|---|---|---|---|
| IND-A1/IND-A1, IND-C1/IND-C1 | 51 | 8.1 | 4.9 | 5.0 | 2154.7 | 100 | 0.6 |
| | 45 | 8.4 | 4.2 | 4.8 | 1868.7 | 100 | 0.8 |
| | 176 | 8.1 | 4.6 | 5.0 | 1710.2 | 100 | 0.3 |
| | 48 | 7.9 | 4.7 | 5.0 | 1844.2 | 100 | 0.5 |
| ind-a1/ind-a1, IND-C1/ind-c1 | 51 | 8.9 | 2.9 | 3.8 | 2450.7 | 114 | 4.5 |
| | 45 | 8.8 | 2.3 | 3.3 | 2304.2 | 123 | 7.6 |
| | 176 | 8.7 | 3.9 | 4.9 | 2189.6 | 128 | 0.6 |
| | 48 | 8.8 | 4.1 | 4.9 | 2419.1 | 131 | 1.4 |
| IND-A1/ind-a1, ind-c1/ind-c1 | 51 | 8.9 | 3.3 | 4.3 | 2739.6 | 127 | 1.9 |
| | 45 | 8.8 | 2.6 | 3.4 | 2441.6 | 131 | 3.4 |
| | 176 | 8.7 | 4.1 | 4.9 | 2071.6 | 121 | 0.7 |
| | 48 | 8.8 | 3.6 | 4.1 | 2379.8 | 129 | 2.4 |
| ind-a1/ind-a1, ind-c1/ind-c1 | 51 | 9.1 | 1.2 | 2.0 | 515.3 | 24 | 27.4 |
| | 45 | 9.0 | 1.0 | 2.0 | 424.4 | 23 | 27.4 |
| | 176 | 9.0 | 1.1 | 2.6 | 702.4 | 41 | 21.0 |
| | 48 | 9.0 | 1.0 | 1.9 | 447.3 | 24 | 27.7 |

Microscopical Evaluation:

Pods from plants comprising two ind alleles in homozygous state derived from line 45 (genotype ind-a1/ind-a1, ind-c1/ind-c1) grown under greenhouse conditions showed a lignification throughout the complete dehiscence zone and a poor differentiation of cells belonging to the dehiscence zone from neighboring cell types, such as the vascular tissue cells and the lignified layer of cells normally found at the inner pod wall (i.e. the enb cells) ("strong morphological phenotype"). A similar pod phenotype was observed for these plants grown under field conditions. By contrast, the dehiscence zones were still well differentiated and mostly non-lignified in pods from plants comprising two ind alleles in homozygous state derived from line 51 (genotype ind-a1/ind-a1, ind-c1/ind-c1) grown under greenhouse conditions but the dehiscence zones did show extra lignification where the pod walls come together ("weaker morphological phenotype"). Pods from these plants grown under field conditions showed a lignification pattern similar to that of pods from plants with genotype IND-A1/ind-a1, ind-c1/ind-c1 derived from line 45 described below. When combined with the data obtained from the RIT, these data could indicate that these plants combine a "weaker morphological phenotype" with a higher pod shatter resistance.

Pods from plants comprising one ind allele in homozygous state and one ind allele in heterozygous state derived from lines 45 and 51 (genotype: ind-a1/ind-a1, IND-C1/ind-c1 or IND-A1/ind-a1, ind-c1/ind-c1) grown under greenhouse conditions did not show an obvious phenotype. Under field conditions, pods from plants with genotype IND-A1/ind-a1, ind-c1/ind-c1 derived from lines 45 displayed a more subtle morphological phenotype than pods from plants of their homozygous double mutant siblings (see above). More specifically, lignification did not occur throughout the complete dehiscence zone but the pods of these plants only displayed a few extra layers of lignified cells where the inner pod wall is attached to the septum, either symmetrically at both sides of the septum or only unilaterally. A similar pod phenotype was observed for pods from plants with genotype IND-A1/ind-a1, ind-c1/ind-c1 derived from lines 51 grown under field conditions. Pods from plants with genotype ind-a1/ind-a1, IND-C1/ind-c1 derived from lines 45 and 51 did not show an obvious phenotype under field conditions.

Example 7

Detection and/or Transfer of Mutant IND Genes into (Elite) *Brassica* Lines

The mutant IND genes are transferred into (elite) *Brassica* breeding lines by the following method: A plant containing a mutant IND gene (donor plant), is crossed with an (elite) *Brassica* line (elite parent/recurrent parent) or variety lacking the mutant IND gene. The following introgression scheme is used (the mutant IND gene is abbreviated to ind while the wild type is depicted as IND):
Initial cross: ind/ind (donor plant)×IND/IND (elite parent)
F1 plant: IND/ind
BC1 cross: IND/ind×IND/IND (recurrent parent)
BC1 plants: 50% IND/ind and 50% IND/IND
  The 50% IND/ind are selected using molecular markers (e.g. AFLP, PCR, Invader™, and the like; see also below) for the mutant IND allele (ind).
BC2 cross: IND/ind (BC1 plant)×IND/IND (recurrent parent)
BC2 plants: 50% IND/ind and 50% IND/IND
  The 50% IND/ind are selected using molecular markers for the mutant IND allele (ind).
Backcrossing is repeated until BC3 to BC6
BC3-6 plants: 50% IND/ind and 50% IND/IND
  The 50% IND/ind are selected using molecular markers for the mutant IND allele (ind). To reduce the number of backcrossings (e.g. until BC3 in stead of BC6), molecular markers can be used specific for the genetic background of the elite parent.
BC3-6 S1 cross: IND/ind×IND/ind
BC3-6 S1 plants: 25% IND/IND and 50% IND/ind and 25% ind/ind
  Plants containing ind are selected using molecular markers for the mutant IND allele (ind). Individual BC3-6 S1 plants that are homozygous for the mutant IND allele (ind/ind) are selected using molecular markers for the mutant and the wild-type IND alleles. These plants are then used for seed production.

To select for plants comprising a point mutation in an IND allele, direct sequencing by standard sequencing techniques known in the art, such as those described in Example 4, can be used. Alternatively, PCR assays can be developed to discriminate plants comprising a specific point mutation in an IND allele from plants not comprising that specific point mutation. The following discriminating PCR assays were thus developed to detect the presence or absence and the zygosity status of the mutant alleles identified in Example 4 (see Table 4):

Template DNA:
  Genomic DNA isolated from leaf material of homozygous or heterozygous mutant *Brassica* plants (comprising a mutant IND allele, called hereinafter "IND-Xx-EMSXX").
  Wild type DNA control: Genomic DNA isolated from leaf material of wild type *Brassica* plants (comprising the wild type equivalent of the mutant IND allele, called hereinafter "IND-Xx-WT").
  Positive DNA control: Genomic DNA isolated from leaf material of homozygous mutant *Brassica* plants known to comprise IND-Xx-EMSXX.
Primers and length of the fragment amplified from the mutant and corresponding wild-type target IND gene are indicated in Table 6. Generally, each primer set consists of one primer specific for the mutant and the wild type target gene (e.g. primer POSH101R2 is specific for IND-A1-EMS01 and IND-A1-WT) and one primer specific for the nucleotide difference (e.g. primer POSH101MF1 is specific for the IND-A1-EMS01 and primer POSH101WF1 is specific for IND-A1-WT). Usually, the last nucleotide of the latter primer matches with the nucleotide difference (underlined nucleotide in Table 6), but one (or more) additional target specific nucleotide(s) may be added to improve the annealing between the primer and its target sequence (see e.g. bold nucleotide in primer POSH 108MR1', which is specific for the IND-C1-EMS03 allele, as compared to primer POSH 108WR1', which is specific for the IND-C1-WT allele).
PCR mix: 2.5 µl 10×PCR buffer (15 mM MgCl2), 0.25 µl dNTP's (20 mM), 1 µl forward primer (10 µM), 1 µl reverse primer (10 µM), 0.25 µl Taq-polymerase (5 U/µl), 19.5 µl Milli-Q H$_2$O, 0.5 µl DNA (20-50 ng/µl) =Total volume of 25 µl;
Thermocycling profile: 4 min at 95° C.; 30×[1 min at 95° C. (denaturation) and 1 min at annealing temperature specified in Table 6 and 2 min at 72° C. (elongation)]; 5 min at 72° C.; cool down to 4° C. The optimal annealing temperature was determined by temperature gradient PCR wherein the annealing temperature was varied between 57° C. to 70° C. on a MJ Research thermocycler PTC-200 (Biozym). The optimal annealing temperature for the wild type IND specific primers is that temperature at which a clear PCR fragment of the expected size can be detected (as described below) for the DNA sample from the wild type *Brassica* plant and not for the DNA sample from the mutant *Brassica* plant. The optimal annealing temperature for the mutant IND specific primers is that temperature at which a clear PCR fragment of the expected size can be detected (as described below) for the DNA sample from the mutant *Brassica* plant and not for the DNA sample from the wild type *Brassica* plant.
After amplification, 5 µl loading dye (orange dye) was added to 15 µl of the PCR samples and the samples were loaded on a 1.5% agarose gel.
The banding patterns obtained after amplification of genomic DNA of mutant *Brassica* plants are evaluated as follows:
  Data from DNA samples isolated from leaf material of the mutant *Brassica* plants within a single PCR run and a single PCR mix should not be accepted unless: the wild-type DNA control shows the PCR fragment of the expected size for the IND-Xx-WT specific PCR assay and no PCR fragment of the expected size for the IND-Xx-EMSXX specific PCR assay the positive DNA control shows the PCR fragment of the expected size for the IND-Xx-EMSXX specific PCR assay and no PCR fragment of the expected size for the IND-Xx-WT specific PCR assay Lanes showing no PCR product of the expected size for the IND-Xx-WT specific PCR assay and the PCR fragment of the expected size for the IND-Xx-EMSXX specific PCR assay, indicate that the corresponding plant from which the genomic template DNA was prepared, is a homozygous mutant for IND-Xx-EMSXX.

Lanes showing the PCR fragment of the expected size for the IND-Xx-WT specific PCR assay and the IND-Xx-EMSXX specific PCR assay, indicate that the corresponding plant from which the genomic template DNA was prepared, is a heterozygous mutant for IND-Xx-EMSXX.

Lanes showing the PCR fragment of the expected size for the IND-Xx-WT specific PCR assay and no PCR product of the expected size for the IND-Xx-EMSXX specific PCR assay, indicate that the corresponding plant from which the genomic template DNA was prepared, is a wild type plant.

Probes specific for the mutant or corresponding wild-type target IND gene (indicated as "5' flap1-x" and "5' flap2-x", respectively) and "invading" probes which can be used in combination with them are indicated in Table 7. Generally, each probe set consists of one probe specific for the mutant or the wild type target gene of which the first nucleotide after the 5' flap sequence matches with the nucleotide difference (underlined nucleotide in Table 7) (the so-called "primary probe"; e.g. the probe with SEQ ID NO: 26 is specific for IND-A1-EMS01 and the probe with SEQ ID NO: 27 is specific for IND-A1-WT) and one probe specific for the nucleotides upstream of the nucleotide difference (the so-called "Invader® oligo"; e.g. the probe with SEQ ID NO: 25 is specific for the nucleotides upstream of the nucleotide difference between IND-A1-EMS01 and IND-A1-WT). The last nucleotide of the latter primer may match with the nucleotide difference in the mutant (as indicated by the bold nucleotides in Table 6), but other nucleotides may be used as well for this last nucleotide as long as the primary probe and the Invader® oligo are still able to form a single base overlap when hybridized to the target DNA to generate the specific invasive structure recognized by the Cleavase® enzymes (Third Wave Agbio).

The Invader™ assay procedure and interpretation of the data are performed as prescribed by the manufacturer (Third Wave Agbio). Briefly, the nucleotide sequences indicated as "flap1" and "flap2" in Table 7 represent the sequences of the 5' "flaps" which are cleaved from the

TABLE 6

| Allele No. | Primers | Annealing t° (° C.) | Size PCR fragment (bp) |
|---|---|---|---|
| IND-A1-EMS01 | 5' AAGGGTAAGCGACGACCCTT 3' (POSH101MF1-SEQ ID NO: 13)<br>5' GAGTGTGAGGCTGAAGAAGC 3' (POSH101R2-SEQ ID NO: 15) | 67 | 191 |
| IND-A1-WT | 5' AAGGGTAAGCGACGACCCTC 3' (POSH101WF1-SEQ ID NO: 14)<br>5' GAGTGTGAGGCTGAAGAAGC 3' (POSH101R2-SEQ ID NO: 15) | 71.1 | 191 |
| IND-A1-EMS05 | 5' CCTCAGACGGTGGTGGCTCA 3' (POSH105MF1-SEQ ID NO: 16)<br>5' AGGGTCAGACATAGGAGCTC 3' (POSH 101R1-SEQ ID NO: 18) | 70 | 201 |
| IND-A1-WT | 5' CCTCAGACGGTGGTGGCTCG 3' (POSH105WF1-SEQ ID NO: 17)<br>5' AGGGTCAGACATAGGAGCTC 3' (POSH 101R1-SEQ ID NO: 18) | 72 | 201 |
| IND-C1-EMS01 | 5' GTGGTTAAAAGAGTTTTCTTA 3' (POSH106MR1-SEQ ID NO: 19)<br>5' ATTAGCATGTAAAACACTAG 3' (POSH106F1-SEQ ID NO: 21) | 60.6 | 436 |
| IND-C1-WT | 5' GTGGTTAAAAGAGTTTTCTTG 3' (POSH106WR1-SEQ ID NO: 20)<br>5' ATTAGCATGTAAAACACTAG 3' (POSH106F1-SEQ ID NO: 21) | 62.8 | 436 |
| IND-C1-EMS03 | 5' ACGAGCCACCACCGTCTAG 3' (POSH 108MR1'-SEQ ID NO: 22)<br>5' GTTCAAAAGCAGATGCAGCAG 3' (POSH106F2-SEQ ID NO: 24) | 70 | 369 |
| IND-C1-WT | 5' ACGAGCCACCACCGTCTG 3' (POSH 108WR1'-SEQ ID NO: 23)<br>5' GTTCAAAAGCAGATGCAGCAG 3' (POSH106F2-SEQ ID NO: 24) | 68.9 | 369 |

Alternatively, Invader™ technology (Third Wave Agbio) can be used to discriminate plants comprising a specific point mutation in an IND allele from plants not comprising that specific point mutation. The following discriminating Invader™ probes were thus developed to detect the presence or absence and the zygosity status of the mutant alleles identified in Example 4 (see Table 7:

primary probes in the primary phase of the Invader™ assay and which are complementary to sequences in FRET™ cassette 1 and 2, respectively, and not complementary to the target mutant or wild type sequences. If the primary probes are cleaved in the primary phase and the flap1-probe and/or flap2-probe hybridise to FRET™ cassette 1 and 2, respectively, in the secondary phase, a signal is generated indicative of the presence in the sample of the mutant or corresponding wild-type target IND gene, respectively.

TABLE 7

| Allele No. | Probes | |
|---|---|---|
| IND-A1-EMS01 | 5' GCCGACGAGCCACCACCGTCTT 3' | (SEQ ID NO: 25) |
|  | 5' flap1-AAGGGTCGTCGCTT 3' | (SEQ ID NO: 26) |
| IND-A1-WT | 5' GCCGACGAGCCACCACCGTCTT 3' | (SEQ ID NO: 25) |
|  | 5' flap2-GAGGGTCGTCGCT 3' | (SEQ ID NO: 27) |
| IND-A1-EMS05 | 5' CGGATCTTCTCGCTTATCCTTTCTCTACGCCAA 3' | (SEQ ID NO: 28) |
|  | 5' flap1-TGAGCCACCACCG 3' | (SEQ ID NO: 29) |
| IND-A1-WT | 5' CGGATCTTCTCGCTTATCCTTTCTCTACGCCAA 3' | (SEQ ID NO: 28) |
|  | 5' flap2-CGAGCCACCACCG 3' | (SEQ ID NO: 30) |
| IND-C1-EMS01 | 5' AGGTGGATCTACCATGAAATGAGGATTGTGGTT AAAAGAGTTTTCTTT 3' | (SEQ ID NO: 31) |
|  | 5' flap1-ATGTAATGAGATCAATAGGTTTG 3' | (SEQ ID NO: 32) |
| IND-C1-WT | 5' AGGTGGATCTACCATGAAATGAGGATTGTGGTT AAAAGAGTTTTCTTT 3' | (SEQ ID NO: 31) |
|  | 5' flap2-GTGTAATGAGATCAATAGGTTTG 3' | (SEQ ID NO: 33) |
| IND-C1-EMS03 | 5' CCGTAACGTAAGGGTAAGCGAGGACCCCA 3' | (SEQ ID NO: 34) |
|  | 5' flap1-TAGACGGTGGTGGC 3' | (SEQ ID NO: 35) |
| IND-C1-WT | 5' CCGTAACGTAAGGGTAAGCGAGGACCCCA 3' | (SEQ ID NO: 34) |
|  | 5' flap2-CAGACGGTGGTGGC 3' | (SEQ ID NO: 36) |

The invention claimed is:

1. An isolated induced full knock-out mutant allele of a gene encoding a functional INDEHISCENT (IND) protein comprising a nucleic acid having the sequence of SEQ ID NO: 3, said full knock-out mutant allele having the sequence of SEQ ID NO: 3 in which the c at position 148 is substituted with t, or in which the c at position 403 is substituted with t.

2. A *Brassica* plant, or a cell, part, seed or progeny thereof, comprising at least two IND genes and comprising only two full knock-out mutant IND alleles in its genome, wherein said full knock-out mutant IND alleles are mutant alleles of a gene encoding a functional INDEHISCENT (IND) protein comprising a nucleic acid that:
(a) has at least 95% sequence identity to the nucleic acid sequence of SEQ ID NO: 3 from the nucleotide at position 46 to the nucleotide at position 633, SEQ ID NO: 3, or SEQ ID NO: 7; or
(b) encodes an amino acid sequence with at least 95% sequence identity to the amino acid sequence of SEQ ID NO: 4 from the amino acid at position 16 to the amino acid at position 210 or SEQ ID NO: 4, and
wherein said full knock-out mutant IND alleles comprise a mutated DNA region comprising one or more inserted, deleted, or substituted nucleotides compared to a corresponding wild-type DNA region in the functional IND gene, and
wherein said full knock-out mutants IND allele are:
(i) a mutant IND allele comprising a mutation resulting in the production of a non-functional IND protein or resulting in no production of an IND protein,
(ii) a mutant IND allele encoding a truncated IND protein of which at least the Helix-Loop-Helix domain at positions corresponding to positions 132 to 174 of SEQ ID NO: 10 is lacking or substituted; and/or
(iii) a mutant IND allele with a missense mutation of the codon encoding the amino acid at a position corresponding to position 128 of SEQ ID NO: 10,
and wherein the plant has increased seed yield compared to the seed yield of a corresponding plant not comprising full knock-out mutant IND alleles.

3. A seed pod obtainable from the plant of claim 2, wherein said seed pod comprises said full knock-out mutant IND alleles.

4. A *Brassica* plant, or a cell, part, seed or progeny thereof, comprising at least two IND genes and comprising only two mutant IND alleles in its genome, wherein said mutant IND alleles are full knock-out mutant alleles of a gene encoding a functional INDEHISCENT (IND) protein comprising a nucleic acid having the sequence of SEQ ID NO: 3, said full knock-out mutant alleles having the sequence of SEQ ID NO: 3 in which the c at position 148 is substituted with t, or in which the c at position 403 is substituted with t, wherein said plant has increased seed yield compared to the seed yield of a corresponding plant not comprising full knock-out mutant IND alleles.

5. The *Brassica* plant, or a cell, part, seed or progeny thereof, of claim 2, which is plant, or a cell, part, seed or progeny thereof from *Brassica napus, Brassica juncea*, or *Brassica carinata*, wherein said *Brassica* plant, or a cell, part, seed or progeny thereof comprises said full knock-out mutant IND alleles.

6. The *Brassica* plant, or a cell, part, seed or progeny thereof, of claim 4, reference seed comprising said allele having the sequence of SEQ ID NO: 3 in which the c at position 148 is substituted with t having been deposited at the ATCC, under accession number PTA-8796, and said allele having the sequence of SEQ ID NO: 3 in which the c at position 403 is substituted with t having been deposited at the ATCC, under accession number PTA-8795.

7. A seed having been deposited at the ATCC, under accession number PTA-8796 or PTA-8795.

8. The *Brassica* plant, or a cell, part, seed or progeny thereof, of claim 1, wherein said two full knock-out mutant IND alleles are homozygous.

9. The *Brassica* plant, or a cell, part, seed or progeny thereof, of claim 1, wherein said full knock-out mutant IND alleles are (ii) mutant IND alleles encoding a truncated IND protein of which at least the Helix-Loop-Helix domain at positions corresponding to positions 132 to 174 of SEQ ID NO: 10 is lacking or substituted.

10. The *Brassica* plant, or a cell, part, seed or progeny thereof, of claim 1, wherein said full knock-out mutant IND alleles are (iii) mutant IND alleles with a missense mutation of the codon encoding the amino acid at a position corresponding to position 128 of SEQ ID NO: 10.

* * * * *

UNITED STATES PATENT AND TRADEMARK OFFICE
CERTIFICATE OF CORRECTION

| | | |
|---|---|---|
| PATENT NO. | : 9,475,849 B2 | Page 1 of 1 |
| APPLICATION NO. | : 12/745106 | |
| DATED | : October 25, 2016 | |
| INVENTOR(S) | : Benjamin Laga et al. | |

It is certified that error appears in the above-identified patent and that said Letters Patent is hereby corrected as shown below:

In the Claims

Claim 2, Column 89, Line 17 Reads:
 wherein said full knock-out mutants IND allele are:

Should Read:
wherein said full knock-out mutant IND alleles are:

Signed and Sealed this
Third Day of January, 2017

Michelle K. Lee
*Director of the United States Patent and Trademark Office*

SEQUENCE LISTING

<160> NUMBER OF SEQ ID NOS: 40

<210> SEQ ID NO 1
<211> LENGTH: 558
<212> TYPE: DNA
<213> ORGANISM: Brassica napus
<220> FEATURE:
<221> NAME/KEY: CDS
<222> LOCATION: (1)..(555)
<220> FEATURE:
<221> NAME/KEY: misc_feature
<222> LOCATION: (1)..(558)
<223> OTHER INFORMATION: Brassica napus wild type IND-A1 coding sequence

<400> SEQUENCE: 1

```
atg tct ggc tca aaa gca gat gca gcc ata gcc cca ata gtc atg atg      48
Met Ser Gly Ser Lys Ala Asp Ala Ala Ile Ala Pro Ile Val Met Met
1               5                   10                  15 gag cat cat cat ctc ctt atg aat tgg aac aaa cct att gat ctc att      96
Glu His His His Leu Leu Met Asn Trp Asn Lys Pro Ile Asp Leu Ile
            20                  25                  30 aca gaa gaa aac tct ttt aac cac aat cct cat ttc ata gta gat cca     144
Thr Glu Glu Asn Ser Phe Asn His Asn Pro His Phe Ile Val Asp Pro
        35                  40                  45 cct tcc gaa acc cta agc cac ttc cag ccc ccg ccg aca atc ttc tcc     192
Pro Ser Glu Thr Leu Ser His Phe Gln Pro Pro Pro Thr Ile Phe Ser
    50                  55                  60 gat cac gga gga gga gag gaa gca gaa gaa gaa gaa gaa gaa gaa gga     240
Asp His Gly Gly Gly Glu Glu Ala Glu Glu Glu Glu Glu Glu Glu Gly
65                  70                  75                  80 gag gaa gag atg gat ccg atg aag aag atg caa tac gcg att gct gcc     288
Glu Glu Glu Met Asp Pro Met Lys Lys Met Gln Tyr Ala Ile Ala Ala
                85                  90                  95 atg cag ccc gta gac ctc gat cca gcc acc gtt cct aag ccg aac cgc     336
Met Gln Pro Val Asp Leu Asp Pro Ala Thr Val Pro Lys Pro Asn Arg
            100                 105                 110
```

```
cgt aac gta agg gta agc gac gac cct cag acg gtg gtg gct cgt cgg      384
Arg Asn Val Arg Val Ser Asp Asp Pro Gln Thr Val Val Ala Arg Arg
        115                 120                 125 cgt aga gaa agg ata agc gag aag atc cgg ata ttg aag agg atg gtg      432
Arg Arg Glu Arg Ile Ser Glu Lys Ile Arg Ile Leu Lys Arg Met Val
130                 135                 140 cca ggc ggt gca aag atg gac act gcc tcc atg ctc gac gaa gcc atc      480
Pro Gly Gly Ala Lys Met Asp Thr Ala Ser Met Leu Asp Glu Ala Ile
145                 150                 155                 160 cgc tac acc aag ttc ttg aaa cgg cag gtg agg cta gct tct tca gcc      528
Arg Tyr Thr Lys Phe Leu Lys Arg Gln Val Arg Leu Ala Ser Ser Ala
            165                 170                 175 tca cac tca gct tgg agc tcc tat gtc tga                              558
Ser His Ser Ala Trp Ser Ser Tyr Val
            180                 185

<210> SEQ ID NO 2
<211> LENGTH: 185
<212> TYPE: PRT
<213> ORGANISM: Brassica napus

<400> SEQUENCE: 2

Met Ser Gly Ser Lys Ala Asp Ala Ala Ile Ala Pro Ile Val Met Met
1               5                   10                  15

Glu His His Leu Leu Met Asn Trp Asn Lys Pro Ile Asp Leu Ile
            20                  25                  30

Thr Glu Glu Asn Ser Phe Asn His Asn Pro His Phe Ile Val Asp Pro
        35                  40                  45

Pro Ser Glu Thr Leu Ser His Phe Gln Pro Pro Thr Ile Phe Ser
    50                  55                  60

Asp His Gly Gly Gly Glu Glu Ala Glu Glu Glu Glu Glu Glu Gly
65                  70                  75                  80

Glu Glu Glu Met Asp Pro Met Lys Lys Met Gln Tyr Ala Ile Ala Ala
                85                  90                  95

Met Gln Pro Val Asp Leu Asp Pro Ala Thr Val Pro Lys Pro Asn Arg
            100                 105                 110

Arg Asn Val Arg Val Ser Asp Asp Pro Gln Thr Val Val Ala Arg Arg
        115                 120                 125

Arg Arg Glu Arg Ile Ser Glu Lys Ile Arg Ile Leu Lys Arg Met Val
    130                 135                 140

Pro Gly Gly Ala Lys Met Asp Thr Ala Ser Met Leu Asp Glu Ala Ile
145                 150                 155                 160

Arg Tyr Thr Lys Phe Leu Lys Arg Gln Val Arg Leu Ala Ser Ser Ala
                165                 170                 175

Ser His Ser Ala Trp Ser Ser Tyr Val
            180                 185

<210> SEQ ID NO 3
<211> LENGTH: 633
<212> TYPE: DNA
<213> ORGANISM: Brassica napus
<220> FEATURE:
<221> NAME/KEY: CDS
<222> LOCATION: (1)..(630)
<220> FEATURE:
<221> NAME/KEY: misc_feature
<222> LOCATION: (1)..(633)
<223> OTHER INFORMATION: Brassica napus wild-type IND-C1 coding sequence

<400> SEQUENCE: 3
```

-continued

```
atg tat aaa aga aag gtc tat gcg tct cta gtc caa aaa ctc tat atg       48
Met Tyr Lys Arg Lys Val Tyr Ala Ser Leu Val Gln Lys Leu Tyr Met
1               5                   10                  15 tct ggt tca aaa gca gat gca gcc ata gcc cca ata gtc atg atg           96
Ser Gly Ser Lys Ala Asp Ala Ala Ile Ala Pro Ile Val Met Met
                20                  25                  30 gag cct cat cat ctc ctt atg aac tgg aac aaa cct att gat ctc att      144
Glu Pro His His Leu Leu Met Asn Trp Asn Lys Pro Ile Asp Leu Ile
            35                  40                  45 aca caa gaa aac tct ttt aac cac aat cct cat ttc atg gta gat cca      192
Thr Gln Glu Asn Ser Phe Asn His Asn Pro His Phe Met Val Asp Pro
        50                  55                  60 cct tcc gaa acc cta agc cac ttc cag ccc ccg ccg aca gtc ttc tcc      240
Pro Ser Glu Thr Leu Ser His Phe Gln Pro Pro Pro Thr Val Phe Ser
65                  70                  75                  80 gat ccc gga gga gga gag gaa gca gaa gac gaa gaa gga gag gaa gag      288
Asp Pro Gly Gly Gly Glu Glu Ala Glu Asp Glu Glu Gly Glu Glu Glu
                85                  90                  95 ata gat gag atg aag gag atg caa tac gcg att gct gcc atg cag ccc      336
Ile Asp Glu Met Lys Glu Met Gln Tyr Ala Ile Ala Ala Met Gln Pro
            100                 105                 110 gta gac atc gat cca gcc acc gtt cct aag ccg aac cgc cgt aac gta      384
Val Asp Ile Asp Pro Ala Thr Val Pro Lys Pro Asn Arg Arg Asn Val
        115                 120                 125 agg gta agc gag gac ccc cag acg gtg gtg gct cgt cgg cgt aga gaa      432
Arg Val Ser Glu Asp Pro Gln Thr Val Val Ala Arg Arg Arg Arg Glu
130                 135                 140 agg ata agc gag aag atc cgg ata ttg aag agg atg gtg cca ggc ggt      480
Arg Ile Ser Glu Lys Ile Arg Ile Leu Lys Arg Met Val Pro Gly Gly
145                 150                 155                 160 gca aag atg gac act gcc tcc atg ctt gac gaa gcc atc cgc tac acc      528
Ala Lys Met Asp Thr Ala Ser Met Leu Asp Glu Ala Ile Arg Tyr Thr
                165                 170                 175 aag ttc ttg aaa cgg cag gtg agg ctt ctt cag cct cac act cag ctt      576
Lys Phe Leu Lys Arg Gln Val Arg Leu Leu Gln Pro His Thr Gln Leu
            180                 185                 190 ggg gct cct atg tct gac cct tct cgc ctt tgt tat tac cac aac tcg      624
Gly Ala Pro Met Ser Asp Pro Ser Arg Leu Cys Tyr Tyr His Asn Ser
        195                 200                 205 gat acc taa                                                          633
Asp Thr
    210
```

```
<210> SEQ ID NO 4
<211> LENGTH: 210
<212> TYPE: PRT
<213> ORGANISM: Brassica napus

<400> SEQUENCE: 4
```

```
Met Tyr Lys Arg Lys Val Tyr Ala Ser Leu Val Gln Lys Leu Tyr Met
1               5                   10                  15

Ser Gly Ser Lys Ala Asp Ala Ala Ile Ala Pro Ile Val Met Met
                20                  25                  30

Glu Pro His His Leu Leu Met Asn Trp Asn Lys Pro Ile Asp Leu Ile
            35                  40                  45

Thr Gln Glu Asn Ser Phe Asn His Asn Pro His Phe Met Val Asp Pro
        50                  55                  60

Pro Ser Glu Thr Leu Ser His Phe Gln Pro Pro Pro Thr Val Phe Ser
65                  70                  75                  80
```

```
Asp Pro Gly Gly Gly Glu Glu Ala Glu Asp Glu Gly Glu Glu
            85                  90                  95
Ile Asp Glu Met Lys Glu Met Gln Tyr Ala Ile Ala Ala Met Gln Pro
            100                 105                 110
Val Asp Ile Asp Pro Ala Thr Val Pro Lys Pro Asn Arg Arg Asn Val
            115                 120                 125
Arg Val Ser Glu Asp Pro Gln Thr Val Val Ala Arg Arg Arg Glu
            130                 135                 140
Arg Ile Ser Glu Lys Ile Arg Ile Leu Lys Arg Met Val Pro Gly Gly
145                 150                 155                 160
Ala Lys Met Asp Thr Ala Ser Met Leu Asp Glu Ala Ile Arg Tyr Thr
                165                 170                 175
Lys Phe Leu Lys Arg Gln Val Arg Leu Leu Gln Pro His Thr Gln Leu
                180                 185                 190
Gly Ala Pro Met Ser Asp Pro Ser Arg Leu Cys Tyr Tyr His Asn Ser
                195                 200                 205
Asp Thr
    210

<210> SEQ ID NO 5
<211> LENGTH: 1622
<212> TYPE: DNA
<213> ORGANISM: Brassica napus
<220> FEATURE:
<221> NAME/KEY: misc_feature
<222> LOCATION: (1)..(1622)
<223> OTHER INFORMATION: Brassica napus wild type IND-A1 genomic
      sequence
<220> FEATURE:
<221> NAME/KEY: CDS
<222> LOCATION: (561)..(1118)

<400> SEQUENCE: 5
tttgacaatc tacatacata accaacaaaa agtagaatac cttgaaaatc taaaacccaa      60
aatatgatgt aaaactcaag cttggtccag agcataaaaa aattaaagcc atcgctttgg    120
tatcacatat ttaaacgtca gttttttttt ttttttgggg ggggggggg ggggtaatat    180 aaaaatataa ttaacaaaaa aaaattatga acaattagc atgtaaaaca ctaatctttt    240
ggttgtgaca aaacgttttc acaaatgttc tataaataaa ttcaagtgca ttttatctgc    300
aaaatatata ctttcactca taaaataaga gcgtttaaaa cattcataca cgcactacat    360
tgacatgaca aaagaaatcc gcaaatacac atgatgtatg tcgaaaaaaa caaaaaatac    420
acatgatgta tatatagaga ggatagtatc taggaaataa gactatatta tatatataaa    480 gaaatagag aaaagataaa aatataaatt ggtatgtata aaagaaaggt ctatgcgtct    540
ctagtccaaa aactctatat atg tct ggc tca aaa gca gat gca gcc ata gcc    593
                        Met Ser Gly Ser Lys Ala Asp Ala Ala Ile Ala
                         1               5                   10 cca ata gtc atg atg gag cat cat cat ctc ctt atg aat tgg aac aaa    641
Pro Ile Val Met Met Glu His His His Leu Leu Met Asn Trp Asn Lys
            15                  20                  25 cct att gat ctc att aca gaa gaa aac tct ttt aac cac aat cct cat    689
Pro Ile Asp Leu Ile Thr Glu Glu Asn Ser Phe Asn His Asn Pro His
        30                  35                  40 ttc ata gta gat cca cct tcc gaa acc cta agc cac ttc cag ccc ccg    737
Phe Ile Val Asp Pro Pro Ser Glu Thr Leu Ser His Phe Gln Pro Pro
    45                  50                  55 ccg aca atc ttc tcc gat cac gga gga gga gag gaa gca gaa gaa gaa    785
```

```
Pro Thr Ile Phe Ser Asp His Gly Gly Gly Glu Ala Glu Glu Glu
 60                  65                  70                  75 gaa gaa gaa gaa gga gag gaa gag atg gat ccg atg aag aag atg caa        833
Glu Glu Glu Glu Gly Glu Glu Glu Met Asp Pro Met Lys Lys Met Gln
                     80                  85                  90 tac gcg att gct gcc atg cag ccc gta gac ctc gat cca gcc acc gtt        881
Tyr Ala Ile Ala Ala Met Gln Pro Val Asp Leu Asp Pro Ala Thr Val
                 95                 100                 105 cct aag ccg aac cgc cgt aac gta agg gta agc gac gac cct cag acg        929
Pro Lys Pro Asn Arg Arg Asn Val Arg Val Ser Asp Asp Pro Gln Thr
             110                 115                 120 gtg gtg gct cgt cgg cgt aga gaa agg ata agc gag aag atc cgg ata        977
Val Val Ala Arg Arg Arg Arg Glu Arg Ile Ser Glu Lys Ile Arg Ile
         125                 130                 135 ttg aag agg atg gtg cca ggc ggt gca aag atg gac act gcc tcc atg       1025
Leu Lys Arg Met Val Pro Gly Gly Ala Lys Met Asp Thr Ala Ser Met
140                 145                 150                 155 ctc gac gaa gcc atc cgc tac acc aag ttc ttg aaa cgg cag gtg agg       1073
Leu Asp Glu Ala Ile Arg Tyr Thr Lys Phe Leu Lys Arg Gln Val Arg
                160                 165                 170 cta gct tct tca gcc tca cac tca gct tgg agc tcc tat gtc tga           1118
Leu Ala Ser Ser Ala Ser His Ser Ala Trp Ser Ser Tyr Val
            175                 180                 185 cccttcttgc ctttgttatt accacaactc ggatacctaa ttataattct atcacgcgtt     1178
tcatgttgat atatatagat aaatggtcga ataaggattt cgatcgaaga ttgtatgtac     1238
aataaatgat gtgtgtattt caattaatgt atgatatata tatatatatg tatgcagtat     1298
gcatttatat tctattctct ataaggaggc aacattgccg gatttgggct ttgatcttat     1358
gcaagttttc cgaccaaaaa tatgaaatac ttgtttggat ataacatatg aatcggataa     1418
gtgttactag ttatataact ggaaaacaaa tgtctggaat aagaattccc gggagaacca     1478
agcctttctc taatccctaa gattatagct actgaaacaa tgaaacaatg aagaatcagt     1538
tgggcattag taaaaaaaaa agaatcagtt gggttgctta taaatttttg ttataaaatt     1598
tatgtcgtat gtgtgttagc cgta                                            1622

<210> SEQ ID NO 6
<211> LENGTH: 185
<212> TYPE: PRT
<213> ORGANISM: Brassica napus

<400> SEQUENCE: 6

Met Ser Gly Ser Lys Ala Asp Ala Ala Ile Ala Pro Ile Val Met Met
  1               5                  10                  15

Glu His His Leu Leu Met Asn Trp Asn Lys Pro Ile Asp Leu Ile
             20                  25                  30

Thr Glu Glu Asn Ser Phe Asn His Asn Pro His Phe Ile Val Asp Pro
         35                  40                  45

Pro Ser Glu Thr Leu Ser His Phe Gln Pro Pro Thr Ile Phe Ser
     50                  55                  60

Asp His Gly Gly Gly Glu Glu Ala Glu Glu Glu Glu Glu Glu Gly
 65                  70                  75                  80

Glu Glu Glu Met Asp Pro Met Lys Lys Met Gln Tyr Ala Ile Ala Ala
                 85                  90                  95

Met Gln Pro Val Asp Leu Asp Pro Ala Thr Val Pro Lys Pro Asn Arg
            100                 105                 110

Arg Asn Val Arg Val Ser Asp Asp Pro Gln Thr Val Val Ala Arg Arg
```

```
                 115                 120                 125
Arg Arg Glu Arg Ile Ser Glu Lys Ile Arg Ile Leu Lys Arg Met Val
            130                 135                 140

Pro Gly Gly Ala Lys Met Asp Thr Ala Ser Met Leu Asp Glu Ala Ile
145                 150                 155                 160

Arg Tyr Thr Lys Phe Leu Lys Arg Gln Val Arg Leu Ala Ser Ser Ala
                165                 170                 175

Ser His Ser Ala Trp Ser Ser Tyr Val
            180                 185

<210> SEQ ID NO 7
<211> LENGTH: 1593
<212> TYPE: DNA
<213> ORGANISM: Brassica napus
<220> FEATURE:
<221> NAME/KEY: misc_feature
<222> LOCATION: (1)..(1593)
<223> OTHER INFORMATION: Brassica napus wild type IND-C1 genomic sequence
<220> FEATURE:
<221> NAME/KEY: CDS
<222> LOCATION: (497)..(1126)

<400> SEQUENCE: 7
tgccatacat aaccacggat catagtcgac acctcaacgt gaagcaaatt tgacaatcta      60
catacataac caacaaaaag tagaataccg tgaaaaccta acccaaaat atgatgtaaa      120 actcaagctt ggtccagagc ataaaaaaat taaagccatc gctttggtat cacatattta     180
aacgtcagtt ttttttgggg gaagtaatat aaaaatataa ttaacaagaa aatttatgaa     240
ataattagca tgtaaaacac tagtcttttg gttgtgacaa aacgttttca caaatgttct     300
ataaataaat tcaagcacat tttatctgca aaatatatac tttcactcat aaaataagag     360
cgtttaaaac attcatatac gcactacatt gacatgacaa agaaatccg caaatacaaa      420 catatttagt tcggatatat ctaggaaata agactatatt atatatataa agaaattaga     480 aaaaagaaa attggt atg tat aaa aga aag gtc tat gcg tct cta gtc caa     532
              Met Tyr Lys Arg Lys Val Tyr Ala Ser Leu Val Gln
                1               5                  10 aaa ctc tat atg tct ggt tca aaa gca gat gca gca gcc ata gcc cca        580
Lys Leu Tyr Met Ser Gly Ser Lys Ala Asp Ala Ala Ala Ile Ala Pro
         15                  20                  25 ata gtc atg atg gag cct cat cat ctc ctt atg aac tgg aac aaa cct        628
Ile Val Met Met Glu Pro His His Leu Leu Met Asn Trp Asn Lys Pro
 30                  35                  40 att gat ctc att aca caa gaa aac tct ttt aac cac aat cct cat ttc        676
Ile Asp Leu Ile Thr Gln Glu Asn Ser Phe Asn His Asn Pro His Phe
45                  50                  55                  60 atg gta gat cca cct tcc gaa acc cta agc cac ttc cag ccc ccg ccg        724
Met Val Asp Pro Pro Ser Glu Thr Leu Ser His Phe Gln Pro Pro Pro
                 65                  70                  75 aca gtc ttc tcc gat ccc gga gga gga gag gaa gca gaa gac gaa gaa        772
Thr Val Phe Ser Asp Pro Gly Gly Gly Glu Glu Ala Glu Asp Glu Glu
             80                  85                  90 gga gag gaa gag ata gat gag atg aag gag atg caa tac gcg att gct        820
Gly Glu Glu Glu Ile Asp Glu Met Lys Glu Met Gln Tyr Ala Ile Ala
         95                 100                 105 gcc atg cag ccc gta gac atc gat cca gcc acc gtt cct aag ccg aac        868
Ala Met Gln Pro Val Asp Ile Asp Pro Ala Thr Val Pro Lys Pro Asn
110                 115                 120 cgc cgt aac gta agg gta agc gag gac ccc cag acg gtg gtg gct cgt        916
Arg Arg Asn Val Arg Val Ser Glu Asp Pro Gln Thr Val Val Ala Arg
```

```
                      125                 130                 135                 140
cgg cgt aga gaa agg ata agc gag aag atc cgg ata ttg aag agg atg         964
Arg Arg Arg Glu Arg Ile Ser Glu Lys Ile Arg Ile Leu Lys Arg Met
                145                 150                 155 gtg cca ggc ggt gca aag atg gac act gcc tcc atg ctt gac gaa gcc         1012
Val Pro Gly Gly Ala Lys Met Asp Thr Ala Ser Met Leu Asp Glu Ala
            160                 165                 170 atc cgc tac acc aag ttc ttg aaa cgg cag gtg agg ctt ctt cag cct         1060
Ile Arg Tyr Thr Lys Phe Leu Lys Arg Gln Val Arg Leu Leu Gln Pro
        175                 180                 185 cac act cag ctt ggg gct cct atg tct gac cct tct cgc ctt tgt tat         1108
His Thr Gln Leu Gly Ala Pro Met Ser Asp Pro Ser Arg Leu Cys Tyr
    190                 195                 200 tac cac aac tcg gat acc taattataat tctatcacgc gtttcatgtt                1156
Tyr His Asn Ser Asp Thr
205                 210 gatatatata gataaatggt tgaataagga tttcgatcga agattgtatg gctattgatt       1216
acattatata ttgtacaata aatgatgtgt gtatttctat taatgtatat atgatatata       1276
tctgtttgca gtatgcattt atattctatt ctttataggg aggcaacatg ccggattagg       1336
gctttgatcg tatgcaagtt ttccgaccaa aaatatgaaa tacttgtttg gatataacat       1396
atgaatcgga taagtgttac tagttatata actggaaaaa attgtttggt ataagaattc       1456
ccgggagaac caagcctttc tctaatccct aagatcatag ctactgaaat aatgaaaaaa       1516
aacaaaaaaa aaacaatgaa gaatcagttg ggcattagtc caaaaaaaaa aaagaatcag       1576
ttggattgct tataaaa                                                      1593

<210> SEQ ID NO 8
<211> LENGTH: 210
<212> TYPE: PRT
<213> ORGANISM: Brassica napus

<400> SEQUENCE: 8

Met Tyr Lys Arg Lys Val Tyr Ala Ser Leu Val Gln Lys Leu Tyr Met
1               5                   10                  15

Ser Gly Ser Lys Ala Asp Ala Ala Ile Ala Pro Ile Val Met Met
            20                  25                  30

Glu Pro His His Leu Leu Met Asn Trp Asn Lys Pro Ile Asp Leu Ile
        35                  40                  45

Thr Gln Glu Asn Ser Phe Asn His Asn Pro His Phe Met Val Asp Pro
    50                  55                  60

Pro Ser Glu Thr Leu Ser His Phe Gln Pro Pro Thr Val Phe Ser
65                  70                  75                  80

Asp Pro Gly Gly Gly Glu Glu Ala Glu Asp Glu Glu Gly Glu Glu
                85                  90                  95

Ile Asp Glu Met Lys Glu Met Gln Tyr Ala Ile Ala Ala Met Gln Pro
            100                 105                 110

Val Asp Ile Asp Pro Ala Thr Val Pro Lys Pro Asn Arg Asn Val
        115                 120                 125

Arg Val Ser Glu Asp Pro Gln Thr Val Val Ala Arg Arg Arg Glu
    130                 135                 140

Arg Ile Ser Glu Lys Ile Arg Ile Leu Lys Arg Met Val Pro Gly Gly
145                 150                 155                 160

Ala Lys Met Asp Thr Ala Ser Met Leu Asp Glu Ala Ile Arg Tyr Thr
                165                 170                 175
```

```
                Lys Phe Leu Lys Arg Gln Val Arg Leu Leu Gln Pro His Thr Gln Leu
                            180                 185                 190

Gly Ala Pro Met Ser Asp Pro Ser Arg Leu Cys Tyr Tyr His Asn Ser
                        195                 200                 205

Asp Thr
                    210

<210> SEQ ID NO 9
<211> LENGTH: 597
<212> TYPE: DNA
<213> ORGANISM: Arabidopsis thaliana
<220> FEATURE:
<221> NAME/KEY: CDS
<222> LOCATION: (1)..(594)
<220> FEATURE:
<221> NAME/KEY: misc_feature
<222> LOCATION: (1)..(597)
<223> OTHER INFORMATION: Arabidopsis thaliana IND1

<400> SEQUENCE: 9 atg gaa aat ggt atg tat aaa aag aaa gga gtg tgc gac tct tgt gtc        48
Met Glu Asn Gly Met Tyr Lys Lys Lys Gly Val Cys Asp Ser Cys Val
1               5                   10                  15 tcg tcc aaa agc aga tcc aac cac agc ccc aaa aga agc atg atg gag        96
Ser Ser Lys Ser Arg Ser Asn His Ser Pro Lys Arg Ser Met Met Glu
                20                  25                  30 cct cag cct cac cat ctc ctc atg gat tgg aac aaa gct aat gat ctt       144
Pro Gln Pro His His Leu Leu Met Asp Trp Asn Lys Ala Asn Asp Leu
            35                  40                  45 ctc aca caa gaa cac gca gct ttt ctc aat gat cct cac cat ctc atg       192
Leu Thr Gln Glu His Ala Ala Phe Leu Asn Asp Pro His His Leu Met
        50                  55                  60 tta gat cca cct ccc gaa acc cta att cac ttg gac gaa gac gaa gag       240
Leu Asp Pro Pro Pro Glu Thr Leu Ile His Leu Asp Glu Asp Glu Glu
65                  70                  75                  80 tac gat gaa gac atg gat gcg atg aag gag atg cag tac atg atc gcc       288
Tyr Asp Glu Asp Met Asp Ala Met Lys Glu Met Gln Tyr Met Ile Ala
                85                  90                  95 gtc atg cag ccc gta gac atc gac cct gcc acg gtc cct aag ccg aac       336
Val Met Gln Pro Val Asp Ile Asp Pro Ala Thr Val Pro Lys Pro Asn
            100                 105                 110 cgc cgt aac gta agg ata agc gac gat cct cag acg gtg gtt gct cgt       384
Arg Arg Asn Val Arg Ile Ser Asp Asp Pro Gln Thr Val Val Ala Arg
        115                 120                 125 cgg cgt cgg gaa agg atc agc gag aag atc cga att ctc aag agg atc       432
Arg Arg Arg Glu Arg Ile Ser Glu Lys Ile Arg Ile Leu Lys Arg Ile
    130                 135                 140 gtg cct ggt ggt gcg aag atg gac aca gct tcc atg ctc gac gaa gcc       480
Val Pro Gly Gly Ala Lys Met Asp Thr Ala Ser Met Leu Asp Glu Ala
145                 150                 155                 160 ata cgt tac acc aag ttc ttg aaa cgg cag gtg agg att ctt cag cct       528
Ile Arg Tyr Thr Lys Phe Leu Lys Arg Gln Val Arg Ile Leu Gln Pro
                165                 170                 175 cac tct cag att gga gct cct atg gct aac ccc tct tac ctt tgt tat       576
His Ser Gln Ile Gly Ala Pro Met Ala Asn Pro Ser Tyr Leu Cys Tyr
            180                 185                 190 tac cac aac tcc caa ccc tga                                           597
Tyr His Asn Ser Gln Pro
        195

<210> SEQ ID NO 10
<211> LENGTH: 198
```

-continued

<212> TYPE: PRT
<213> ORGANISM: Arabidopsis thaliana

<400> SEQUENCE: 10

Met Glu Asn Gly Met Tyr Lys Lys Gly Val Cys Asp Ser Cys Val
1               5                   10                  15

Ser Ser Lys Ser Arg Ser Asn His Ser Pro Lys Arg Ser Met Met Glu
            20                  25                  30

Pro Gln Pro His His Leu Leu Met Asp Trp Asn Lys Ala Asn Asp Leu
        35                  40                  45

Leu Thr Gln Glu His Ala Ala Phe Leu Asn Asp Pro His His Leu Met
    50                  55                  60

Leu Asp Pro Pro Glu Thr Leu Ile His Leu Asp Glu Asp Glu Glu
65                  70                  75                  80

Tyr Asp Glu Asp Met Asp Ala Met Lys Glu Met Gln Tyr Met Ile Ala
                85                  90                  95

Val Met Gln Pro Val Asp Ile Asp Pro Ala Thr Val Pro Lys Pro Asn
                100                 105                 110

Arg Arg Asn Val Arg Ile Ser Asp Asp Pro Gln Thr Val Val Ala Arg
            115                 120                 125

Arg Arg Arg Glu Arg Ile Ser Glu Lys Ile Arg Ile Leu Lys Arg Ile
        130                 135                 140

Val Pro Gly Gly Ala Lys Met Asp Thr Ala Ser Met Leu Asp Glu Ala
145                 150                 155                 160

Ile Arg Tyr Thr Lys Phe Leu Lys Arg Gln Val Arg Ile Leu Gln Pro
                165                 170                 175

His Ser Gln Ile Gly Ala Pro Met Ala Asn Pro Ser Tyr Leu Cys Tyr
            180                 185                 190

Tyr His Asn Ser Gln Pro
        195

<210> SEQ ID NO 11
<211> LENGTH: 643
<212> TYPE: DNA
<213> ORGANISM: Brassica napus
<220> FEATURE:
<221> NAME/KEY: misc_feature
<222> LOCATION: (1)..(643)
<223> OTHER INFORMATION: Nucleotide sequence of a INDEHISCENT homologue
      from Brassica napus (Bn1-IND - SEQ ID NO: 2 of WO04/113542 )

<400> SEQUENCE: 11
gaattcgccc ttcgcatgta taaaagaag ggtctatgcg tctctagtcc aaaaactcta      60
tatgtctggt tcaaaagcag atgcagcagc catagcccca atagtcatga tggagcctca     120
tcatctcctt atgaactgga acaaaccta tgatctcatt acacaagaaa actcttttaa     180
ccacaatcct catttcatgg tagatccacc ttccgaaacc ctaagccact ccagccccc     240 gccgacagtc ttctccgatc ccggaggagg agaggaagca gaagacgaag aaggagagga     300
agagatagat gagatgaagg agatgcaata cgcgattgct gccatgcagc ccgtagacat     360
cgatccagcc accgttccta agccgaaccg ccgtaacgta agggtaagcg aggacccca     420 gacggtggtg gctcgtcggc gtagagaaag gataagcgag aagatccgga tattgaagag     480
gatggtgcca ggcggtgcaa agatggacac tgcctccatg cttgacgaag ccatccgcta     540
caccaagttc ttgaaacggc aggtgaggct tcttcagcct cacactcagc ttggggctcc     600
tatgtctgac ccttctcgcc tttgttatta ccacaactct caa                      643

<210> SEQ ID NO 12
<211> LENGTH: 660
<212> TYPE: DNA
<213> ORGANISM: Brassica napus
<220> FEATURE:
<221> NAME/KEY: misc_feature
<222> LOCATION: (1)..(660)
<223> OTHER INFORMATION: Nucleotide sequence of a second INDEHISCENT homologue from Brassica napus (Bn2-IND - SEQ ID NO: 3 of WO04/113542 )

<400> SEQUENCE: 12

```
gaattcgccc ttggcatgta caagaagaaa ggtctatgcg tctctagtcc aaaaactcta      60
tatatgtctg gctcaaaagc agatgcagcc atagccccaa tagtcatgat ggagcatcat     120
catctcctta tgaattggaa caaacctatt gatctcatta cagaagaaaa ctcttttaac     180
cacaatcctc atttcatagt agatccacct tccgaaaccc taagccactt ccagccccccg    240
ccgacaatct tctccggtca cggaggagga gaggaagcag cagaagaaga agaagaagaa     300
ggagaggaag agatggatcc gatgaagaag atgcaatacg cgattgctgc catgcagccc     360
gtagacctcg atccagccac cgttcctaag ccgaaccgcc gtaacgtaag ggtaagcgac     420
gaccctcaga cggtggtggc tcgtcggcgt agagaaagga taagcgagaa gatccggata     480
ttgaggagga tggtgccagg cggtgcaaag atggacactg cctccatgct cgacgaagcc     540
atccgctaca ccaagttctt gaaacggcag gtgaggctag cttcttcagc ctcacactca     600
gcttggagct cctatgtctg acccttcttg cctttgttat tatcataact cgcagccctg     660
```

<210> SEQ ID NO 13
<211> LENGTH: 20
<212> TYPE: DNA
<213> ORGANISM: Artificial Sequence
<220> FEATURE:
<223> OTHER INFORMATION: forward oligonucleotide for detection of IND-A1-EMS01

<400> SEQUENCE: 13

```
aagggtaagc gacgacccctt                                                  20
```

<210> SEQ ID NO 14
<211> LENGTH: 20
<212> TYPE: DNA
<213> ORGANISM: Artificial Sequence
<220> FEATURE:
<223> OTHER INFORMATION: Forward oligonucleotide for detection of IND-A1-WT

<400> SEQUENCE: 14

```
aagggtaagc gacgaccctc                                                   20
```

<210> SEQ ID NO 15
<211> LENGTH: 20
<212> TYPE: DNA
<213> ORGANISM: Artificial Sequence
<220> FEATURE:
<223> OTHER INFORMATION: Reverse oligonucleotide for detection of IND-A1-EMS01 and -WT

<400> SEQUENCE: 15

```
gagtgtgagg ctgaagaagc                                                   20
```

<210> SEQ ID NO 16
<211> LENGTH: 20
<212> TYPE: DNA

<213> ORGANISM: Artificial Sequence
<220> FEATURE:
<223> OTHER INFORMATION: Forward oligonucleotide for detection of IND-A1-EMS05

<400> SEQUENCE: 16
cctcagacgg tggtggctca					20

<210> SEQ ID NO 17
<211> LENGTH: 20
<212> TYPE: DNA
<213> ORGANISM: Artificial Sequence
<220> FEATURE:
<223> OTHER INFORMATION: Forward oligonucleotide for detection of IND-A1-WT

<400> SEQUENCE: 17
cctcagacgg tggtggctcg					20

<210> SEQ ID NO 18
<211> LENGTH: 20
<212> TYPE: DNA
<213> ORGANISM: Artificial Sequence
<220> FEATURE:
<223> OTHER INFORMATION: Reverse oligonucleotide for detection of IND-A1-EMS05 and -WT

<400> SEQUENCE: 18
agggtcagac ataggagctc					20

<210> SEQ ID NO 19
<211> LENGTH: 21
<212> TYPE: DNA
<213> ORGANISM: Artificial Sequence
<220> FEATURE:
<223> OTHER INFORMATION: Reverse oligonucleotide for detection of IND-C1-EMS01

<400> SEQUENCE: 19
gtggttaaaa gagttttctt a					21

<210> SEQ ID NO 20
<211> LENGTH: 21
<212> TYPE: DNA
<213> ORGANISM: Artificial Sequence
<220> FEATURE:
<223> OTHER INFORMATION: Reverse oligonucleotide for detection of IND-C1-WT

<400> SEQUENCE: 20
gtggttaaaa gagttttctt g					21

<210> SEQ ID NO 21
<211> LENGTH: 20
<212> TYPE: DNA
<213> ORGANISM: Artificial Sequence
<220> FEATURE:
<223> OTHER INFORMATION: Forward oligonucleotide for detection of IND-C1-EMS01 and -WT

<400> SEQUENCE: 21
attagcatgt aaaacactag					20

<210> SEQ ID NO 22
<211> LENGTH: 19
<212> TYPE: DNA
<213> ORGANISM: Artificial Sequence

```
<220> FEATURE:
<223> OTHER INFORMATION: Reverse oligonucleotide for detection of
      IND-C1-EMS03

<400> SEQUENCE: 22
acgagccacc accgtctag                                                   19

<210> SEQ ID NO 23
<211> LENGTH: 18
<212> TYPE: DNA
<213> ORGANISM: Artificial Sequence
<220> FEATURE:
<223> OTHER INFORMATION: Reverse oligonucleotide for detection of
      IND-C1-WT

<400> SEQUENCE: 23
acgagccacc accgtctg                                                    18

<210> SEQ ID NO 24
<211> LENGTH: 21
<212> TYPE: DNA
<213> ORGANISM: Artificial Sequence
<220> FEATURE:
<223> OTHER INFORMATION: Forward oligonucleotide for detection of
      IND-C1-EMS03 and -WT

<400> SEQUENCE: 24
gttcaaaagc agatgcagca g                                                21

<210> SEQ ID NO 25
<211> LENGTH: 22
<212> TYPE: DNA
<213> ORGANISM: Artificial Sequence
<220> FEATURE:
<223> OTHER INFORMATION: oligonucleotide for detection of IND-A1-
      EMS01 and -WT

<400> SEQUENCE: 25
gccgacgagc caccaccgtc tt                                               22

<210> SEQ ID NO 26
<211> LENGTH: 14
<212> TYPE: DNA
<213> ORGANISM: Artificial Sequence
<220> FEATURE:
<223> OTHER INFORMATION: oligonucleotide for detection of IND-A1-EMS01

<400> SEQUENCE: 26
aagggtcgtc gctt                                                        14

<210> SEQ ID NO 27
<211> LENGTH: 13
<212> TYPE: DNA
<213> ORGANISM: Artificial Sequence
<220> FEATURE:
<223> OTHER INFORMATION: oligonucleotide for detection of IND-A1-WT

<400> SEQUENCE: 27
gagggtcgtc gct                                                         13

<210> SEQ ID NO 28
<211> LENGTH: 34
<212> TYPE: DNA
<213> ORGANISM: Artificial Sequence
<220> FEATURE:
<223> OTHER INFORMATION: oligonucleotide for detection of IND-A1-EMS05
      and -WT
```

```
<400> SEQUENCE: 28
cggatcttct cgcttatcct ttctctacgc cgaa                                    34

<210> SEQ ID NO 29
<211> LENGTH: 13
<212> TYPE: DNA
<213> ORGANISM: Artificial Sequence
<220> FEATURE:
<223> OTHER INFORMATION: oligonucleotide for detection of IND-A1-EMS05

<400> SEQUENCE: 29
tgagccacca ccg                                                           13

<210> SEQ ID NO 30
<211> LENGTH: 13
<212> TYPE: DNA
<213> ORGANISM: Artificial Sequence
<220> FEATURE:
<223> OTHER INFORMATION: oligonucleotide for detection of IND-A1-WT

<400> SEQUENCE: 30
cgagccacca ccg                                                           13

<210> SEQ ID NO 31
<211> LENGTH: 48
<212> TYPE: DNA
<213> ORGANISM: Artificial Sequence
<220> FEATURE:
<223> OTHER INFORMATION: oligonucleotide for detection of IND-C1-EMS01
      and -WT

<400> SEQUENCE: 31
aggtggatct accatgaaat gaggattgtg gttaaaagag ttttcttt                     48

<210> SEQ ID NO 32
<211> LENGTH: 23
<212> TYPE: DNA
<213> ORGANISM: Artificial Sequence
<220> FEATURE:
<223> OTHER INFORMATION: oligonucleotide for detection of IND-C1-EMS01

<400> SEQUENCE: 32
atgtaatgag atcaataggt ttg                                                23

<210> SEQ ID NO 33
<211> LENGTH: 23
<212> TYPE: DNA
<213> ORGANISM: Artificial Sequence
<220> FEATURE:
<223> OTHER INFORMATION: oligonucleotide for detection of IND-C1-WT

<400> SEQUENCE: 33
gtgtaatgag atcaataggt ttg                                                23

<210> SEQ ID NO 34
<211> LENGTH: 29
<212> TYPE: DNA
<213> ORGANISM: Artificial Sequence
<220> FEATURE:
<223> OTHER INFORMATION: oligonucleotide for detection of IND-C1-EMS03
      and -WT

<400> SEQUENCE: 34
ccgtaacgta agggtaagcg aggacccca                                          29
```

```
<210> SEQ ID NO 35
<211> LENGTH: 14
<212> TYPE: DNA
<213> ORGANISM: Artificial Sequence
<220> FEATURE:
<223> OTHER INFORMATION: oligonucleotide for detection of IND-C1-EMS03

<400> SEQUENCE: 35
tagacggtgg tggc                                                      14

<210> SEQ ID NO 36
<211> LENGTH: 14
<212> TYPE: DNA
<213> ORGANISM: Artificial Sequence
<220> FEATURE:
<223> OTHER INFORMATION: oligonucleotide for detection of IND-C1-WT

<400> SEQUENCE: 36
cagacggtgg tggc                                                      14

<210> SEQ ID NO 37
<211> LENGTH: 21
<212> TYPE: DNA
<213> ORGANISM: Artificial Sequence
<220> FEATURE:
<223> OTHER INFORMATION: Forward oligonucleotide for detection of IND-A1

<400> SEQUENCE: 37
aggagaggaa gagatggatc c                                              21

<210> SEQ ID NO 38
<211> LENGTH: 21
<212> TYPE: DNA
<213> ORGANISM: Artificial Sequence
<220> FEATURE:
<223> OTHER INFORMATION: Reverse oligonucleotide for detection of IND-A1

<400> SEQUENCE: 38
tgagtgtgag gctgaagaag c                                              21

<210> SEQ ID NO 39
<211> LENGTH: 21
<212> TYPE: DNA
<213> ORGANISM: Artificial Sequence
<220> FEATURE:
<223> OTHER INFORMATION: Forward oligonucleotide for detection of IND-C1

<400> SEQUENCE: 39
cctcatcatc tccttatgaa c                                              21

<210> SEQ ID NO 40
<211> LENGTH: 21
<212> TYPE: DNA
<213> ORGANISM: Artificial Sequence
<220> FEATURE:
<223> OTHER INFORMATION: Reverse oligonucleotide for detection of IND-C1

<400> SEQUENCE: 40
cgtattgcat ctccttcatc t                                              21
```